United States Patent
Soejima et al.

(10) Patent No.: US 7,361,748 B2
(45) Date of Patent: Apr. 22, 2008

(54) VON WILLEBRAND FACTOR (VWF)—CLEAVING PROTEASE

(75) Inventors: Kenji Soejima, Kikuchi-gun (JP); Noriko Mimura, Kikuchi-gun (JP); Hiroaki Maeda, Kikuchi-gun (JP); Chikateru Nozaki, Kikuchi-gun (JP); Takayoshi Hamamoto, Kumamoto (JP); Tomohiro Nakagaki, Kumamoto (JP)

(73) Assignee: Juridical Foundation the Chemo-Sero-Therapeutic Research Institute, Kumamoto (JP)

( * ) Notice: Subject to any disclaimer, the term of this patent is extended or adjusted under 35 U.S.C. 154(b) by 0 days.

(21) Appl. No.: 11/296,294

(22) Filed: Dec. 8, 2005

(65) Prior Publication Data

US 2006/0073569 A1    Apr. 6, 2006

Related U.S. Application Data

(62) Division of application No. 10/475,538, filed as application No. PCT/JP02/04141 on Apr. 25, 2002, now Pat. No. 7,112,666.

(30) Foreign Application Priority Data

| Apr. 25, 2001 | (JP) | ............................. 2001-128342 |
| Jul. 27, 2001 | (JP) | ............................. 2001-227510 |
| Sep. 28, 2001 | (JP) | ............................. 2001-302977 |
| Jan. 25, 2002 | (JP) | ............................. 2002-017596 |

(51) Int. Cl.
*C07H 21/04* (2006.01)
*C07K 14/00* (2006.01)

(52) U.S. Cl. ..................................... 536/23.1; 530/350
(58) Field of Classification Search ...................... None
See application file for complete search history.

(56) References Cited

U.S. PATENT DOCUMENTS

2001/0049106 A1    12/2001    Buckbinder et al.
2002/0151702 A1*   10/2002    Racie et al. ............... 536/23.2

FOREIGN PATENT DOCUMENTS

| EP | 1 152 055 A1 | 7/2001 |
| WO | WO 97/41206 A3 | 7/2000 |
| WO | WO 02/26999 A2 | 4/2002 |
| WO | WO 02 42441 A2 | 5/2002 |

OTHER PUBLICATIONS

STIC : OM nucleic-nucleic search, using sw model, Run on: Feb. 26, 2007, pp. 1-3.*
Fujikawa et al., "Purification of human von Willebrand factor-cleaving protease and its identification as a new member of the metalloproteinase family", Blood, vol. 98, No. 6, Sep. 15, 2001, pp. 1662-1666.
Furlan et al., "Partial Purification and Characterization of a Protease From Human Plasma Cleaving von Willebrand Factor to Fragments Produced by In Vivo Proteolysis", Blood, vol. 87, No. 10, May 15, 1996, pp. 4223-4234.
Furlan, et al., "Acquired Deficiency of von Willebrand Factor-Cleaving Protease in a Patient With Thrombotic Thtombocytopenic Purpura", Blood, vol. 29, No. 8, pp. 2839-2846 (Apr. 15, 1998).
Gerritsen et al., "Partial amino acid sequence of purified von Willebrand factor-cleaving protease", Blood, vol. 98, No. 6, Sep. 15, 2001, pp. 1654-1661.
Levy et al., "Mutations in a member of the *ADAMTS* gene family cause thrombotic thrombocytopenic purpura", Nature, vol. 413, Oct. 4, 2001, pp. 488-494.
Soejima et al., "A Novel Human Metalloprotease Synthesized in the Liver and Secreted into the Blood: Possibly, the von Willebrand Factor-Cleaving Protease?", J. Biochem. vol. 130, No. 4, 2001, pp. 475-480.
Tsai, Han-Mou, "Physiologic Cleavage of von Willebrand Factor by a Plasma Protease Is Dependent on Its Conformation and Requires Calcium Ion", Blood, vol. 87, No. 10, May 15, 1996, pp. 4235-4244.
Zheng et al., "Structure of von Willebrand Factor-cleaving Protease (ADAMTS13), a Metalloprotease Involved in Thrombotic Thrombocytopenic Purpura", The Journal of Biological Chemistry, vol. 276, No. 44, Nov. 2, 2001, pp. 41059-41063.

* cited by examiner

*Primary Examiner*—Robert B. Mondesi
(74) *Attorney, Agent, or Firm*—Foley & Lardner LLP

(57) ABSTRACT

This invention is intended to isolate and identify a vWF-specific cleaving protease. The vWF-specific cleaving protease cleaves a bond between residues Tyr 842 and Met 843 of vWF and comprises a polypeptide chain having Leu-Leu-Val-Ala-Val (SEQ ID NO: 1) as a partial sequence, and more preferably comprises a polypeptide chain having the partial N-terminal amino acid sequence of a mature protein, Ala-Ala-Gly-Gly-Ile-Leu-His-Leu-Glu-Leu-Leu-Val-Ala-Val (SEQ ID NO: 2), and having a molecular weight of 105 to 160 kDa in SDS-PAGE under reducing or non-reducing conditions. Isolation and identification of this vWF-specific cleaving protease have led to the possibility of replacement therapy for patients having diseases resulting from a deficiency of the protease, such as thrombotic thrombocytopenic purpura.

4 Claims, 26 Drawing Sheets

FIG. 2
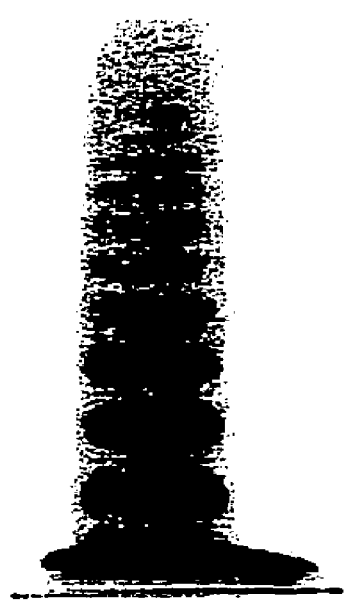
Normal human plasma
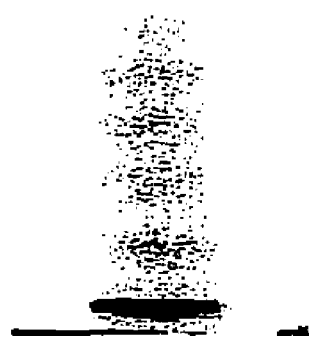
Purified vWF

Pool

FIG. 9

```
gct gca ggc ggc atc cta cac ctg gag ctg ctg gtg gcc gtg ggc
Ala Ala Gly Gly Ile Leu His Leu Glu Leu Leu Val Ala Val Gly
 1           5               10              15
ccc gat gtc ttc cag gct cac cag aag gac aca gag cgc tat gtg
Pro Asp Val Phe Gln Ala His Gln Lys Asp Thr Glu Arg Tyr Val
             20              25              30
ctc acc aac ctc aac atc ggg gca gaa ctg ctt cgg gac ccg tcc
Leu Thr Asn Leu Asn Ile Gly Ala Glu Leu Leu Arg Asp Pro Ser
                 35              40              45
ctg ggg gct cag ttt cgg gtg cac ctg gtg aag atg gtc att ctg
Leu Gly Ala Gln Phe Arg Val His Leu Val Lys Met Val Ile Leu
             50              55              60
aca gag cct gag ggt gct cca aat atc aca gca aac ctc acc tcg
Thr Glu Pro Glu Gly Ala Pro Asn Ile Thr Ala Asn Leu Thr Ser
                 65              70              75
tcc ctg ctg agc gtc tgt ggg tgg agc cag acc atc aac cct gag
Ser Leu Leu Ser Val Cys Gly Trp Ser Gln Thr Ile Asn Pro Glu
             80              85              90
gac gac acg gat cct ggc cat gct gac ctg gtc ctc tat atc act
Asp Asp Thr Asp Pro Gly His Ala Asp Leu Val Leu Tyr Ile Thr
                 95              100             105
agg ttt gac ctg gag ttg cct gat ggt aac cgg cag gtg cgg ggc
Arg Phe Asp Leu Glu Leu Pro Asp Gly Asn Arg Gln Val Arg Gly
             110             115             120
gtc acc cag ctg ggc ggt gcc tgc tcc cca acc tgg agc tgc ctc
Val Thr Gln Leu Gly Gly Ala Cys Ser Pro Thr Trp Ser Cys Leu
                 125             130             135
att acc gag gac act ggc ttc gac ctg gga gtc acc att gcc cat
Ile Thr Glu Asp Thr Gly Phe Asp Leu Gly Val Thr Ile Ala His
             140             145             150
gag att ggg cac agc ttc ggc ctg gag cac gac   (SEQ ID NO:6)
Glu Ile Gly His Ser Phe Gly Leu Glu His Asp   (SEQ ID NO:7)
                 155             160
``` brain
heart
skeletal muscle
colon (no mucosa)
thymus
spleen kidney
liver
small intestine
placenta
lung
peripheral blood leukocyte

FIG. 11 gctgcaggcg gcatcctaca cctggagctg ctggtggccg tgggccccga tgtcttccag
<u>Primer 1</u>
gctcaccaga aggacacaga gcgctatgtg ctcaccaacc tcaacatcgg ggcagaactg
                      <u>Primer 3</u>
cttcgggacc cgtccctggg ggctcagttt cgggtgcacc tggtgaagat ggtcattctg acagagcctg agggtgctcc aaatatcaca gcaaacctca cctcgtcct gctgagcgtc tgtgggtgga gccagaccat caaccctgag gacgacacgg atcctggcca tgctgacctg
                      <u>Primer 4</u>
gtcctctata tcactaggtt tgacctggag ttgcctgatg gtaaccggca ggtgcggggc gtcacccagc tgggcggtgc ctgctcccca acctggagct gcctcattac cgaggacact ggcttcgacc tgggagtcac cattgcccat gagattgggc acagcttcgg cctggagcac
                      <u>Primer 2</u>
gac (SEQ ID NO:6)

Primer 1
Sense : gctgcaggcg gcatcctaca cctggagctg (SEQ ID NO:9)
Antisense : cagctccagg tgtaggatgc cgcctgcagc (SEQ ID NO:49)

Primer 2
Sense : accattgccc atgagattgg g (SEQ ID NO:14)
Antisense : cccaatctca tgggcaatgg t (SEQ ID NO:50)

Primer 3
Sense : gcgctatgtg ctcaccaacc tcaacatcgg (SEQ ID NO:51)
Antisense : ccgatgttga ggttggtgag cacatagcgc (SEQ ID NO:52)

Primer 4
Sense : atcaaccctg aggacgacac (SEQ ID NO:53)
Antisense : gtgtcgtcct cagggttgat (SEQ ID NO:54)

FIG. 12
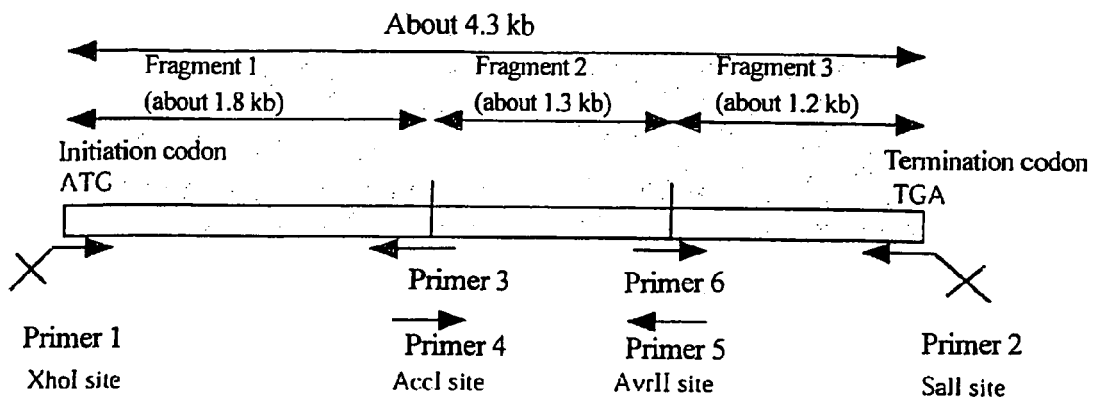
FIG. 13
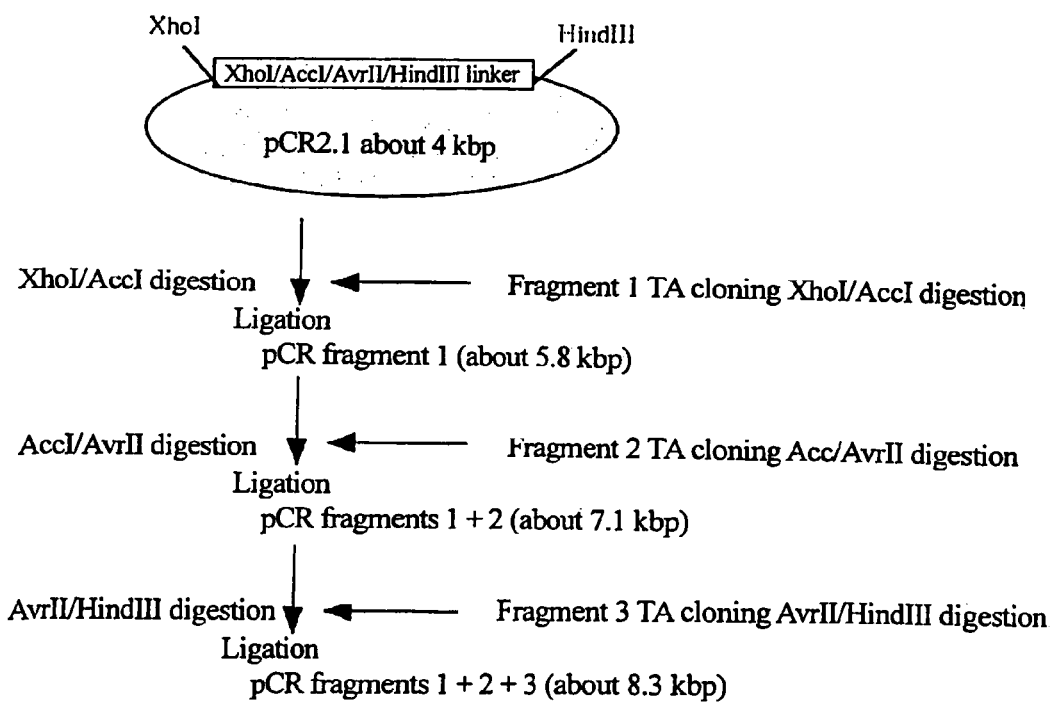
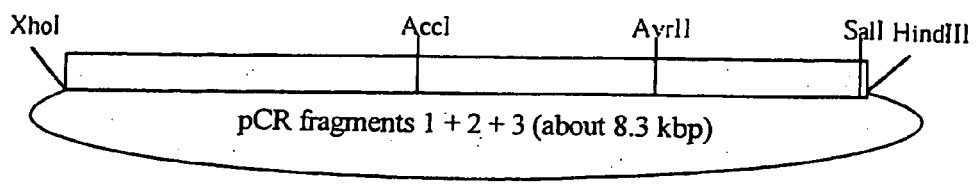

SEQUENCE LISTING

<160> NUMBER OF SEQ ID NOS: 48

<210> SEQ ID NO 1
<211> LENGTH: 5
<212> TYPE: PRT
<213> ORGANISM: Homo sapiens

<400> SEQUENCE: 1

Leu Leu Val Ala Val
1               5

<210> SEQ ID NO 2
<211> LENGTH: 14
<212> TYPE: PRT
<213> ORGANISM: Homo sapiens

<400> SEQUENCE: 2

Ala Ala Gly Gly Ile Leu His Leu Glu Leu Leu Val Ala Val
1               5                   10

<210> SEQ ID NO 3
<211> LENGTH: 161
<212> TYPE: PRT
<213> ORGANISM: Homo sapiens

<400> SEQUENCE: 3

Ala Ala Gly Gly Ile Leu His Leu Glu Leu Leu Val Ala Val Gly
1               5                   10                  15

Pro Asp Val Phe Gln Ala His Gln Lys Asp Thr Glu Arg Tyr Val
                20                  25                  30

Leu Thr Asn Leu Asn Ile Gly Ala Glu Leu Leu Arg Asp Pro Ser
                35                  40                  45

Leu Gly Ala Gln Phe Arg Val His Leu Val Lys Met Val Ile Leu
                50                  55                  60

Thr Glu Pro Glu Gly Ala Pro Asn Ile Thr Ala Asn Leu Thr Ser
                65                  70                  75

Ser Leu Leu Ser Val Cys Gly Trp Ser Gln Thr Ile Asn Pro Glu
                80                  85                  90

Asp Asp Thr Asp Pro Gly His Ala Asp Leu Val Leu Tyr Ile Thr
                95                  100                 105

Arg Phe Asp Leu Glu Leu Pro Asp Gly Asn Arg Gln Val Arg Gly
                110                 115                 120

Val Thr Gln Leu Gly Gly Ala Cys Ser Pro Thr Trp Ser Cys Leu
                125                 130                 135

Ile Thr Glu Asp Thr Gly Phe Asp Leu Gly Val Thr Ile Ala His
                140                 145                 150

Glu Ile Gly His Ser Phe Gly Leu Glu His Asp
                155                 160

<210> SEQ ID NO 4
<211> LENGTH: 15
<212> TYPE: DNA
<213> ORGANISM: Homo sapiens

<400> SEQUENCE: 4
ctgctggtgg ccgtg                                                    15

<210> SEQ ID NO 5
<211> LENGTH: 42
<212> TYPE: DNA
<213> ORGANISM: Homo sapiens

<400> SEQUENCE: 5
gctgcaggcg gcatcctaca cctggagctg ctggtggccg tg    42

<210> SEQ ID NO 6
<211> LENGTH: 483
<212> TYPE: DNA
<213> ORGANISM: Homo sapiens

<400> SEQUENCE: 6
gctgcaggcg gcatcctaca cctggagctg ctggtggccg tgggccccga tgtcttccag    60
gctcaccaga aggacacaga gcgctatgtg ctcaccaacc tcaacatcgg ggcagaactg    120
cttcgggacc cgtccctggg gctcagtttc gggtgcacc tggtgaagat ggtcattctg    180
acagagcctg agggtgctcc aaatatcaca gcaaacctca cctcgtccct gctgagcgtc    240
tgtgggtgga gccagaccat caaccctgag gacgacacgg atcctggcca tgctgacctg    300
gtcctctata tcactaggtt tgacctggag ttgcctgatg gtaaccggca ggtgcggggc    360
gtcacccagc tggcggtgc ctgctcccca acctggagct gcctcattac cgaggacact    420
ggcttcgacc tgggagtcac cattgcccat gagattgggc acagcttcgg cctggagcac    480
gac                                                                   483

<210> SEQ ID NO 7
<211> LENGTH: 161
<212> TYPE: PRT
<213> ORGANISM: Homo sapiens

<400> SEQUENCE: 7 gct gca ggc ggc atc cta cac ctg gag ctg ctg gtg gcc gtg ggc          45
Ala Ala Gly Gly Ile Leu His Leu Glu Leu Leu Val Ala Val Gly
1               5                   10                  15 ccc gat gtc ttc cag gct cac cag aag gac aca gag cgc tat gtg          90
Pro Asp Val Phe Gln Ala His Gln Lys Asp Thr Glu Arg Tyr Val
            20                  25                  30 ctc acc aac ctc aac atc ggg gca gaa ctg ctt cgg gac ccg tcc         135
Leu Thr Asn Leu Asn Ile Gly Ala Glu Leu Leu Arg Asp Pro Ser
        35                  40                  45 ctg ggg gct cag ttt cgg gtg cac ctg gtg aag atg gtc att ctg         180
Leu Gly Ala Gln Phe Arg Val His Leu Val Lys Met Val Ile Leu
    50                  55                  60 aca gag cct gag ggt gct cca aat atc aca gca aac ctc acc tcg         225
Thr Glu Pro Glu Gly Ala Pro Asn Ile Thr Ala Asn Leu Thr Ser
65                  70                  75 tcc ctg ctg agc gtc tgt ggg tgg agc cag acc atc aac cct gag         270
Ser Leu Leu Ser Val Cys Gly Trp Ser Gln Thr Ile Asn Pro Glu
            80                  85                  90 gac gac acg gat cct ggc cat gct gac ctg gtc ctc tat atc act         315
Asp Asp Thr Asp Pro Gly His Ala Asp Leu Val Leu Tyr Ile Thr
        95                  100                 105 agg ttt gac ctg gag ttg cct gat ggt aac cgg cag gtg cgg ggc         360
Arg Phe Asp Leu Glu Leu Pro Asp Gly Asn Arg Gln Val Arg Gly
    110                 115                 120 gtc acc cag ctg ggc ggt gcc tgc tcc cca acc tgg agc tgc ctc         405
Val Thr Gln Leu Gly Gly Ala Cys Ser Pro Thr Trp Ser Cys Leu
125                 130                 135

-continued

```
att acc gag gac act ggc ttc gac ctg gga gtc acc att gcc cat       450
Ile Thr Glu Asp Thr Gly Phe Asp Leu Gly Val Thr Ile Ala His
            140                 145                 150 gag att ggg cac agc ttc ggc ctg gag cac gac                       483
Glu Ile Gly His Ser Phe Gly Leu Glu His Asp
            155                 160
```

```
<210> SEQ ID NO 8
<211> LENGTH: 29
<212> TYPE: PRT
<213> ORGANISM: Homo sapiens

<400> SEQUENCE: 8

Ala Ala Gly Gly Ile Leu His Leu Glu Leu Leu Val Ala Val Gly
1               5                   10                  15

Pro Asp Val Phe Gln Ala His Gln Lys Asp Thr Arg Arg Tyr
            20                  25
```

```
<210> SEQ ID NO 9
<211> LENGTH: 30
<212> TYPE: DNA
<213> ORGANISM: Homo sapiens

<400> SEQUENCE: 9
gctgcaggcg gcatcctaca cctggagctg                                   30
```

```
<210> SEQ ID NO 10
<211> LENGTH: 21
<212> TYPE: DNA
<213> ORGANISM: Homo sapiens

<400> SEQUENCE: 10
cccaatctca tgggcaatgg t                                            21
```

```
<210> SEQ ID NO 11
<211> LENGTH: 21
<212> TYPE: DNA
<213> ORGANISM: Homo sapiens

<400> SEQUENCE: 11
cccaatctca tgggcaatgg t                                            21
```

```
<210> SEQ ID NO 12
<211> LENGTH: 30
<212> TYPE: DNA
<213> ORGANISM: Homo sapiens

<400> SEQUENCE: 12
ccgatgttga ggttggtgag cacatagcgc                                   30
```

```
<210> SEQ ID NO 13
<211> LENGTH: 20
<212> TYPE: DNA
<213> ORGANISM: Homo sapiens

<400> SEQUENCE: 13
gtgtcgtcct cagggttgat                                              20
```

```
<210> SEQ ID NO 14
<211> LENGTH: 21
<212> TYPE: DNA
<213> ORGANISM: Homo sapiens

<400> SEQUENCE: 14
```

```
accattgccc atgagattgg g                                          21

<210> SEQ ID NO 15
<211> LENGTH: 4950
<212> TYPE: DNA
<213> ORGANISM: Homo sapiens

<400> SEQUENCE: 15
aaccacgatg tctttggcac agcctctcat ctgtcagatg ggagcgggga ccccggagag    60
ggagtcagcc gaggtcctgg cattccttgt gaaccccgt ctgtgggttt ctggtccagt    120
gtcccttctc cagattagat ggcttaggcc tcctctaagg gggtgggcgt gcacatccgg   180
agagctgtct ggtgtgcagg actgggctgc aggttaccct gaactgcaac catcttagag   240
caaggcccag cttgcagcag gaggagctgc aggccgccca ccctagccac ggcccctgcc   300
ctggcaggaa gcttccaaga gtaaacactg cctaatcgtc ccgcccagta gtgagcaggc   360
ctgtcccatt ccatactgac cagattccca gtcaccaagg cccctctca ctccgctcca    420 ctcctcgggc tggctctcct gaggatgcac cagcgtcacc cccgggcaag atgccctccc   480
ctctgtgtgg ccggaatcct tgcctgtggc tttctcctgg gctgctgggg accctcccat   540
ttccagcaga gttgtcttca ggcttttggag ccacaggccg tgtcttctta cttgagccct   600
ggtgctccct taaaaggccg ccctccttcc cctggcttcc agaggcagag gcagaggcag   660
aggcgggctg caggcggcat cctacacctg gagctgctgg tggccgtggg ccccgatgtc   720
ttccaggctc accaggagga cacagagcgc tatgtgctca ccaacctcaa catcggggca   780
gaactgcttc gggacccgtc cctgggggct cagtttcggg tgcacctggt gaagatggtc   840
attctgacag agcctgaggg tgctccaaat atcacagcca acctcacctc gtccctgctg   900
agcgtctgtg ggtggagcca gaccatcaac cctgaggacg acacggatcc tggccatgct   960
gacctggtcc tctatatcac taggtttgac ctggagttgc ctgatggtaa ccggcaggtg  1020
cggggcgtca cccagctggg cgtgcctgc tccccaacct ggagctgcct cattaccgag  1080
gacactggct tcgacctggg agtcaccatt gcccatgaga ttgggcacag cttcggcctg  1140
gagcacgacg gcgcgcccgg cagcggctgc ggccccagcg acacgtgat ggcttcggac  1200 ggcgccgcgc ccgcgccgg cctcgcctgg tccccctgca gccgccggca gctgctgagc  1260
ctgctcagcg caggacgggc gcgctgcgtg tgggacccgc gcgggcctca acccgggtcc  1320
gcggggcacc cgccggatgc gcagcctggc ctctactaca cgccaacga gcagtgccgc  1380 gtggccttcg gccccaaggc tgtcgcctgc accttcgcca gggagcacct ggatatgtgc  1440
caggccctct cctgccacac agacccgctg gaccaaagca gctgcagccg cctcctcgtt  1500
cctctcctgg atgggacaga atgtggcgtg gagaagtggt gctccaaggg tcgctgccgc  1560
tccctggtgg agctgacccc catagcagca gtgcatgggc gctggtctag ctggggtccc  1620
cgaagtcctt gctcccgctc ctgcggagga ggtgtggtca ccaggaggcg cagtgcaac   1680 aaccccagac ctgcctttgg ggggcgtgca tgtgttggtg ctgacctcca ggccgagatg   1740
tgcaacactc aggcctgcga gaagacccag ctggagttca tgtcgcaaca gtgcgccagg   1800
accgacggcc agccgctgcg ctcctccct ggcggcgcct ccttctacca ctggggtgct   1860
gctgtaccac acagccaagg ggatgctctg tgcagacaca tgtgccgggc cattggcgag   1920
agcttcatca tgaagcgtgg agacagcttc ctcgatggga cccggtgtat gccaagtggc   1980
ccccgggagg acgggaccct gagcctgtgt gtgtcgggca gctgcaggac atttggctgt   2040
```

-continued

```
gatggtagga tggactccca gcaggtatgg gacaggtgcc aggtgtgtgg tgggacaac    2100
agcacgtgca gcccacggaa gggctctttc acagctggca gagcgagaga atatgtcacg   2160
tttctgacag ttaccccccaa cctgaccagt gtctacattg ccaaccacag gcctctcttc  2220
acacacttgg cggtgaggat cggagggcgc tatgtcgtgg ctgggaagat gagcatctcc   2280
cctaacacca cctaccccte cctcctggag gatggtcgtg tcgagtacag agtggccctc   2340
accgaggacc ggctgcccg cctggaggag atccgcatct ggggacccct ccaggaagat    2400
gctgacatcc aggtttacag gcggtatggc gaggagtatg gcaacctcac ccgcccagac   2460
atcaccttca cctacttcca gcctaagcca cggcaggcct gggtgtgggc cgctgtgcgt   2520
gggccctgct cggtgagctg tggggcaggg ctgcgctggg taaactacag ctgcctggac   2580
caggccagga aggagttggt ggagactgtc cagtgccaag ggagccagca gccaccagcg   2640
tggccagagg cctgcgtgct cgaaccctgc cctccctact gggcggtggg agacttcggc   2700
ccatgcagcg cctcctgtgg gggcggcctg cgggagcggc cagtgcgctg cgtggaggcc   2760
cagggcagcc tcctgaagac attgccccca gcccggtgca gagcaggggc ccagcagcca   2820
gctgtggcgc tggaaacctg caaccccag ccctgccctg ccaggtggga ggtgtcagag    2880
cccagctcat gcacatcagc tggtggagca ggcctggcct tggagaacga gacctgtgtg   2940
ccaggggcag atggcctgga ggctccagtg actgaggggc ctggctccgt agatgagaag   3000
ctgcctgccc ctgagccctg tgtcgggatg tcatgtcctc caggctgggg ccatctggat   3060
gccacctctg caggggagaa ggctccctcc ccatggggca gcatcaggac gggggctcaa   3120
gctgcacacg tgtggacccc tgcggcaggg tcgtgctccg tctcctgcgg gcgaggtctg   3180
atggagctgc gtttcctgtg catggactct gccctcaggg tgcctgtcca ggaagagctg   3240
tgtggcctgg caagcaagcc tgggagccgg cgggaggtct gccaggctgt cccgtgccct   3300
gctcggtggc agtacaagct ggcggcctgc agcgtgagct gtgggagagg ggtcgtgcgg   3360
aggatcctgt attgtgcccg ggcccatggg gaggacgatg tgaggagat cctgttggac     3420
acccagtgcc aggggctgcc tcgcccggaa ccccaggagg cctgcagcct ggagccctgc   3480
ccacctaggt ggaaagtcat gtcccttggc ccatgttcgg ccagctgtgg ccttggcact   3540
gctagacgct cggtggcctg tgtgcagctc gaccaaggcc aggacgtgga ggtgacgag    3600
gcggcctgtg cggcgctggt gcggcccgag gccagtgtcc cctgtctcat tgccgactgc   3660
acctaccgct ggcatgttgg cacctggatg gagtgctctg tttcctgtgg ggatggcatc   3720
cagcgccggc gtgacacctg cctcggaccc caggcccagg cgcctgtgcc agctgatttc   3780
tgccagcact tgcccaagcc ggtgactgtg cgtggctgct gggctgggcc ctgtgtggga  3840
cagggtacgc ccagcctggt gccccacgaa gaagccgctc tccaggacg gaccacagcc    3900
accctgctg gtgcctccct ggagtggtcc caggccggg gcctgctctt ctccccggct    3960
ccccagcctc ggcggctcct gcccgggccc caggaaaact cagtgcagtc cagtgcctgt   4020
ggcaggcagc accttgagcc aacaggaacc attgacatgc gaggcccagg gcaggcagac   4080
tgtgcagtgg ccattgggcg gccctcgg gaggtggtga ccctccgcgt ccttgagagt     4140
tctctcaact gcagtgcggg ggacatgttg ctgctttggg gccggctcac ctggaggaag   4200
atgtgcagga agctgttgga catgactttc agctccaaga ccaacacgct ggtggtgagg   4260
cagcgctgcg ggcggccagg aggtggggtg ctgctgcggt atgggagcca gcttgctcct   4320
gaaaaccttct acagagaatg tgacatgcag ctctttgggc cctggggtga atcgtgagc    4380
ccctcgctga gtccagccac gagtaatgca gggggctgcc ggctcttcat taatgtggct   4440
```

```
ccgcacgcac ggattgccat ccatgccctg gccaccaaca tgggcgctgg gaccgaggga    4500
gccaatgcca gctacatctt gatccgggac acccacagct tgaggaccac agcgttccat    4560
gggcagcagg tgctctactg ggagtcagag agcagccagg ctgagatgga gttcagcgag    4620
ggcttcctga aggctcaggc cagcctgcgg ggccagtact ggaccctcca atcatgggta    4680
ccggagatgc aggaccctca gtcctggaag ggaaaggaag gaacctgagg gtcattgaac    4740
atttgttccg tgtctggcca gccctggagg gttgacccct ggtctcagtg ctttccaatt    4800 cgaactttt  ccaatcttag gtatctactt tagagtcttc tccaatgtcc aaaaggctag    4860
ggggttggag gtggggactc tggaaaagca gccccattt  cctcgggtac aataaataa    4920 aacatgcagg ccaaaaaaaa aaaaaaaaa                                     4950
```

<210> SEQ ID NO 16
<211> LENGTH: 1353
<212> TYPE: PRT
<213> ORGANISM: Homo sapiens

<400> SEQUENCE: 16

```
gct gca ggc ggc atc cta cac ctg gag ctg ctg gtg gcc gtg ggc           45
Ala Ala Gly Gly Ile Leu His Leu Glu Leu Leu Val Ala Val Gly
1               5                   10                  15 ccc gat gtc ttc cag gct cac cag gag gac aca gag cgc tat gtg           90
Pro Asp Val Phe Gln Ala His Gln Glu Asp Thr Glu Arg Tyr Val
                20                  25                  30 ctc acc aac ctc aac atc ggg gca gaa ctg ctt cgg gac ccg tcc           135
Leu Thr Asn Leu Asn Ile Gly Ala Glu Leu Leu Arg Asp Pro Ser
            35                  40                  45 ctg ggg gct cag ttt cgg gtg cac ctg gtg aag atg gtc att ctg           180
Leu Gly Ala Gln Phe Arg Val His Leu Val Lys Met Val Ile Leu
        50                  55                  60 aca gag cct gag ggt gct cca aat atc aca gcc aac ctc acc tcg           225
Thr Glu Pro Glu Gly Ala Pro Asn Ile Thr Ala Asn Leu Thr Ser
65                  70                  75 tcc ctg ctg agc gtc tgt ggg tgg agc cag acc atc aac cct gag           270
Ser Leu Leu Ser Val Cys Gly Trp Ser Gln Thr Ile Asn Pro Glu
                80                  85                  90 gac gac acg gat cct ggc cat gct gac ctg gtc ctc tat atc act           315
Asp Asp Thr Asp Pro Gly His Ala Asp Leu Val Leu Tyr Ile Thr
                95                  100                 105 agg ttt gac ctg gag ttg cct gat ggt aac cgg cag gtg cgg ggc           360
Arg Phe Asp Leu Glu Leu Pro Asp Gly Asn Arg Gln Val Arg Gly
            110                 115                 120 gtc acc cag ctg ggc ggt gcc tgc tcc cca acc tgg agc tgc ctc           405
Val Thr Gln Leu Gly Gly Ala Cys Ser Pro Thr Trp Ser Cys Leu
        125                 130                 135 att acc gag gac act ggc ttc gac ctg gga gtc acc att gcc cat           450
Ile Thr Glu Asp Thr Gly Phe Asp Leu Gly Val Thr Ile Ala His
    140                 145                 150 gag att ggg cac agc ttc ggc ctg gag cac gac ggc gcg ccc ggc           495
Glu Ile Gly His Ser Phe Gly Leu Glu His Asp Gly Ala Pro Gly
                155                 160                 165 agc ggc tgc ggc ccc agc gga cac gtg atg gct tcg gac ggc gcc           540
Ser Gly Cys Gly Pro Ser Gly His Val Met Ala Ser Asp Gly Ala
            170                 175                 180 gcg ccc cgc gcc ggc ctc gcc tgg tcc ccc tgc agc cgc cgg cag           585
Ala Pro Arg Ala Gly Leu Ala Trp Ser Pro Cys Ser Arg Arg Gln
        185                 190                 195
```

```
                                                    -continued
ctg ctg agc ctg ctc agc gca gga cgg gcg cgc tgc gtg tgg gac     630
Leu Leu Ser Leu Leu Ser Ala Gly Arg Ala Arg Cys Val Trp Asp
            200                 205                 210 ccg ccg cgg cct caa ccc ggg tcc gcg ggg cac ccg gat gcg         675
Pro Pro Arg Pro Gln Pro Gly Ser Ala Gly His Pro Pro Asp Ala
            215                 220                 225 cag cct ggc ctc tac tac agc gcc aac gag cag tgc cgc gtg gcc     720
Gln Pro Gly Leu Tyr Tyr Ser Ala Asn Glu Gln Cys Arg Val Ala
            230                 235                 240 ttc ggc ccc aag gct gtc gcc tgc acc ttc gcc agg gag cac ctg     765
Phe Gly Pro Lys Ala Val Ala Cys Thr Phe Ala Arg Glu His Leu
            245                 250                 255 gat atg tgc cag gcc ctc tcc tgc cac aca gac ccg ctg gac caa     810
Asp Met Cys Gln Ala Leu Ser Cys His Thr Asp Pro Leu Asp Gln
            260                 265                 270 agc agc tgc agc cgc ctc ctc gtt cct ctc ctg gat ggg aca gaa     855
Ser Ser Cys Ser Arg Leu Leu Val Pro Leu Leu Asp Gly Thr Glu
            275                 280                 285 tgt ggc gtg gag aag tgg tgc tcc aag ggt cgc tgc cgc tcc ctg     900
Cys Gly Val Glu Lys Trp Cys Ser Lys Gly Arg Cys Arg Ser Leu
            290                 295                 300 gtg gag ctg acc ccc ata gca gca gtg cat ggg cgc tgg tct agc     945
Val Glu Leu Thr Pro Ile Ala Ala Val His Gly Arg Trp Ser Ser
            305                 310                 315 tgg ggt ccc cga agt cct tgc tcc cgc tcc tgc gga gga ggt gtg     990
Trp Gly Pro Arg Ser Pro Cys Ser Arg Ser Cys Gly Gly Gly Val
            320                 325                 330 gtc acc agg agg cgg cag tgc aac aac ccc aga cct gcc ttt ggg     1035
Val Thr Arg Arg Arg Gln Cys Asn Asn Pro Arg Pro Ala Phe Gly
            335                 340                 345 ggg cgt gca tgt gtt ggt gct gac ctc cag gcc gag atg tgc aac     1080
Gly Arg Ala Cys Val Gly Ala Asp Leu Gln Ala Glu Met Cys Asn
            350                 355                 360 act cag gcc tgc gag aag acc cag ctg gag ttc atg tcg caa cag     1125
Thr Gln Ala Cys Glu Lys Thr Gln Leu Glu Phe Met Ser Gln Gln
            365                 370                 375 tgc gcc agg acc gac ggc cag ccg ctg cgc tcc tcc cct ggc ggc     1170
Cys Ala Arg Thr Asp Gly Gln Pro Leu Arg Ser Ser Pro Gly Gly
            380                 385                 390 gcc tcc ttc tac cac tgg ggt gct gct gta cca cac agc caa ggg     1215
Ala Ser Phe Tyr His Trp Gly Ala Ala Val Pro His Ser Gln Gly
            395                 400                 405 gat gct ctg tgc aga cac atg tgc cgg gcc att ggc gag agc ttc     1260
Asp Ala Leu Cys Arg His Met Cys Arg Ala Ile Gly Glu Ser Phe
            410                 415                 420 atc atg aag cgt gga gac agc ttc ctc gat ggg acc cgg tgt atg     1305
Ile Met Lys Arg Gly Asp Ser Phe Leu Asp Gly Thr Arg Cys Met
            425                 430                 435 cca agt ggc ccc cgg gag gac ggg acc ctg agc ctg tgt gtg tcg     1350
Pro Ser Gly Pro Arg Glu Asp Gly Thr Leu Ser Leu Cys Val Ser
            440                 445                 450 ggc agc tgc agg aca ttt ggc tgt gat ggt agg atg gac tcc cag     1395
Gly Ser Cys Arg Thr Phe Gly Cys Asp Gly Arg Met Asp Ser Gln
            455                 460                 465 cag gta tgg gac agg tgc cag gtg tgt ggt ggg gac aac agc acg     1440
Gln Val Trp Asp Arg Cys Gln Val Cys Gly Gly Asp Asn Ser Thr
            470                 475                 480 tgc agc cca cgg aag ggc tct ttc aca gct ggc aga gcg aga gaa     1485
Cys Ser Pro Arg Lys Gly Ser Phe Thr Ala Gly Arg Ala Arg Glu
            485                 490                 495
```

-continued

| | |
|---|---|
| tat gtc acg ttt ctg aca gtt acc ccc aac ctg acc agt gtc tac<br>Tyr Val Thr Phe Leu Thr Val Thr Pro Asn Leu Thr Ser Val Tyr<br>500                     505                   510 | 1530 |
| att gcc aac cac agg cct ctc ttc aca cac ttg gcg gtg agg atc<br>Ile Ala Asn His Arg Pro Leu Phe Thr His Leu Ala Val Arg Ile<br>515                     520                   525 | 1575 |
| gga ggg cgc tat gtc gtg gct ggg aag atg agc atc tcc cct aac<br>Gly Gly Arg Tyr Val Val Ala Gly Lys Met Ser Ile Ser Pro Asn<br>530                     535                   540 | 1620 |
| acc acc tac ccc tcc ctc ctg gag gat ggt cgt gtc gag tac aga<br>Thr Thr Tyr Pro Ser Leu Leu Glu Asp Gly Arg Val Glu Tyr Arg<br>545                     550                   555 | 1665 |
| gtg gcc ctc acc gag gac cgg ctg ccc cgc ctg gag gag atc cgc<br>Val Ala Leu Thr Glu Asp Arg Leu Pro Arg Leu Glu Glu Ile Arg<br>560                     565                   570 | 1710 |
| atc tgg gga ccc ctc cag gaa gat gct gac atc cag gtt tac agg<br>Ile Trp Gly Pro Leu Gln Glu Asp Ala Asp Ile Gln Val Tyr Arg<br>575                     580                   585 | 1755 |
| cgg tat ggc gag gag tat ggc aac ctc acc cgc cca gac atc acc<br>Arg Tyr Gly Glu Glu Tyr Gly Asn Leu Thr Arg Pro Asp Ile Thr<br>590                     595                   600 | 1800 |
| ttc acc tac ttc cag cct aag cca cgg cag gcc tgg gtg tgg gcc<br>Phe Thr Tyr Phe Gln Pro Lys Pro Arg Gln Ala Trp Val Trp Ala<br>605                     610                   615 | 1845 |
| gct gtg cgt ggg ccc tgc tcg gtg agc tgt ggg gca ggg ctg cgc<br>Ala Val Arg Gly Pro Cys Ser Val Ser Cys Gly Ala Gly Leu Arg<br>620                     625                   630 | 1890 |
| tgg gta aac tac agc tgc ctg gac cag gcc agg aag gag ttg gtg<br>Trp Val Asn Tyr Ser Cys Leu Asp Gln Ala Arg Lys Glu Leu Val<br>635                     640                   645 | 1935 |
| gag act gtc cag tgc caa ggg agc cag cag cca cca gcg tgg cca<br>Glu Thr Val Gln Cys Gln Gly Ser Gln Gln Pro Pro Ala Trp Pro<br>650                     655                   660 | 1980 |
| gag gcc tgc gtg ctc gaa ccc tgc cct ccc tac tgg gcg gtg gga<br>Glu Ala Cys Val Leu Glu Pro Cys Pro Pro Tyr Trp Ala Val Gly<br>665                     670                   675 | 2025 |
| gac ttc ggc cca tgc agc gcc tcc tgt ggg ggc ggc ctg cgg gag<br>Asp Phe Gly Pro Cys Ser Ala Ser Cys Gly Gly Gly Leu Arg Glu<br>680                     685                   690 | 2070 |
| cgg cca gtg cgc tgc gtg gag gcc cag ggc agc ctc ctg aag aca<br>Arg Pro Val Arg Cys Val Glu Ala Gln Gly Ser Leu Leu Lys Thr<br>695                     700                   705 | 2115 |
| ttg ccc cca gcc cgg tgc aga gca ggg gcc cag cag cca gct gtg<br>Leu Pro Pro Ala Arg Cys Arg Ala Gly Ala Gln Gln Pro Ala Val<br>710                     715                   720 | 2160 |
| gcg ctg gaa acc tgc aac ccc cag ccc tgc cct gcc agg tgg gag<br>Ala Leu Glu Thr Cys Asn Pro Gln Pro Cys Pro Ala Arg Trp Glu<br>725                     730                   735 | 2205 |
| gtg tca gag ccc agc tca tgc aca tca gct ggt gga gca ggc ctg<br>Val Ser Glu Pro Ser Ser Cys Thr Ser Ala Gly Gly Ala Gly Leu<br>740                     745                   750 | 2250 |
| gcc ttg gag aac gag acc tgt gtg cca ggg gca gat ggc ctg gag<br>Ala Leu Glu Asn Glu Thr Cys Val Pro Gly Ala Asp Gly Leu Glu<br>755                     760                   765 | 2295 |
| gct cca gtg act gag ggg cct ggc tcc gta gat gag aag ctg cct<br>Ala Pro Val Thr Glu Gly Pro Gly Ser Val Asp Glu Lys Leu Pro<br>770                     775                   780 | 2340 |
| gcc cct gag ccc tgt gtc ggg atg tca tgt cct cca ggc tgg ggc<br>Ala Pro Glu Pro Cys Val Gly Met Ser Cys Pro Pro Gly Trp Gly | 2385 |

-continued

| | | | |
|---|---|---|---|
| | 785 | 790 | 795 | cat ctg gat gcc acc tct gca ggg gag aag gct ccc tcc cca tgg    2430
His Leu Asp Ala Thr Ser Ala Gly Glu Lys Ala Pro Ser Pro Trp
            800                 805                 810 ggc agc atc agg acg ggg gct caa gct gca cac gtg tgg acc cct    2475
Gly Ser Ile Arg Thr Gly Ala Gln Ala Ala His Val Trp Thr Pro
            815                 820                 825 gcg gca ggg tcg tgc tcc gtc tcc tgc ggg cga ggt ctg atg gag    2520
Ala Ala Gly Ser Cys Ser Val Ser Cys Gly Arg Gly Leu Met Glu
            830                 835                 840 ctg cgt ttc ctg tgc atg gac tct gcc ctc agg gtg cct gtc cag    2565
Leu Arg Phe Leu Cys Met Asp Ser Ala Leu Arg Val Pro Val Gln
            845                 850                 855 gaa gag ctg tgt ggc ctg gca agc aag cct ggg agc cgg cgg gag    2610
Glu Glu Leu Cys Gly Leu Ala Ser Lys Pro Gly Ser Arg Arg Glu
            860                 865                 870 gtc tgc cag gct gtc ccg tgc cct gct cgg tgg cag tac aag ctg    2655
Val Cys Gln Ala Val Pro Cys Pro Ala Arg Trp Gln Tyr Lys Leu
            875                 880                 885 gcg gcc tgc agc gtg agc tgt ggg aga ggg gtc gtg cgg agg atc    2700
Ala Ala Cys Ser Val Ser Cys Gly Arg Gly Val Val Arg Arg Ile
            890                 895                 900 ctg tat tgt gcc cgg gcc cat ggg gag gac gat ggt gag gag atc    2745
Leu Tyr Cys Ala Arg Ala His Gly Glu Asp Asp Gly Glu Glu Ile
            905                 910                 915 ctg ttg gac acc cag tgc cag ggg ctg cct cgc ccg gaa ccc cag    2790
Leu Leu Asp Thr Gln Cys Gln Gly Leu Pro Arg Pro Glu Pro Gln
            920                 925                 930 gag gcc tgc agc ctg gag ccc tgc cca cct agg tgg aaa gtc atg    2835
Glu Ala Cys Ser Leu Glu Pro Cys Pro Pro Arg Trp Lys Val Met
            935                 940                 945 tcc ctt ggc cca tgt tcg gcc agc tgt ggc ctt ggc act gct aga    2880
Ser Leu Gly Pro Cys Ser Ala Ser Cys Gly Leu Gly Thr Ala Arg
            950                 955                 960 cgc tcg gtg gcc tgt gtg cag ctc gac caa ggc cag gac gtg gag    2925
Arg Ser Val Ala Cys Val Gln Leu Asp Gln Gly Gln Asp Val Glu
            965                 970                 975 gtg gac gag gcg gcc tgt gcg gcg ctg gtg cgg ccc gag gcc agt    2970
Val Asp Glu Ala Ala Cys Ala Ala Leu Val Arg Pro Glu Ala Ser
            980                 985                 990 gtc ccc tgt ctc att gcc gac tgc acc tac cgc tgg cat gtt ggc    3015
Val Pro Cys Leu Ile Ala Asp Cys Thr Tyr Arg Trp His Val Gly
            995                 1000                1005 acc tgg atg gag tgc tct gtt tcc tgt ggg gat ggc atc cag cgc    3060
Thr Trp Met Glu Cys Ser Val Ser Cys Gly Asp Gly Ile Gln Arg
            1010                1015                1020 cgg cgt gac acc tgc ctc gga ccc cag gcc cag gcg cct gtg cca    3105
Arg Arg Asp Thr Cys Leu Gly Pro Gln Ala Gln Ala Pro Val Pro
            1025                1030                1035 gct gat ttc tgc cag cac ttg ccc aag ccg gtg act gtg cgt ggc    3150
Ala Asp Phe Cys Gln His Leu Pro Lys Pro Val Thr Val Arg Gly
            1040                1045                1050 tgc tgg gct ggg ccc tgt gtg gga cag ggt acg ccc agc ctg gtg    3195
Cys Trp Ala Gly Pro Cys Val Gly Gln Gly Thr Pro Ser Leu Val
            1055                1060                1065 ccc cac gaa gaa gcc gct gct cca gga cgg acc aca gcc acc cct    3240
Pro His Glu Glu Ala Ala Ala Pro Gly Arg Thr Thr Ala Thr Pro
            1070                1075                1080 gct ggt gcc tcc ctg gag tgg tcc cag gcc cgg ggc ctg ctc ttc    3285

```
Ala Gly Ala Ser Leu Glu Trp Ser Gln Ala Arg Gly Leu Leu Phe
            1085                1090                1095 tcc ccg gct ccc cag cct cgg cgg ctc ctg ccc ggg ccc cag gaa        3330
Ser Pro Ala Pro Gln Pro Arg Arg Leu Leu Pro Gly Pro Gln Glu
            1100                1105                1110 aac tca gtg cag tcc agt gcc tgt ggc agg cag cac ctt gag cca        3375
Asn Ser Val Gln Ser Ser Ala Cys Gly Arg Gln His Leu Glu Pro
            1115                1120                1125 aca gga acc att gac atg cga ggc cca ggg cag gca gac tgt gca        3420
Thr Gly Thr Ile Asp Met Arg Gly Pro Gly Gln Ala Asp Cys Ala
            1130                1135                1140 gtg gcc att ggg cgg ccc ctc ggg gag gtg gtg acc ctc cgc gtc        3465
Val Ala Ile Gly Arg Pro Leu Gly Glu Val Val Thr Leu Arg Val
            1145                1150                1155 ctt gag agt tct ctc aac tgc agt gcg ggg gac atg ttg ctg ctt        3510
Leu Glu Ser Ser Leu Asn Cys Ser Ala Gly Asp Met Leu Leu Leu
            1160                1165                1170 tgg ggc cgg ctc acc tgg agg aag atg tgc agg aag ctg ttg gac        3555
Trp Gly Arg Leu Thr Trp Arg Lys Met Cys Arg Lys Leu Leu Asp
            1175                1180                1185 atg act ttc agc tcc aag acc aac acg ctg gtg gtg agg cag cgc        3600
Met Thr Phe Ser Ser Lys Thr Asn Thr Leu Val Val Arg Gln Arg
            1190                1195                1200 tgc ggg cgg cca gga ggt ggg gtg ctg ctg cgg tat ggg agc cag        3645
Cys Gly Arg Pro Gly Gly Gly Val Leu Leu Arg Tyr Gly Ser Gln
            1205                1210                1215 ctt gct cct gaa acc ttc tac aga gaa tgt gac atg cag ctc ttt        3690
Leu Ala Pro Glu Thr Phe Tyr Arg Glu Cys Asp Met Gln Leu Phe
            1220                1225                1230 ggg ccc tgg ggt gaa atc gtg agc ccc tcg ctg agt cca gcc acg        3735
Gly Pro Trp Gly Glu Ile Val Ser Pro Ser Leu Ser Pro Ala Thr
            1235                1240                1245 agt aat gca ggg ggc tgc cgg ctc ttc att aat gtg gct ccg cac        3780
Ser Asn Ala Gly Gly Cys Arg Leu Phe Ile Asn Val Ala Pro His
            1250                1255                1260 gca cgg att gcc atc cat gcc ctg gcc acc aac atg ggc gct ggg        3825
Ala Arg Ile Ala Ile His Ala Leu Ala Thr Asn Met Gly Ala Gly
            1265                1270                1275 acc gag gga gcc aat gcc agc tac atc ttg atc cgg gac acc cac        3870
Thr Glu Gly Ala Asn Ala Ser Tyr Ile Leu Ile Arg Asp Thr His
            1280                1285                1290 agc ttg agg acc aca gcg ttc cat ggg cag cag gtg ctc tac tgg        3915
Ser Leu Arg Thr Thr Ala Phe His Gly Gln Gln Val Leu Tyr Trp
            1295                1300                1305 gag tca gag agc agc cag gct gag atg gag ttc agc gag ggc ttc        3960
Glu Ser Glu Ser Ser Gln Ala Glu Met Glu Phe Ser Glu Gly Phe
            1310                1315                1320 ctg aag gct cag gcc agc ctg cgg ggc cag tac tgg acc ctc caa        4005
Leu Lys Ala Gln Ala Ser Leu Arg Gly Gln Tyr Trp Thr Leu Gln
            1325                1330                1335 tca tgg gta ccg gag atg cag gac cct cag tcc tgg aag gga aag        4050
Ser Trp Val Pro Glu Met Gln Asp Pro Gln Ser Trp Lys Gly Lys
            1340                1345                1350 gaa gga acc                                                        4059
Glu Gly Thr <210> SEQ ID NO 17
<211> LENGTH: 1297
<212> TYPE: PRT
<213> ORGANISM: Homo sapiens
```

<400> SEQUENCE: 17

```
gct gca ggc ggc atc cta cac ctg gag ctg ctg gtg gcc gtg ggc         45
Ala Ala Gly Gly Ile Leu His Leu Glu Leu Leu Val Ala Val Gly
 1               5                  10                  15 ccc gat gtc ttc cag gct cac cag gag gac aca gag cgc tat gtg         90
Pro Asp Val Phe Gln Ala His Gln Glu Asp Thr Glu Arg Tyr Val
            20                  25                  30 ctc acc aac ctc aac atc ggg gca gaa ctg ctt cgg gac ccg tcc        135
Leu Thr Asn Leu Asn Ile Gly Ala Glu Leu Leu Arg Asp Pro Ser
        35                  40                  45 ctg ggg gct cag ttt cgg gtg cac ctg gtg aag atg gtc att ctg        180
Leu Gly Ala Gln Phe Arg Val His Leu Val Lys Met Val Ile Leu
    50                  55                  60 aca gag cct gag ggt gct cca aat atc aca gcc aac ctc acc tcg        225
Thr Glu Pro Glu Gly Ala Pro Asn Ile Thr Ala Asn Leu Thr Ser
65                  70                  75 tcc ctg ctg agc gtc tgt ggg tgg agc cag acc atc aac cct gag        270
Ser Leu Leu Ser Val Cys Gly Trp Ser Gln Thr Ile Asn Pro Glu
            80                  85                  90 gac gac acg gat cct ggc cat gct gac ctg gtc ctc tat atc act        315
Asp Asp Thr Asp Pro Gly His Ala Asp Leu Val Leu Tyr Ile Thr
        95                 100                 105 agg ttt gac ctg gag ttg cct gat ggt aac cgg cag gtg cgg ggc        360
Arg Phe Asp Leu Glu Leu Pro Asp Gly Asn Arg Gln Val Arg Gly
    110                 115                 120 gtc acc cag ctg ggc ggt gcc tgc tcc cca acc tgg agc tgc ctc        405
Val Thr Gln Leu Gly Gly Ala Cys Ser Pro Thr Trp Ser Cys Leu
125                 130                 135 att acc gag gac act ggc ttc gac ctg gga gtc acc att gcc cat        450
Ile Thr Glu Asp Thr Gly Phe Asp Leu Gly Val Thr Ile Ala His
            140                 145                 150 gag att ggg cac agc ttc ggc ctg gag cac gac ggc gcg ccc ggc        495
Glu Ile Gly His Ser Phe Gly Leu Glu His Asp Gly Ala Pro Gly
        155                 160                 165 agc ggc tgc ggg ccc agc gga cac gtg atg gct tcg gac ggc gcc        540
Ser Gly Cys Gly Pro Ser Gly His Val Met Ala Ser Asp Gly Ala
    170                 175                 180 gcg ccc cgc gcc ggc ctc gcc tgg tcc ccc tgc agc cgc cgg cag        585
Ala Pro Arg Ala Gly Leu Ala Trp Ser Pro Cys Ser Arg Arg Gln
185                 190                 195 ctg ctg agc ctc ctc agc gca gga cgg gcg cgc tgc gtg tgg gac        630
Leu Leu Ser Leu Leu Ser Ala Gly Arg Ala Arg Cys Val Trp Asp
            200                 205                 210 ccg ccg cgg cct caa ccc ggg tcc gcg ggg cac ccg ccg gat gcg        675
Pro Pro Arg Pro Gln Pro Gly Ser Ala Gly His Pro Pro Asp Ala
        215                 220                 225 cag cct ggc ctc tac tac agc gcc aac gag cag tgc cgc gtg gcc        720
Gln Pro Gly Leu Tyr Tyr Ser Ala Asn Glu Gln Cys Arg Val Ala
    230                 235                 240 ttc ggc ccc aag gct gtc gcc tgc acc ttc gcc agg gag cac ctg        765
Phe Gly Pro Lys Ala Val Ala Cys Thr Phe Ala Arg Glu His Leu
245                 250                 255 gat atg tgc cag gcc ctc tcc tgc cac aca gac ccg ctg gac caa        810
Asp Met Cys Gln Ala Leu Ser Cys His Thr Asp Pro Leu Asp Gln
            260                 265                 270 agc agc tgc agc cgc ctc ctc gtt cct ctc ctg gat ggg aca gaa        855
Ser Ser Cys Ser Arg Leu Leu Val Pro Leu Leu Asp Gly Thr Glu
        275                 280                 285
```

| | |
|---|---|
| tgt ggc gtg gag aag tgg tgc tcc aag ggt cgc tgc cgc tcc ctg<br>Cys Gly Val Glu Lys Trp Cys Ser Lys Gly Arg Cys Arg Ser Leu<br>290                             295                        300 | 900 |
| gtg gag ctg acc ccc ata gca gca gtg cat ggg cgc tgg tct agc<br>Val Glu Leu Thr Pro Ile Ala Ala Val His Gly Arg Trp Ser Ser<br>305                             310                        315 | 945 |
| tgg ggt ccc cga agt cct tgc tcc cgc tcc tgc gga gga ggt gtg<br>Trp Gly Pro Arg Ser Pro Cys Ser Arg Ser Cys Gly Gly Gly Val<br>320                             325                        330 | 990 |
| gtc acc agg agg cgg cag tgc aac aac ccc aga cct gcc ttt ggg<br>Val Thr Arg Arg Arg Gln Cys Asn Asn Pro Arg Pro Ala Phe Gly<br>335                             340                        345 | 1035 |
| ggg cgt gca tgt gtt ggt gct gac ctc cag gcc gag atg tgc aac<br>Gly Arg Ala Cys Val Gly Ala Asp Leu Gln Ala Glu Met Cys Asn<br>350                             355                        360 | 1080 |
| act cag gcc tgc gag aag acc cag ctg gag ttc atg tcg caa cag<br>Thr Gln Ala Cys Glu Lys Thr Gln Leu Glu Phe Met Ser Gln Gln<br>365                             370                        375 | 1125 |
| tgc gcc agg acc gac ggc cag ccg ctg cgc tcc tcc cct ggc ggc<br>Cys Ala Arg Thr Asp Gly Gln Pro Leu Arg Ser Ser Pro Gly Gly<br>380                             385                        390 | 1170 |
| gcc tcc ttc tac cac tgg ggt gct gct gta cca cac agc caa ggg<br>Ala Ser Phe Tyr His Trp Gly Ala Ala Val Pro His Ser Gln Gly<br>395                             400                        405 | 1215 |
| gat gct ctg tgc aga cac atg tgc cgg gcc att ggc gag agc ttc<br>Asp Ala Leu Cys Arg His Met Cys Arg Ala Ile Gly Glu Ser Phe<br>410                             415                        420 | 1260 |
| atc atg aag cgt gga gac agc ttc ctc gat ggg acc cgg tgt atg<br>Ile Met Lys Arg Gly Asp Ser Phe Leu Asp Gly Thr Arg Cys Met<br>425                             430                        435 | 1305 |
| cca agt ggc ccc cgg gag gac ggg acc ctg agc ctg tgt gtg tcg<br>Pro Ser Gly Pro Arg Glu Asp Gly Thr Leu Ser Leu Cys Val Ser<br>440                             445                        450 | 1350 |
| ggc agc tgc agg aca ttt ggc tgt gat ggt agg atg gac tcc cag<br>Gly Ser Cys Arg Thr Phe Gly Cys Asp Gly Arg Met Asp Ser Gln<br>455                             460                        465 | 1395 |
| cag gta tgg gac agg tgc cag gtg tgt ggt ggg gac aac agc acg<br>Gln Val Trp Asp Arg Cys Gln Val Cys Gly Gly Asp Asn Ser Thr<br>470                             475                        480 | 1440 |
| tgc agc cca cgg aag ggc tct ttc aca gct ggc aga gcg aga gaa<br>Cys Ser Pro Arg Lys Gly Ser Phe Thr Ala Gly Arg Ala Arg Glu<br>485                             490                        495 | 1485 |
| tat gtc acg ttt ctg aca gtt acc ccc aac ctg acc agt gtc tac<br>Tyr Val Thr Phe Leu Thr Val Thr Pro Asn Leu Thr Ser Val Tyr<br>500                             505                        510 | 1530 |
| att gcc aac cac agg cct ctc ttc aca cac ttg gcg gtg agg atc<br>Ile Ala Asn His Arg Pro Leu Phe Thr His Leu Ala Val Arg Ile<br>515                             520                        525 | 1575 |
| gga ggg cgc tat gtc gtg gct ggg aag atg agc atc tcc cct aac<br>Gly Gly Arg Tyr Val Val Ala Gly Lys Met Ser Ile Ser Pro Asn<br>530                             535                        540 | 1620 |
| acc acc tac ccc tcc ctc ctg gag gat ggt cgt gtc gag tac aga<br>Thr Thr Tyr Pro Ser Leu Leu Glu Asp Gly Arg Val Glu Tyr Arg<br>545                             550                        555 | 1665 |
| gtg gcc ctc acc gag gac cgg ctg ccc cgc ctg gag gag atc cgc<br>Val Ala Leu Thr Glu Asp Arg Leu Pro Arg Leu Glu Glu Ile Arg<br>560                             565                        570 | 1710 |
| atc tgg gga ccc ctc cag gaa gat gct gac atc cag gtt tac agg<br>Ile Trp Gly Pro Leu Gln Glu Asp Ala Asp Ile Gln Val Tyr Arg<br>575                             580                        585 | 1755 |

-continued

| | |
|---|---|
| cgg tat ggc gag gag tat ggc aac ctc acc cgc cca gac atc acc<br>Arg Tyr Gly Glu Glu Tyr Gly Asn Leu Thr Arg Pro Asp Ile Thr<br>590                          595                         600 | 1800 |
| ttc acc tac ttc cag cct aag cca cgg cag gcc tgg gtg tgg gcc<br>Phe Thr Tyr Phe Gln Pro Lys Pro Arg Gln Ala Trp Val Trp Ala<br>605                         610                        615 | 1845 |
| gct gtg cgt ggg ccc tgc tcg gtg agc tgt ggg gca ggg ctg cgc<br>Ala Val Arg Gly Pro Cys Ser Val Ser Cys Gly Ala Gly Leu Arg<br>620                         625                        630 | 1890 |
| tgg gta aac tac agc tgc ctg gac cag gcc agg aag gag ttg gtg<br>Trp Val Asn Tyr Ser Cys Leu Asp Gln Ala Arg Lys Glu Leu Val<br>635                         640                        645 | 1935 |
| gag act gtc cag tgc caa ggg agc cag cag cca cca gcg tgg cca<br>Glu Thr Val Gln Cys Gln Gly Ser Gln Gln Pro Pro Ala Trp Pro<br>650                         655                        660 | 1980 |
| gag gcc tgc gtg ctc gaa ccc tgc cct ccc tac tgg gcg gtg gga<br>Glu Ala Cys Val Leu Glu Pro Cys Pro Pro Tyr Trp Ala Val Gly<br>665                         670                        675 | 2025 |
| gac ttc ggc cca tgc agc gcc tcc tgt ggg ggc ggc ctg cgg gag<br>Asp Phe Gly Pro Cys Ser Ala Ser Cys Gly Gly Gly Leu Arg Glu<br>680                         685                        690 | 2070 |
| cgg cca gtg cgc tgc gtg gag gcc cag ggc agc ctc ctg aag aca<br>Arg Pro Val Arg Cys Val Glu Ala Gln Gly Ser Leu Leu Lys Thr<br>695                         700                        705 | 2115 |
| ttg ccc cca gcc cgg tgc aga gca ggg gcc cag cag cca gct gtg<br>Leu Pro Pro Ala Arg Cys Arg Ala Gly Ala Gln Gln Pro Ala Val<br>710                         715                        720 | 2160 |
| gcg ctg gaa acc tgc aac ccc cag ccc tgc cct gcc agg tgg gag<br>Ala Leu Glu Thr Cys Asn Pro Gln Pro Cys Pro Ala Arg Trp Glu<br>725                         730                        735 | 2205 |
| gtg tca gag ccc agc tca tgc aca tca gct ggt gga gca ggc ctg<br>Val Ser Glu Pro Ser Ser Cys Thr Ser Ala Gly Gly Ala Gly Leu<br>740                         745                        750 | 2250 |
| gcc ttg gag aac gag acc tgt gtg cca ggg gca gat ggc ctg gag<br>Ala Leu Glu Asn Glu Thr Cys Val Pro Gly Ala Asp Gly Leu Glu<br>755                         760                        765 | 2295 |
| gct cca gtg act gag ggg cct ggc tcc gta gat gag aag ctg cct<br>Ala Pro Val Thr Glu Gly Pro Gly Ser Val Asp Glu Lys Leu Pro<br>770                         775                        780 | 2340 |
| gcc cct gag ccc tgt gtc ggg atg tca tgt cct cca ggc tgg ggc<br>Ala Pro Glu Pro Cys Val Gly Met Ser Cys Pro Pro Gly Trp Gly<br>785                         790                        795 | 2385 |
| cat ctg gat gcc acc tct gca ggg gag aag gct ccc tcc cca tgg<br>His Leu Asp Ala Thr Ser Ala Gly Glu Lys Ala Pro Ser Pro Trp<br>800                         805                        810 | 2430 |
| ggc agc atc agg acg ggg gct caa gct gca cac gtg tgg acc cct<br>Gly Ser Ile Arg Thr Gly Ala Gln Ala Ala His Val Trp Thr Pro<br>815                         820                        825 | 2475 |
| gcg gca ggg tcg tgc tcc gtc tcc tgc ggg cga ggt ctg atg gag<br>Ala Ala Gly Ser Cys Ser Val Ser Cys Gly Arg Gly Leu Met Glu<br>830                         835                        840 | 2520 |
| ctg cgt ttc ctg tgc atg gac tct gcc ctc agg gtg cct gtc cag<br>Leu Arg Phe Leu Cys Met Asp Ser Ala Leu Arg Val Pro Val Gln<br>845                         850                        855 | 2565 |
| gaa gag ctg tgt ggc ctg gca agc aag cct ggg agc cgg cgg gag<br>Glu Glu Leu Cys Gly Leu Ala Ser Lys Pro Gly Ser Arg Arg Glu<br>860                         865                        870 | 2610 |
| gtc tgc cag gct gtc ccg tgc cct gct cgg tgg cag tac aag ctg<br>Val Cys Gln Ala Val Pro Cys Pro Ala Arg Trp Gln Tyr Lys Leu | 2655 |

```
                             -continued
              875                 880                 885
gcg gcc tgc agc gtg agc tgt ggg aga ggg gtc gtg cgg agg atc         2700
Ala Ala Cys Ser Val Ser Cys Gly Arg Gly Val Val Arg Arg Ile
                890                 895                 900 ctg tat tgt gcc cgg gcc cat ggg gag gac gat ggt gag gag atc         2745
Leu Tyr Cys Ala Arg Ala His Gly Glu Asp Asp Gly Glu Glu Ile
                905                 910                 915 ctg ttg gac acc cag tgc cag ggg ctg cct cgc ccg gaa ccc cag         2790
Leu Leu Asp Thr Gln Cys Gln Gly Leu Pro Arg Pro Glu Pro Gln
                920                 925                 930 gag gcc tgc agc ctg gag ccc tgc cca cct agg tgg aaa gtc atg         2835
Glu Ala Cys Ser Leu Glu Pro Cys Pro Pro Arg Trp Lys Val Met
                935                 940                 945 tcc ctt ggc cca tgt tcg gcc agc tgt ggc ctt ggc act gct aga         2880
Ser Leu Gly Pro Cys Ser Ala Ser Cys Gly Leu Gly Thr Ala Arg
                950                 955                 960 cgc tcg gtg gcc tgt gtg cag ctc gac caa ggc cag gac gtg gag         2925
Arg Ser Val Ala Cys Val Gln Leu Asp Gln Gly Gln Asp Val Glu
                965                 970                 975 gtg gac gag gcg gcc tgt gcg gcg ctg gtg cgg ccc gag gcc agt         2970
Val Asp Glu Ala Ala Cys Ala Ala Leu Val Arg Pro Glu Ala Ser
                980                 985                 990 gtc ccc tgt ctc att gcc gac tgc acc tac cgc tgg cat gtt ggc         3015
Val Pro Cys Leu Ile Ala Asp Cys Thr Tyr Arg Trp His Val Gly
                995                 1000                1005 acc tgg atg gag tgc tct gtt tcc tgt ggg gat ggc atc cag cgc         3060
Thr Trp Met Glu Cys Ser Val Ser Cys Gly Asp Gly Ile Gln Arg
                1010                1015                1020 cgg cgt gac acc tgc ctc gga ccc cag gcc cag gcg cct gtg cca         3105
Arg Arg Asp Thr Cys Leu Gly Pro Gln Ala Gln Ala Pro Val Pro
                1025                1030                1035 gct gat ttc tgc cag cac ttg ccc aag ccg gtg act gtg cgt ggc         3150
Ala Asp Phe Cys Gln His Leu Pro Lys Pro Val Thr Val Arg Gly
                1040                1045                1050 tgc tgg gct ggg ccc tgt gtg gga cag ggt gcc tgt ggc agg cag         3195
Cys Trp Ala Gly Pro Cys Val Gly Gln Gly Ala Cys Gly Arg Gln
                1055                1060                1065 cac ctt gag cca aca gga acc att gac atg cga ggc cca ggg cag         3240
His Leu Glu Pro Thr Gly Thr Ile Asp Met Arg Gly Pro Gly Gln
                1070                1075                1080 gca gac tgt gca gtg gcc att ggg cgg ccc ctc ggg gag gtg gtg         3285
Ala Asp Cys Ala Val Ala Ile Gly Arg Pro Leu Gly Glu Val Val
                1085                1090                1095 acc ctc cgc gtc ctt gag agt tct ctc aac tgc agt gcg ggg gac         3330
Thr Leu Arg Val Leu Glu Ser Ser Leu Asn Cys Ser Ala Gly Asp
                1100                1105                1110 atg ttg ctg ctt tgg ggc cgg ctc acc tgg agg aag atg tgc agg         3375
Met Leu Leu Leu Trp Gly Arg Leu Thr Trp Arg Lys Met Cys Arg
                1115                1120                1125 aag ctg ttg gac atg act ttc agc tcc aag acc aac acg ctg gtg         3420
Lys Leu Leu Asp Met Thr Phe Ser Ser Lys Thr Asn Thr Leu Val
                1130                1135                1140 gtg agg cag cgc tgc ggg cgg cca gga ggt ggg gtg ctg ctg cgg         3465
Val Arg Gln Arg Cys Gly Arg Pro Gly Gly Gly Val Leu Leu Arg
                1145                1150                1155 tat ggg agc cag ctt gct cct gaa acc ttc tac aga gaa tgt gac         3510
Tyr Gly Ser Gln Leu Ala Pro Glu Thr Phe Tyr Arg Glu Cys Asp
                1160                1165                1170 atg cag ctc ttt ggg ccc tgg ggt gaa atc gtg agc ccc tcg ctg         3555
```

```
Met Gln Leu Phe Gly Pro Trp Gly Glu Ile Val Ser Pro Ser Leu
                1175                1180                1185 agt cca gcc acg agt aat gca ggg ggc tgc cgg ctc ttc att aat       3600
Ser Pro Ala Thr Ser Asn Ala Gly Gly Cys Arg Leu Phe Ile Asn
        1190                1195                1200 gtg gct ccg cac gca cgg att gcc atc cat gcc ctg gcc acc aac       3645
Val Ala Pro His Ala Arg Ile Ala Ile His Ala Leu Ala Thr Asn
        1205                1210                1215 atg ggc gct ggg acc gag gga gcc aat gcc agc tac atc ttg atc       3690
Met Gly Ala Gly Thr Glu Gly Ala Asn Ala Ser Tyr Ile Leu Ile
        1220                1225                1230 cgg gac acc cac agc ttg agg acc aca gcg ttc cat ggg cag cag       3735
Arg Asp Thr His Ser Leu Arg Thr Thr Ala Phe His Gly Gln Gln
        1235                1240                1245 gtg ctc tac tgg gag tca gag agc agc cag gct gag atg gag ttc       3780
Val Leu Tyr Trp Glu Ser Glu Ser Ser Gln Ala Glu Met Glu Phe
        1250                1255                1260 agc gag ggc ttc ctg aag gct cag gcc agc ctg cgg ggc cag tac       3825
Ser Glu Gly Phe Leu Lys Ala Gln Ala Ser Leu Arg Gly Gln Tyr
        1265                1270                1275 tgg acc ctc caa tca tgg gta ccg gag atg cag gac cct cag tcc       3870
Trp Thr Leu Gln Ser Trp Val Pro Glu Met Gln Asp Pro Gln Ser
        1280                1285                1290 tgg aag gga aag gaa gga acc                                       3891
Trp Lys Gly Lys Glu Gly Thr
        1295

<210> SEQ ID NO 18
<211> LENGTH: 1378
<212> TYPE: PRT
<213> ORGANISM: Homo sapiens

<400> SEQUENCE: 18 gct gca ggc ggc atc cta cac ctg gag ctg ctg gtg gcc gtg ggc        45
Ala Ala Gly Gly Ile Leu His Leu Glu Leu Leu Val Ala Val Gly
1               5                   10                  15 ccc gat gtc ttc cag gct cac cag gag gac aca gag cgc tat gtg        90
Pro Asp Val Phe Gln Ala His Gln Glu Asp Thr Glu Arg Tyr Val
                20                  25                  30 ctc acc aac ctc aac atc ggg gca gaa ctg ctt cgg gac ccg tcc       135
Leu Thr Asn Leu Asn Ile Gly Ala Glu Leu Leu Arg Asp Pro Ser
                35                  40                  45 ctg ggg gct cag ttt cgg gtg cac ctg gtg aag atg gtc att ctg       180
Leu Gly Ala Gln Phe Arg Val His Leu Val Lys Met Val Ile Leu
            50                  55                  60 aca gag cct gag ggt gct cca aat atc aca gcc aac ctc acc tcg       225
Thr Glu Pro Glu Gly Ala Pro Asn Ile Thr Ala Asn Leu Thr Ser
        65                  70                  75 tcc ctg ctg agc gtc tgt ggg tgg agc cag acc atc aac cct gag       270
Ser Leu Leu Ser Val Cys Gly Trp Ser Gln Thr Ile Asn Pro Glu
        80                  85                  90 gac gac acg gat cct ggc cat gct gac ctg gtc ctc tat atc act       315
Asp Asp Thr Asp Pro Gly His Ala Asp Leu Val Leu Tyr Ile Thr
        95                  100                 105 agg ttt gac ctg gag ttg cct gat ggt aac cgg cag gtg cgg ggc       360
Arg Phe Asp Leu Glu Leu Pro Asp Gly Asn Arg Gln Val Arg Gly
        110                 115                 120 gtc acc cag ctg ggc ggt gcc tgc tcc cca acc tgg agc tgc ctc       405
Val Thr Gln Leu Gly Gly Ala Cys Ser Pro Thr Trp Ser Cys Leu
        125                 130                 135
```

-continued

```
att acc gag gac act ggc ttc gac ctg gga gtc acc att gcc cat         450
Ile Thr Glu Asp Thr Gly Phe Asp Leu Gly Val Thr Ile Ala His
            140                 145                 150 gag att ggg cac agc ttc ggc ctg gag cac gac ggc gcg ccc ggc         495
Glu Ile Gly His Ser Phe Gly Leu Glu His Asp Gly Ala Pro Gly
            155                 160                 165 agc ggc tgc ggc ccc agc gga cac gtg atg gct tcg gac ggc gcc         540
Ser Gly Cys Gly Pro Ser Gly His Val Met Ala Ser Asp Gly Ala
            170                 175                 180 gcg ccc cgc gcc ggc ctc gcc tgg tcc ccc tgc agc cgc cgg cag         585
Ala Pro Arg Ala Gly Leu Ala Trp Ser Pro Cys Ser Arg Arg Gln
            185                 190                 195 ctg ctg agc ctg ctc agg acg ggc gcg ctg cgt gtg gga ccc gcc         630
Leu Leu Ser Leu Leu Arg Thr Gly Ala Leu Arg Val Gly Pro Ala
            200                 205                 210 gcg gcc tca acc cgg gtc cgc ggg gca ccc gcc gga tgc gca gcc         675
Ala Ala Ser Thr Arg Val Arg Gly Ala Pro Ala Gly Cys Ala Ala
            215                 220                 225 tgg cct cta cta cag cgc caa cga gca gtg ccg cgt ggc ctt cgg         720
Trp Pro Leu Leu Gln Arg Gln Arg Ala Val Pro Arg Gly Leu Arg
            230                 235                 240 ccc caa ggc tgt cgc ctg cac ctt cgc cag gga gca cct ggt gag         765
Pro Gln Gly Cys Arg Leu His Leu Arg Gln Gly Ala Pro Gly Glu
            245                 250                 255 tct gcc ggc ggt ggc ctg gga ttg gct gtg agg tcc ctc cgc atc         810
Ser Ala Gly Gly Gly Leu Gly Leu Ala Val Arg Ser Leu Arg Ile
            260                 265                 270 acc cag ctc acg tcc ccc caa acg tgc atg gat atg tgc cag gcc         855
Thr Gln Leu Thr Ser Pro Gln Thr Cys Met Asp Met Cys Gln Ala
            275                 280                 285 ctc tcc tgc cac aca gac ccg ctg gac caa agc agc tgc agc cgc         900
Leu Ser Cys His Thr Asp Pro Leu Asp Gln Ser Ser Cys Ser Arg
            290                 295                 300 ctc ctc gtt cct ctc ctg gat ggg aca gaa tgt ggc gtg gag aag         945
Leu Leu Val Pro Leu Leu Asp Gly Thr Glu Cys Gly Val Glu Lys
            305                 310                 315 tgg tgc tcc aag ggt cgc tgc cgc tcc ctg gtg gag ctg acc ccc         990
Trp Cys Ser Lys Gly Arg Cys Arg Ser Leu Val Glu Leu Thr Pro
            320                 325                 330 ata gca gca gtg cat ggg cgc tgg tct agc tgg ggt ccc cga agt        1035
Ile Ala Ala Val His Gly Arg Trp Ser Ser Trp Gly Pro Arg Ser
            335                 340                 345 cct tgc tcc cgc tcc tgc gga gga ggt gtg gtc acc agg agg cgg        1080
Pro Cys Ser Arg Ser Cys Gly Gly Gly Val Val Thr Arg Arg Arg
            350                 355                 360 cag tgc aac aac ccc aga cct gcc ttt ggg ggg cgt gca tgt gtt        1125
Gln Cys Asn Asn Pro Arg Pro Ala Phe Gly Gly Arg Ala Cys Val
            365                 370                 375 ggt gct gac ctc cag gcc gag atg tgc aac act cag gcc tgc gag        1170
Gly Ala Asp Leu Gln Ala Glu Met Cys Asn Thr Gln Ala Cys Glu
            380                 385                 390 aag acc cag ctg gag ttc atg tcg caa cag tgc gcc agg acc gac        1215
Lys Thr Gln Leu Glu Phe Met Ser Gln Gln Cys Ala Arg Thr Asp
            395                 400                 405 ggc cag ccg ctg cgc tcc tcc cct ggc ggc gcc tcc ttc tac cac        1260
Gly Gln Pro Leu Arg Ser Ser Pro Gly Gly Ala Ser Phe Tyr His
            410                 415                 420 tgg ggt gct gct gta cca cac agc caa ggg gat gct ctg tgc aga        1305
Trp Gly Ala Ala Val Pro His Ser Gln Gly Asp Ala Leu Cys Arg
            425                 430                 435
```

-continued

```
cac atg tgc cgg gcc att ggc gag agc ttc atc atg aag cgt gga        1350
His Met Cys Arg Ala Ile Gly Glu Ser Phe Ile Met Lys Arg Gly
            440                 445                 450 gac agc ttc ctc gat ggg acc cgg tgt atg cca agt ggc ccc cgg        1395
Asp Ser Phe Leu Asp Gly Thr Arg Cys Met Pro Ser Gly Pro Arg
            455                 460                 465 gag gac ggg acc ctg agc ctg tgt gtg tcg ggc agc tgc agg aca        1440
Glu Asp Gly Thr Leu Ser Leu Cys Val Ser Gly Ser Cys Arg Thr
            470                 475                 480 ttt ggc tgt gat ggt agg atg gac tcc cag cag gta tgg gac agg        1485
Phe Gly Cys Asp Gly Arg Met Asp Ser Gln Gln Val Trp Asp Arg
            485                 490                 495 tgc cag gtg tgt ggt ggg gac aac agc acg tgc agc cca cgg aag        1530
Cys Gln Val Cys Gly Gly Asp Asn Ser Thr Cys Ser Pro Arg Lys
            500                 505                 510 ggc tct ttc aca gct ggc aga gcg aga gaa tat gtc acg ttt ctg        1575
Gly Ser Phe Thr Ala Gly Arg Ala Arg Glu Tyr Val Thr Phe Leu
            515                 520                 525 aca gtt acc ccc aac ctg acc agt gtc tac att gcc aac cac agg        1620
Thr Val Thr Pro Asn Leu Thr Ser Val Tyr Ile Ala Asn His Arg
            530                 535                 540 cct ctc ttc aca cac ttg gcg gtg agg atc gga ggg cgc tat gtc        1665
Pro Leu Phe Thr His Leu Ala Val Arg Ile Gly Gly Arg Tyr Val
            545                 550                 555 gtg gct ggg aag atg agc atc tcc cct aac acc acc tac ccc tcc        1710
Val Ala Gly Lys Met Ser Ile Ser Pro Asn Thr Thr Tyr Pro Ser
            560                 565                 570 ctc ctg gag gat ggt cgt gtc gag tac aga gtg gcc ctc acc gag        1755
Leu Leu Glu Asp Gly Arg Val Glu Tyr Arg Val Ala Leu Thr Glu
            575                 580                 585 gac cgg ctg ccc cgc ctg gag gag atc cgc atc tgg gga ccc ctc        1800
Asp Arg Leu Pro Arg Leu Glu Glu Ile Arg Ile Trp Gly Pro Leu
            590                 595                 600 cag gaa gat gct gac atc cag gtt tac agg cgg tat ggc gag gag        1845
Gln Glu Asp Ala Asp Ile Gln Val Tyr Arg Arg Tyr Gly Glu Glu
            605                 610                 615 tat ggc aac ctc acc cgc cca gac atc acc ttc acc tac ttc cag        1890
Tyr Gly Asn Leu Thr Arg Pro Asp Ile Thr Phe Thr Tyr Phe Gln
            620                 625                 630 cct aag cca cgg cag gcc tgg gtg tgg gcc gct gtg cgt ggg ccc        1935
Pro Lys Pro Arg Gln Ala Trp Val Trp Ala Ala Val Arg Gly Pro
            635                 640                 645 tgc tcg gtg agc tgt ggg gca ggg ctg cgc tgg gta aac tac agc        1980
Cys Ser Val Ser Cys Gly Ala Gly Leu Arg Trp Val Asn Tyr Ser
            650                 655                 660 tgc ctg gac cag gcc agg aag gag ttg gtg gag act gtc cag tgc        2025
Cys Leu Asp Gln Ala Arg Lys Glu Leu Val Glu Thr Val Gln Cys
            665                 670                 675 caa ggg agc cag cag cca cca gcg tgg cca gag gcc tgc gtg ctc        2070
Gln Gly Ser Gln Gln Pro Pro Ala Trp Pro Glu Ala Cys Val Leu
            680                 685                 690 gaa ccc tgc cct ccc tac tgg gcg gtg gga gac ttc ggc cca tgc        2115
Glu Pro Cys Pro Pro Tyr Trp Ala Val Gly Asp Phe Gly Pro Cys
            695                 700                 705 agc gcc tcc tgt ggg ggc ctg cgg gag cgg cca gtg cgc tgc        2160
Ser Ala Ser Cys Gly Gly Leu Arg Glu Arg Pro Val Arg Cys
            710                 715                 720 gtg gag gcc cag ggc agc ctc ctg aag aca ttg ccc cca gcc cgg        2205
Val Glu Ala Gln Gly Ser Leu Leu Lys Thr Leu Pro Pro Ala Arg
```

-continued

|  |  |
|---|---|
| 725 730 735 | |
| tgc aga gca ggg gcc cag cag cca gct gtg gcg ctg gaa acc tgc<br>Cys Arg Ala Gly Ala Gln Gln Pro Ala Val Ala Leu Glu Thr Cys<br>740 745 750 | 2250 |
| aac ccc cag ccc tgc cct gcc agg tgg gag gtg tca gag ccc agc<br>Asn Pro Gln Pro Cys Pro Ala Arg Trp Glu Val Ser Glu Pro Ser<br>755 760 765 | 2295 |
| tca tgc aca tca gct ggt gga gca ggc ctg gcc ttg gag aac gag<br>Ser Cys Thr Ser Ala Gly Gly Ala Gly Leu Ala Leu Glu Asn Glu<br>770 775 780 | 2340 |
| acc tgt gtg cca ggg gca gat ggc ctg gag gct cca gtg act gag<br>Thr Cys Val Pro Gly Ala Asp Gly Leu Glu Ala Pro Val Thr Glu<br>785 790 795 | 2385 |
| ggg cct ggc tcc gta gat gag aag ctg cct gcc cct gag ccc tgt<br>Gly Pro Gly Ser Val Asp Glu Lys Leu Pro Ala Pro Glu Pro Cys<br>800 805 810 | 2430 |
| gtc ggg atg tca tgt cct cca ggc tgg ggc cat ctg gat gcc acc<br>Val Gly Met Ser Cys Pro Pro Gly Trp Gly His Leu Asp Ala Thr<br>815 820 825 | 2475 |
| tct gca ggg gag aag gct ccc tcc cca tgg ggc agc atc agg acg<br>Ser Ala Gly Glu Lys Ala Pro Ser Pro Trp Gly Ser Ile Arg Thr<br>830 835 840 | 2520 |
| ggg gct caa gct gca cac gtg tgg acc cct gcg gca ggg tcg tgc<br>Gly Ala Gln Ala Ala His Val Trp Thr Pro Ala Ala Gly Ser Cys<br>845 850 855 | 2565 |
| tcc gtc tcc tgc ggg cga ggt ctg atg gag ctg cgt ttc ctg tgc<br>Ser Val Ser Cys Gly Arg Gly Leu Met Glu Leu Arg Phe Leu Cys<br>860 865 870 | 2610 |
| atg gac tct gcc ctc agg gtg cct gtc cag gaa gag ctg tgt ggc<br>Met Asp Ser Ala Leu Arg Val Pro Val Gln Glu Glu Leu Cys Gly<br>875 880 885 | 2655 |
| ctg gca agc aag cct ggg agc cgg cgg gag gtc tgc cag gct gtc<br>Leu Ala Ser Lys Pro Gly Ser Arg Arg Glu Val Cys Gln Ala Val<br>890 895 900 | 2700 |
| ccg tgc cct gct cgg tgg cag tac aag ctg gcg gcc tgc agc gtg<br>Pro Cys Pro Ala Arg Trp Gln Tyr Lys Leu Ala Ala Cys Ser Val<br>905 910 915 | 2745 |
| agc tgt ggg aga ggg gtc gtg cgg agg atc ctg tat tgt gcc cgg<br>Ser Cys Gly Arg Gly Val Val Arg Arg Ile Leu Tyr Cys Ala Arg<br>920 925 930 | 2790 |
| gcc cat ggg gag gac gat ggt gag gag atc ctg ttg gac acc cag<br>Ala His Gly Glu Asp Asp Gly Glu Glu Ile Leu Leu Asp Thr Gln<br>935 940 945 | 2835 |
| tgc cag ggg ctg cct cgc ccg gaa ccc cag gag gcc tgc agc ctg<br>Cys Gln Gly Leu Pro Arg Pro Glu Pro Gln Glu Ala Cys Ser Leu<br>950 955 960 | 2880 |
| gag ccc tgc cca cct agg tgg aaa gtc atg tcc ctt ggc cca tgt<br>Glu Pro Cys Pro Pro Arg Trp Lys Val Met Ser Leu Gly Pro Cys<br>965 970 975 | 2925 |
| tcg gcc agc tgt ggc ctt ggc act gct aga cgc tcg gtg gcc tgt<br>Ser Ala Ser Cys Gly Leu Gly Thr Ala Arg Arg Ser Val Ala Cys<br>980 985 990 | 2970 |
| gtg cag ctc gac caa ggc cag gac gtg gag gtg gac gag gcg gcc<br>Val Gln Leu Asp Gln Gly Gln Asp Val Glu Val Asp Glu Ala Ala<br>995 1000 1005 | 3015 |
| tgt gcg gcg ctg gtg cgg ccc gag gcc agt gtc ccc tgt ctc att<br>Cys Ala Ala Leu Val Arg Pro Glu Ala Ser Val Pro Cys Leu Ile<br>1010 1015 1020 | 3060 |
| gcc gac tgc acc tac cgc tgg cat gtt ggc acc tgg atg gag tgc<br>| 3105 |

-continued

| | | |
|---|---|---|
| Ala Asp Cys Thr Tyr Arg Trp His Val Gly Thr Trp Met Glu Cys<br>　　　　1025　　　　　　　　1030　　　　　　　　1035 | | |
| tct gtt tcc tgt ggg gat ggc atc cag cgc cgg cgt gac acc tgc<br>Ser Val Ser Cys Gly Asp Gly Ile Gln Arg Arg Arg Asp Thr Cys<br>　　1040　　　　　　　　1045　　　　　　　　1050 | 3150 | |
| ctc gga ccc cag gcc cag gcg cct gtg cca gct gat ttc tgc cag<br>Leu Gly Pro Gln Ala Gln Ala Pro Val Pro Ala Asp Phe Cys Gln<br>1055　　　　　　　　1060　　　　　　　　1065 | 3195 | |
| cac ttg ccc aag ccg gtg act gtg cgt ggc tgc tgg gct ggg ccc<br>His Leu Pro Lys Pro Val Thr Val Arg Gly Cys Trp Ala Gly Pro<br>　　1070　　　　　　　　1075　　　　　　　　1080 | 3240 | |
| tgt gtg gga cag ggt acg ccc agc ctg gtg ccc cac gaa gaa gcc<br>Cys Val Gly Gln Gly Thr Pro Ser Leu Val Pro His Glu Glu Ala<br>　　　　1085　　　　　　　　1090　　　　　　　　1095 | 3285 | |
| gct gct cca gga cgg acc aca gcc acc cct gct ggt gcc tcc ctg<br>Ala Ala Pro Gly Arg Thr Thr Ala Thr Pro Ala Gly Ala Ser Leu<br>1100　　　　　　　　1105　　　　　　　　1110 | 3330 | |
| gag tgg tcc cag gcc cgg ggc ctg ctc ttc tcc ccg gct ccc cag<br>Glu Trp Ser Gln Ala Arg Gly Leu Leu Phe Ser Pro Ala Pro Gln<br>　　1115　　　　　　　　1120　　　　　　　　1125 | 3375 | |
| cct cgg cgg ctc ctg ccc ggg ccc cag gaa aac tca gtg cag tcc<br>Pro Arg Arg Leu Leu Pro Gly Pro Gln Glu Asn Ser Val Gln Ser<br>　　　　1130　　　　　　　　1135　　　　　　　　1140 | 3420 | |
| agt gcc tgt ggc agg cag cac ctt gag cca aca gga acc att gac<br>Ser Ala Cys Gly Arg Gln His Leu Glu Pro Thr Gly Thr Ile Asp<br>1145　　　　　　　　1150　　　　　　　　1155 | 3465 | |
| atg cga ggc cca ggg cag gca gac tgt gca gtg gcc att ggg cgg<br>Met Arg Gly Pro Gly Gln Ala Asp Cys Ala Val Ala Ile Gly Arg<br>　　1160　　　　　　　　1165　　　　　　　　1170 | 3510 | |
| ccc ctc ggg gag gtg gtg acc ctc cgc gtc ctt gag agt tct ctc<br>Pro Leu Gly Glu Val Val Thr Leu Arg Val Leu Glu Ser Ser Leu<br>　　　　1175　　　　　　　　1180　　　　　　　　1185 | 3555 | |
| aac tgc agt gcg ggg gac atg ttg ctg ctt tgg ggc cgg ctc acc<br>Asn Cys Ser Ala Gly Asp Met Leu Leu Leu Trp Gly Arg Leu Thr<br>1190　　　　　　　　1195　　　　　　　　1200 | 3600 | |
| tgg agg aag atg tgc agg aag ctg ttg gac atg act ttc agc tcc<br>Trp Arg Lys Met Cys Arg Lys Leu Leu Asp Met Thr Phe Ser Ser<br>　　1205　　　　　　　　1210　　　　　　　　1215 | 3645 | |
| aag acc aac acg ctg gtg gtg agg cag cgc tgc ggg cgg cca gga<br>Lys Thr Asn Thr Leu Val Val Arg Gln Arg Cys Gly Arg Pro Gly<br>　　　　1220　　　　　　　　1225　　　　　　　　1230 | 3690 | |
| ggt ggg gtg ctg ctg cgg tat ggg agc cag ctt gct cct gaa acc<br>Gly Gly Val Leu Leu Arg Tyr Gly Ser Gln Leu Ala Pro Glu Thr<br>1235　　　　　　　　1240　　　　　　　　1245 | 3735 | |
| ttc tac aga gaa tgt gac atg cag ctc ttt ggg ccc tgg ggt gaa<br>Phe Tyr Arg Glu Cys Asp Met Gln Leu Phe Gly Pro Trp Gly Glu<br>　　1250　　　　　　　　1255　　　　　　　　1260 | 3780 | |
| atc gtg agc ccc tcg ctg agt cca gcc acg agt aat gca ggg ggc<br>Ile Val Ser Pro Ser Leu Ser Pro Ala Thr Ser Asn Ala Gly Gly<br>　　　　1265　　　　　　　　1270　　　　　　　　1275 | 3825 | |
| tgc cgg ctc ttc att aat gtg gct ccg cac gca cgg att gcc atc<br>Cys Arg Leu Phe Ile Asn Val Ala Pro His Ala Arg Ile Ala Ile<br>1280　　　　　　　　1285　　　　　　　　1290 | 3870 | |
| cat gcc ctg gcc acc aac atg ggc gct ggg acc gag gga gcc aat<br>His Ala Leu Ala Thr Asn Met Gly Ala Gly Thr Glu Gly Ala Asn<br>　　1295　　　　　　　　1300　　　　　　　　1305 | 3915 | |
| gcc agc tac atc ttg atc cgg gac acc cac agc ttg agg acc aca<br>Ala Ser Tyr Ile Leu Ile Arg Asp Thr His Ser Leu Arg Thr Thr<br>　　　　1310　　　　　　　　1315　　　　　　　　1320 | 3960 | |

| | | |
|---|---|---|
| gcg ttc cat ggg cag cag gtg ctc tac tgg gag tca gag agc agc<br>Ala Phe His Gly Gln Gln Val Leu Tyr Trp Glu Ser Glu Ser Ser<br>               1325               1330               1335 | | 4005 |
| cag gct gag atg gag ttc agc gag ggc ttc ctg aag gct cag gcc<br>Gln Ala Glu Met Glu Phe Ser Glu Gly Phe Leu Lys Ala Gln Ala<br>   1340               1345               1350 | | 4050 |
| agc ctg cgg ggc cag tac tgg acc ctc caa tca tgg gta ccg gag<br>Ser Leu Arg Gly Gln Tyr Trp Thr Leu Gln Ser Trp Val Pro Glu<br>               1355               1360               1365 | | 4095 |
| atg cag gac cct cag tcc tgg aag gga aag gaa gga acc<br>Met Gln Asp Pro Gln Ser Trp Lys Gly Lys Glu Gly Thr<br>   1370               1375 | | 4134 |

<210> SEQ ID NO 19
<211> LENGTH: 1322
<212> TYPE: PRT
<213> ORGANISM: Homo sapiens

<400> SEQUENCE: 19

| | | |
|---|---|---|
| gct gca ggc ggc atc cta cac ctg gag ctg ctg gtg gcc gtg ggc<br>Ala Ala Gly Gly Ile Leu His Leu Glu Leu Leu Val Ala Val Gly<br>1               5                     10                    15 | | 45 |
| ccc gat gtc ttc cag gct cac cag gag gac aca gag cgc tat gtg<br>Pro Asp Val Phe Gln Ala His Gln Glu Asp Thr Glu Arg Tyr Val<br>               20                25               30 | | 90 |
| ctc acc aac ctc aac atc ggg gca gaa ctg ctt cgg gac ccg tcc<br>Leu Thr Asn Leu Asn Ile Gly Ala Glu Leu Leu Arg Asp Pro Ser<br>               35               40               45 | | 135 |
| ctg ggg gct cag ttt cgg gtg cac ctg gtg aag atg gtc att ctg<br>Leu Gly Ala Gln Phe Arg Val His Leu Val Lys Met Val Ile Leu<br>    50               55               60 | | 180 |
| aca gag cct gag ggt gct cca aat atc aca gcc aac ctc acc tcg<br>Thr Glu Pro Glu Gly Ala Pro Asn Ile Thr Ala Asn Leu Thr Ser<br>         65                  70               75 | | 225 |
| tcc ctg ctg agc gtc tgt ggg tgg agc cag acc atc aac cct gag<br>Ser Leu Leu Ser Val Cys Gly Trp Ser Gln Thr Ile Asn Pro Glu<br>        80                  85               90 | | 270 |
| gac gac acg gat cct ggc cat gct gac ctg gtc ctc tat atc act<br>Asp Asp Thr Asp Pro Gly His Ala Asp Leu Val Leu Tyr Ile Thr<br>               95              100              105 | | 315 |
| agg ttt gac ctg gag ttg cct gat ggt aac cgg cag gtg cgg ggc<br>Arg Phe Asp Leu Glu Leu Pro Asp Gly Asn Arg Gln Val Arg Gly<br>   110               115               120 | | 360 |
| gtc acc cag ctg ggc ggt gcc tgc tcc cca acc tgg agc tgc ctc<br>Val Thr Gln Leu Gly Gly Ala Cys Ser Pro Thr Trp Ser Cys Leu<br>               125               130               135 | | 405 |
| att acc gag gac act ggc ttc gac ctg gga gtc acc att gcc cat<br>Ile Thr Glu Asp Thr Gly Phe Asp Leu Gly Val Thr Ile Ala His<br>              140               145               150 | | 450 |
| gag att ggg cac agc ttc ggc ctg gag cac gac ggc gcg ccc ggc<br>Glu Ile Gly His Ser Phe Gly Leu Glu His Asp Gly Ala Pro Gly<br>               155               160               165 | | 495 |
| agc ggc tgc ggc ccc agc gga cac gtg atg gct tcg gac ggc gcc<br>Ser Gly Cys Gly Pro Ser Gly His Val Met Ala Ser Asp Gly Ala<br>            170                175               180 | | 540 |
| gcg ccc cgc gcc ggc ctc gcc tgg tcc ccc tgc agc cgc cgg cag<br>Ala Pro Arg Ala Gly Leu Ala Trp Ser Pro Cys Ser Arg Arg Gln<br>               185               190               195 | | 585 |
| ctg ctg agc ctg ctc agg acg ggc gcg ctg cgt gtg gga ccc gcc<br>Leu Leu Ser Leu Leu Arg Thr Gly Ala Leu Arg Val Gly Pro Ala<br>            200                205               210 | | 630 |

-continued

```
gcg gcc tca acc cgg gtc cgc ggg gca ccc gcc gga tgc gca gcc        675
Ala Ala Ser Thr Arg Val Arg Gly Ala Pro Ala Gly Cys Ala Ala
            215                 220                 225 tgg cct cta cta cag cgc caa cga gca gtg ccg cgt ggc ctt cgg        720
Trp Pro Leu Leu Gln Arg Gln Arg Ala Val Pro Arg Gly Leu Arg
            230                 235                 240 ccc caa ggc tgt cgc ctg cac ctt cgc cag gga gca cct ggt gag        765
Pro Gln Gly Cys Arg Leu His Leu Arg Gln Gly Ala Pro Gly Glu
            245                 250                 255 tct gcc ggc ggt ggc ctg gga ttg gct gtg agg tcc ctc cgc atc        810
Ser Ala Gly Gly Gly Leu Gly Leu Ala Val Arg Ser Leu Arg Ile
            260                 265                 270 acc cag ctc acg tcc ccc caa acg tgc atg gat atg tgc cag gcc        855
Thr Gln Leu Thr Ser Pro Gln Thr Cys Met Asp Met Cys Gln Ala
            275                 280                 285 ctc tcc tgc cac aca gac ccg ctg gac caa agc agc tgc agc cgc        900
Leu Ser Cys His Thr Asp Pro Leu Asp Gln Ser Ser Cys Ser Arg
            290                 295                 300 ctc ctc gtt cct ctc ctg gat ggg aca gaa tgt ggc gtg gag aag        945
Leu Leu Val Pro Leu Leu Asp Gly Thr Glu Cys Gly Val Glu Lys
            305                 310                 315 tgg tgc tcc aag ggt cgc tgc cgc tcc ctg gtg gag ctg acc ccc        990
Trp Cys Ser Lys Gly Arg Cys Arg Ser Leu Val Glu Leu Thr Pro
            320                 325                 330 ata gca gca gtg cat ggg cgc tgg tct agc tgg ggt ccc cga agt       1035
Ile Ala Ala Val His Gly Arg Trp Ser Ser Trp Gly Pro Arg Ser
            335                 340                 345 cct tgc tcc cgc tcc tgc gga gga ggt gtg gtc acc agg agg cgg       1080
Pro Cys Ser Arg Ser Cys Gly Gly Gly Val Val Thr Arg Arg Arg
            350                 355                 360 cag tgc aac aac ccc aga cct gcc ttt ggg ggg cgt gca tgt gtt       1125
Gln Cys Asn Asn Pro Arg Pro Ala Phe Gly Gly Arg Ala Cys Val
            365                 370                 375 ggt gct gac ctc cag gcc gag atg tgc aac act cag gcc tgc gag       1170
Gly Ala Asp Leu Gln Ala Glu Met Cys Asn Thr Gln Ala Cys Glu
            380                 385                 390 aag acc cag ctg gag ttc atg tcg caa cag tgc gcc agg acc gac       1215
Lys Thr Gln Leu Glu Phe Met Ser Gln Gln Cys Ala Arg Thr Asp
            395                 400                 405 ggc cag ccg ctg cgc tcc tcc cct ggc ggc gcc tcc ttc tac cac       1260
Gly Gln Pro Leu Arg Ser Ser Pro Gly Gly Ala Ser Phe Tyr His
            410                 415                 420 tgg ggt gct gct gta cca cac agc caa ggg gat gct ctg tgc aga       1305
Trp Gly Ala Ala Val Pro His Ser Gln Gly Asp Ala Leu Cys Arg
            425                 430                 435 cac atg tgc cgg gcc att ggc gag agc ttc atc atg aag cgt gga       1350
His Met Cys Arg Ala Ile Gly Glu Ser Phe Ile Met Lys Arg Gly
            440                 445                 450 gac agc ttc ctc gat ggg acc cgg tgt atg cca agt ggc ccc cgg       1395
Asp Ser Phe Leu Asp Gly Thr Arg Cys Met Pro Ser Gly Pro Arg
            455                 460                 465 gag gac ggg acc ctg agc ctg tgt gtg tcg ggc agc tgc agg aca       1440
Glu Asp Gly Thr Leu Ser Leu Cys Val Ser Gly Ser Cys Arg Thr
            470                 475                 480 ttt ggc tgt gat ggt agg atg gac tcc cag cag gta tgg gac agg       1485
Phe Gly Cys Asp Gly Arg Met Asp Ser Gln Gln Val Trp Asp Arg
            485                 490                 495 tgc cag gtg tgt ggt ggg gac aac agc acg tgc agc cca cgg aag       1530
Cys Gln Val Cys Gly Gly Asp Asn Ser Thr Cys Ser Pro Arg Lys
```

-continued

| | |
|---|---|
| ggc tct ttc aca gct ggc aga gcg aga gaa tat gtc acg ttt ctg<br>Gly Ser Phe Thr Ala Gly Arg Ala Arg Glu Tyr Val Thr Phe Leu<br>515                     520                   525 | 1575 |
| aca gtt acc ccc aac ctg acc agt gtc tac att gcc aac cac agg<br>Thr Val Thr Pro Asn Leu Thr Ser Val Tyr Ile Ala Asn His Arg<br>530                     535                   540 | 1620 |
| cct ctc ttc aca cac ttg gcg gtg agg atc gga ggg cgc tat gtc<br>Pro Leu Phe Thr His Leu Ala Val Arg Ile Gly Gly Arg Tyr Val<br>545                     550                   555 | 1665 |
| gtg gct ggg aag atg agc atc tcc cct aac acc acc tac ccc tcc<br>Val Ala Gly Lys Met Ser Ile Ser Pro Asn Thr Thr Tyr Pro Ser<br>560                     565                   570 | 1710 |
| ctc ctg gag gat ggt cgt gtc gag tac aga gtg gcc ctc acc gag<br>Leu Leu Glu Asp Gly Arg Val Glu Tyr Arg Val Ala Leu Thr Glu<br>575                     580                   585 | 1755 |
| gac cgg ctg ccc cgc ctg gag gag atc cgc atc tgg gga ccc ctc<br>Asp Arg Leu Pro Arg Leu Glu Glu Ile Arg Ile Trp Gly Pro Leu<br>590                     595                   600 | 1800 |
| cag gaa gat gct gac atc cag gtt tac agg cgg tat ggc gag gag<br>Gln Glu Asp Ala Asp Ile Gln Val Tyr Arg Arg Tyr Gly Glu Glu<br>605                     610                   615 | 1845 |
| tat ggc aac ctc acc cgc cca gac atc acc ttc acc tac ttc cag<br>Tyr Gly Asn Leu Thr Arg Pro Asp Ile Thr Phe Thr Tyr Phe Gln<br>620                     625                   630 | 1890 |
| cct aag cca cgg cag gcc tgg gtg tgg gcc gct gtg cgt ggg ccc<br>Pro Lys Pro Arg Gln Ala Trp Val Trp Ala Ala Val Arg Gly Pro<br>635                     640                   645 | 1935 |
| tgc tcg gtg agc tgt ggg gca ggg ctg cgc tgg gta aac tac agc<br>Cys Ser Val Ser Cys Gly Ala Gly Leu Arg Trp Val Asn Tyr Ser<br>650                     655                   660 | 1980 |
| tgc ctg gac cag gcc agg aag gag ttg gtg gag act gtc cag tgc<br>Cys Leu Asp Gln Ala Arg Lys Glu Leu Val Glu Thr Val Gln Cys<br>665                     670                   675 | 2025 |
| caa ggg agc cag cag cca cca gcg tgg cca gag gcc tgc gtg ctc<br>Gln Gly Ser Gln Gln Pro Pro Ala Trp Pro Glu Ala Cys Val Leu<br>680                     685                   690 | 2070 |
| gaa ccc tgc cct ccc tac tgg gcg gtg gga gac ttc ggc cca tgc<br>Glu Pro Cys Pro Pro Tyr Trp Ala Val Gly Asp Phe Gly Pro Cys<br>695                     700                   705 | 2115 |
| agc gcc tcc tgt ggg ggc ggc ctg cgg gag cgg cca gtg cgc tgc<br>Ser Ala Ser Cys Gly Gly Gly Leu Arg Glu Arg Pro Val Arg Cys<br>710                     715                   720 | 2160 |
| gtg gag gcc cag ggc agc ctc ctg aag aca ttg ccc cca gcc cgg<br>Val Glu Ala Gln Gly Ser Leu Leu Lys Thr Leu Pro Pro Ala Arg<br>725                     730                   735 | 2205 |
| tgc aga gca ggg gcc cag cag cca gct gtg gcg ctg gaa acc tgc<br>Cys Arg Ala Gly Ala Gln Gln Pro Ala Val Ala Leu Glu Thr Cys<br>740                     745                   750 | 2250 |
| aac ccc cag ccc tgc cct gcc agg tgg gag gtg tca gag ccc agc<br>Asn Pro Gln Pro Cys Pro Ala Arg Trp Glu Val Ser Glu Pro Ser<br>755                     760                   765 | 2295 |
| tca tgc aca tca gct ggt gga gca ggc ctg gcc ttg gag aac gag<br>Ser Cys Thr Ser Ala Gly Gly Ala Gly Leu Ala Leu Glu Asn Glu<br>770                     775                   780 | 2340 |
| acc tgt gtg cca ggg gca gat ggc ctg gag gct cca gtg act gag<br>Thr Cys Val Pro Gly Ala Asp Gly Leu Glu Ala Pro Val Thr Glu<br>785                     790                   795 | 2385 |
| ggg cct ggc tcc gta gat gag aag ctg cct gcc cct gag ccc tgt | 2430 |

-continued

```
                Gly Pro Gly Ser Val Asp Glu Lys Leu Pro Ala Pro Glu Pro Cys
                                800                 805                 810 gtc ggg atg tca tgt cct cca ggc tgg ggc cat ctg gat gcc acc           2475
Val Gly Met Ser Cys Pro Pro Gly Trp Gly His Leu Asp Ala Thr
            815                 820                 825 tct gca ggg gag aag gct ccc tcc cca tgg ggc agc atc agg acg           2520
Ser Ala Gly Glu Lys Ala Pro Ser Pro Trp Gly Ser Ile Arg Thr
            830                 835                 840 ggg gct caa gct gca cac gtg tgg acc cct gcg gca ggg tcg tgc           2565
Gly Ala Gln Ala Ala His Val Trp Thr Pro Ala Ala Gly Ser Cys
            845                 850                 855 tcc gtc tcc tgc ggg cga ggt ctg atg gag ctg cgt ttc ctg tgc           2610
Ser Val Ser Cys Gly Arg Gly Leu Met Glu Leu Arg Phe Leu Cys
            860                 865                 870 atg gac tct gcc ctc agg gtg cct gtc cag gaa gag ctg tgt ggc           2655
Met Asp Ser Ala Leu Arg Val Pro Val Gln Glu Glu Leu Cys Gly
            875                 880                 885 ctg gca agc aag cct ggg agc cgg cgg gag gtc tgc cag gct gtc           2700
Leu Ala Ser Lys Pro Gly Ser Arg Arg Glu Val Cys Gln Ala Val
            890                 895                 900 ccg tgc cct gct cgg tgg cag tac aag ctg gcg gcc tgc agc gtg           2745
Pro Cys Pro Ala Arg Trp Gln Tyr Lys Leu Ala Ala Cys Ser Val
            905                 910                 915 agc tgt ggg aga ggg gtc gtg cgg agg atc ctg tat tgt gcc cgg           2790
Ser Cys Gly Arg Gly Val Val Arg Arg Ile Leu Tyr Cys Ala Arg
            920                 925                 930 gcc cat ggg gag gac gat ggt gag gag atc ctg ttg gac acc cag           2835
Ala His Gly Glu Asp Asp Gly Glu Glu Ile Leu Leu Asp Thr Gln
            935                 940                 945 tgc cag ggg ctg cct cgc ccg gaa ccc cag gag gcc tgc agc ctg           2880
Cys Gln Gly Leu Pro Arg Pro Glu Pro Gln Glu Ala Cys Ser Leu
            950                 955                 960 gag ccc tgc cca cct agg tgg aaa gtc atg tcc ctt ggc cca tgt           2925
Glu Pro Cys Pro Pro Arg Trp Lys Val Met Ser Leu Gly Pro Cys
            965                 970                 975 tcg gcc agc tgt ggc ctt ggc act gct aga cgc tcg gtg gcc tgt           2970
Ser Ala Ser Cys Gly Leu Gly Thr Ala Arg Arg Ser Val Ala Cys
            980                 985                 990 gtg cag ctc gac caa ggc cag gac gtg gag gtg gac gag gcg gcc           3015
Val Gln Leu Asp Gln Gly Gln Asp Val Glu Val Asp Glu Ala Ala
            995                 1000                1005 tgt gcg gcg ctg gtg cgg ccc gag gcc agt gtc ccc tgt ctc att           3060
Cys Ala Ala Leu Val Arg Pro Glu Ala Ser Val Pro Cys Leu Ile
            1010                1015                1020 gcc gac tgc acc tac cgc tgg cat gtt ggc acc tgg atg gag tgc           3105
Ala Asp Cys Thr Tyr Arg Trp His Val Gly Thr Trp Met Glu Cys
            1025                1030                1035 tct gtt tcc tgt ggg gat ggc atc cag cgc cgg cgt gac acc tgc           3150
Ser Val Ser Cys Gly Asp Gly Ile Gln Arg Arg Arg Asp Thr Cys
            1040                1045                1050 ctc gga ccc cag gcc cag gcg cct gtg cca gct gat ttc tgc cag           3195
Leu Gly Pro Gln Ala Gln Ala Pro Val Pro Ala Asp Phe Cys Gln
            1055                1060                1065 cac ttg ccc aag ccg gtg act gtg cgt ggc tgc tgg gct ggg ccc           3240
His Leu Pro Lys Pro Val Thr Val Arg Gly Cys Trp Ala Gly Pro
            1070                1075                1080 tgt gtg gga cag ggt gcc tgt ggc agg cag cac ctt gag cca aca           3285
Cys Val Gly Gln Gly Ala Cys Gly Arg Gln His Leu Glu Pro Thr
            1085                1090                1095
```

-continued

| | | |
|---|---|---|
| gga acc att gac atg cga ggc cca ggg cag gca gac tgt gca gtg<br>Gly Thr Ile Asp Met Arg Gly Pro Gly Gln Ala Asp Cys Ala Val<br>                  1100                  1105                1110 | | 3330 |
| gcc att ggg cgg ccc ctc ggg gag gtg gtg acc ctc cgc gtc ctt<br>Ala Ile Gly Arg Pro Leu Gly Glu Val Val Thr Leu Arg Val Leu<br>                  1115                  1120                1125 | | 3375 |
| gag agt tct ctc aac tgc agt gcg ggg gac atg ttg ctg ctt tgg<br>Glu Ser Ser Leu Asn Cys Ser Ala Gly Asp Met Leu Leu Leu Trp<br>                  1130                  1135                1140 | | 3420 |
| ggc cgg ctc acc tgg agg aag atg tgc agg aag ctg ttg gac atg<br>Gly Arg Leu Thr Trp Arg Lys Met Cys Arg Lys Leu Leu Asp Met<br>                  1145                  1150                1155 | | 3465 |
| act ttc agc tcc aag acc aac acg ctg gtg gtg agg cag cgc tgc<br>Thr Phe Ser Ser Lys Thr Asn Thr Leu Val Val Arg Gln Arg Cys<br>                  1160                  1165                1170 | | 3510 |
| ggg cgg cca gga ggt ggg gtg ctg ctg cgg tat ggg agc cag ctt<br>Gly Arg Pro Gly Gly Gly Val Leu Leu Arg Tyr Gly Ser Gln Leu<br>                  1175                  1180                1185 | | 3555 |
| gct cct gaa acc ttc tac aga gaa tgt gac atg cag ctc ttt ggg<br>Ala Pro Glu Thr Phe Tyr Arg Glu Cys Asp Met Gln Leu Phe Gly<br>                  1190                  1195                1200 | | 3600 |
| ccc tgg ggt gaa atc gtg agc ccc tcg ctg agt cca gcc acg agt<br>Pro Trp Gly Glu Ile Val Ser Pro Ser Leu Ser Pro Ala Thr Ser<br>                  1205                  1210                1215 | | 3645 |
| aat gca ggg ggc tgc cgg ctc ttc att aat gtg gct ccg cac gca<br>Asn Ala Gly Gly Cys Arg Leu Phe Ile Asn Val Ala Pro His Ala<br>                  1220                  1225                1230 | | 3690 |
| cgg att gcc atc cat gcc ctg gcc acc aac atg ggc gct ggg acc<br>Arg Ile Ala Ile His Ala Leu Ala Thr Asn Met Gly Ala Gly Thr<br>                  1235                  1240                1245 | | 3735 |
| gag gga gcc aat gcc agc tac atc ttg atc cgg gac acc cac agc<br>Glu Gly Ala Asn Ala Ser Tyr Ile Leu Ile Arg Asp Thr His Ser<br>                  1250                  1255                1260 | | 3780 |
| ttg agg acc aca gcg ttc cat ggg cag cag gtg ctc tac tgg gag<br>Leu Arg Thr Thr Ala Phe His Gly Gln Gln Val Leu Tyr Trp Glu<br>                  1265                  1270                1275 | | 3825 |
| tca gag agc agc cag gct gag atg gag ttc agc gag ggc ttc ctg<br>Ser Glu Ser Ser Gln Ala Glu Met Glu Phe Ser Glu Gly Phe Leu<br>                  1280                  1285                1290 | | 3870 |
| aag gct cag gcc agc ctg cgg ggc cag tac tgg acc ctc caa tca<br>Lys Ala Gln Ala Ser Leu Arg Gly Gln Tyr Trp Thr Leu Gln Ser<br>                  1295                  1300                1305 | | 3915 |
| tgg gta ccg gag atg cag gac cct cag tcc tgg aag gga aag gaa<br>Trp Val Pro Glu Met Gln Asp Pro Gln Ser Trp Lys Gly Lys Glu<br>                  1310                  1315                1320 | | 3960 |
| gga acc<br>Gly Thr | | 3966 |

<210> SEQ ID NO 20
<211> LENGTH: 312
<212> TYPE: PRT
<213> ORGANISM: Homo sapiens

<400> SEQUENCE: 20

| | | |
|---|---|---|
| gct gca ggc ggc atc cta cac ctg gag ctg ctg gtg gcc gtg ggc<br>Ala Ala Gly Gly Ile Leu His Leu Glu Leu Leu Val Ala Val Gly<br>1                  5                  10                15 | | 45 |
| ccc gat gtc ttc cag gct cac cag gag gac aca gag cgc tat gtg<br>Pro Asp Val Phe Gln Ala His Gln Glu Asp Thr Glu Arg Tyr Val<br>                  20                  25                30 | | 90 |

-continued

| | | |
|---|---|---|
| ctc acc aac ctc aac atc ggg gca gaa ctg ctt cgg gac ccg tcc<br>Leu Thr Asn Leu Asn Ile Gly Ala Glu Leu Leu Arg Asp Pro Ser<br>                   35                  40                  45 | 135 |
| ctg ggg gct cag ttt cgg gtg cac ctg gtg aag atg gtc att ctg<br>Leu Gly Ala Gln Phe Arg Val His Leu Val Lys Met Val Ile Leu<br> 50                  55                  60 | 180 |
| aca gag cct gag ggt gct cca aat atc aca gcc aac ctc acc tcg<br>Thr Glu Pro Glu Gly Ala Pro Asn Ile Thr Ala Asn Leu Thr Ser<br>               65                  70                  75 | 225 |
| tcc ctg ctg agc gtc tgt ggg tgg agc cag acc atc aac cct gag<br>Ser Leu Leu Ser Val Cys Gly Trp Ser Gln Thr Ile Asn Pro Glu<br>            80                  85                  90 | 270 |
| gac gac acg gat cct ggc cat gct gac ctg gtc ctc tat atc act<br>Asp Asp Thr Asp Pro Gly His Ala Asp Leu Val Leu Tyr Ile Thr<br>               95                 100              105 | 315 |
| agg ttt gac ctg gag ttg cct gat ggt aac cgg cag gtg cgg ggc<br>Arg Phe Asp Leu Glu Leu Pro Asp Gly Asn Arg Gln Val Arg Gly<br>            110                 115              120 | 360 |
| gtc acc cag ctg ggc ggt gcc tgc tcc cca acc tgg agc tgc ctc<br>Val Thr Gln Leu Gly Gly Ala Cys Ser Pro Thr Trp Ser Cys Leu<br>               125                 130              135 | 405 |
| att acc gag gac act ggc ttc gac ctg gga gtc acc att gcc cat<br>Ile Thr Glu Asp Thr Gly Phe Asp Leu Gly Val Thr Ile Ala His<br>            140                 145              150 | 450 |
| gag att ggg cac agc ttc ggc ctg gag cac gac ggc gcg ccc ggc<br>Glu Ile Gly His Ser Phe Gly Leu Glu His Asp Gly Ala Pro Gly<br>               155                 160              165 | 495 |
| agc ggc tgc ggc ccc agc gga cac gtg atg gct tcg gac ggc gcc<br>Ser Gly Cys Gly Pro Ser Gly His Val Met Ala Ser Asp Gly Ala<br>            170                 175              180 | 540 |
| gcg ccc cgc gcc ggc ctc gcc tgg tcc ccc tgc agc cgc cgg cag<br>Ala Pro Arg Ala Gly Leu Ala Trp Ser Pro Cys Ser Arg Arg Gln<br>               185                 190              195 | 585 |
| ctg ctg agc ctg ctc agg acg ggc gcg ctg cgt gtg gga ccc gcc<br>Leu Leu Ser Leu Leu Arg Thr Gly Ala Leu Arg Val Gly Pro Ala<br>            200                 205              210 | 630 |
| gcg gcc tca acc cgg gtc cgc ggg gca ccc gcc gga tgc gca gcc<br>Ala Ala Ser Thr Arg Val Arg Gly Ala Pro Ala Gly Cys Ala Ala<br>               215                 220              225 | 675 |
| tgg cct cta cta cag cgc caa cga gca gtg ccg cgt ggc ctt cgg<br>Trp Pro Leu Leu Gln Arg Gln Arg Ala Val Pro Arg Gly Leu Arg<br>            230                 235              240 | 720 |
| ccc caa ggc tgt cgc ctg cac ctt cgc cag gga gca cct gga tat<br>Pro Gln Gly Cys Arg Leu His Leu Arg Gln Gly Ala Pro Gly Tyr<br>               245                 250              255 | 765 |
| gtg cca ggc cct ctc ctg cca cac aga ccc gct gga cca aag cag<br>Val Pro Gly Pro Leu Leu Pro His Arg Pro Ala Gly Pro Lys Gln<br>            260                 265              270 | 810 |
| ctg cag ccg cct cct cgt tcc tct cct gga tgg gac aga atg tgg<br>Leu Gln Pro Pro Pro Arg Ser Ser Pro Gly Trp Asp Arg Met Trp<br>               275                 280              285 | 855 |
| cgt gga gaa gtg gtg ctc caa ggg tcg ctg ccg ctc cct ggt gga<br>Arg Gly Glu Val Val Leu Gln Gly Ser Leu Pro Leu Pro Gly Gly<br>            290                 295              300 | 900 |
| gct gac ccc cat agc agc agt gca tgg gcg ctg gtc<br>Ala Asp Pro His Ser Ser Ser Ala Trp Ala Leu Val<br>               305                 310 | 936 |

<210> SEQ ID NO 21
<211> LENGTH: 270

<212> TYPE: PRT
<213> ORGANISM: Homo sapiens

<400> SEQUENCE: 21

```
gct gca ggc ggc atc cta cac ctg gag ctg ctg gtg gcc gtg ggc      45
Ala Ala Gly Gly Ile Leu His Leu Glu Leu Leu Val Ala Val Gly
1               5                  10                  15 ccc gat gtc ttc cag gct cac cag gag gac aca gag cgc tat gtg      90
Pro Asp Val Phe Gln Ala His Gln Glu Asp Thr Glu Arg Tyr Val
            20                  25                  30 ctc acc aac ctc aac atc ggg gca gaa ctg ctt cgg gac ccg tcc     135
Leu Thr Asn Leu Asn Ile Gly Ala Glu Leu Leu Arg Asp Pro Ser
        35                  40                  45 ctg ggg gct cag ttt cgg gtg cac ctg gtg aag atg gtc att ctg     180
Leu Gly Ala Gln Phe Arg Val His Leu Val Lys Met Val Ile Leu
    50                  55                  60 aca gag cct gag ggt gct cca aat atc aca gcc aac ctc acc tcg     225
Thr Glu Pro Glu Gly Ala Pro Asn Ile Thr Ala Asn Leu Thr Ser
65                  70                  75 tcc ctg ctg agc gtc tgt ggg tgg agc cag acc atc aac cct gag     270
Ser Leu Leu Ser Val Cys Gly Trp Ser Gln Thr Ile Asn Pro Glu
                80                  85                  90 gac gac acg gat cct ggc cat gct gac ctg gtc ctc tat atc act     315
Asp Asp Thr Asp Pro Gly His Ala Asp Leu Val Leu Tyr Ile Thr
            95                 100                 105 agg ttt gac ctg gag ttg cct gat ggt aac cgg cag gtg cgg ggc     360
Arg Phe Asp Leu Glu Leu Pro Asp Gly Asn Arg Gln Val Arg Gly
        110                 115                 120 gtc acc cag ctg ggc ggt gcc tgc tcc cca acc tgg agc tgc ctc     405
Val Thr Gln Leu Gly Gly Ala Cys Ser Pro Thr Trp Ser Cys Leu
    125                 130                 135 att acc gag gac act ggc ttc gac ctg gga gtc acc att gcc cat     450
Ile Thr Glu Asp Thr Gly Phe Asp Leu Gly Val Thr Ile Ala His
140                 145                 150 gag att ggg cac agc ttc ggc ctg gag cac gac ggc gcg ccc ggc     495
Glu Ile Gly His Ser Phe Gly Leu Glu His Asp Gly Ala Pro Gly
                155                 160                 165 agc ggc tgc ggc ccc agc gga cac gtg atg gct tcg gac ggc gcc     540
Ser Gly Cys Gly Pro Ser Gly His Val Met Ala Ser Asp Gly Ala
            170                 175                 180 gcg ccc cgc gcc ggc ctc gcc tgg tcc ccc tgc agc cgc cgg cag     585
Ala Pro Arg Ala Gly Leu Ala Trp Ser Pro Cys Ser Arg Arg Gln
        185                 190                 195 ctg ctg agc ctg ctc aga ccc gtc cct ccg tcg ccg ctc cct ctg     630
Leu Leu Ser Leu Leu Arg Pro Val Pro Pro Ser Pro Leu Pro Leu
    200                 205                 210 ctg gcc acc cac ctc tgc gcc ggc agg agc ctt agt ctt ggt ccc     675
Leu Ala Thr His Leu Cys Ala Gly Arg Ser Leu Ser Leu Gly Pro
215                 220                 225 agc caa gag ccg gct cct ggt ggg ggg cgc ggg ccg aga act cct     720
Ser Gln Glu Pro Ala Pro Gly Gly Gly Arg Gly Pro Arg Thr Pro
                230                 235                 240 gtt ccc act cac aaa agg cca cgc ttc caa acg ctt cca tcc tcg     765
Val Pro Thr His Lys Arg Pro Arg Phe Gln Thr Leu Pro Ser Ser
            245                 250                 255 tgc cca ctc ctc cgt ccc gcc tcc tcc cgg tgt aca ccc cgg gac     810
Cys Pro Leu Leu Arg Pro Ala Ser Ser Arg Cys Thr Pro Arg Asp
        260                 265                 270
```

<210> SEQ ID NO 22

```
<211> LENGTH: 43
<212> TYPE: DNA
<213> ORGANISM: Homo sapiens

<400> SEQUENCE: 22
ggactcgagc caccaatgca ccagcgtcac ccccgggcaa gat                  43

<210> SEQ ID NO 23
<211> LENGTH: 45
<212> TYPE: DNA
<213> ORGANISM: Homo sapiens

<400> SEQUENCE: 23
tccgtcgact cattatcagg ttccttcctt tcccttccag gactg                45

<210> SEQ ID NO 24
<211> LENGTH: 30
<212> TYPE: DNA
<213> ORGANISM: Homo sapiens

<400> SEQUENCE: 24
ggttggcaat gtagacactg gtcaggttgg                                 30

<210> SEQ ID NO 25
<211> LENGTH: 30
<212> TYPE: DNA
<213> ORGANISM: Homo sapiens

<400> SEQUENCE: 25
ccaacctgac cagtgtctac attgccaacc                                 30

<210> SEQ ID NO 26
<211> LENGTH: 30
<212> TYPE: DNA
<213> ORGANISM: Homo sapiens

<400> SEQUENCE: 26
ctttccacct aggtgggcag ggctccaggc                                 30

<210> SEQ ID NO 27
<211> LENGTH: 30
<212> TYPE: DNA
<213> ORGANISM: Homo sapiens

<400> SEQUENCE: 27
gcctggagcc ctgcccacct aggtggaaag                                 30

<210> SEQ ID NO 28
<211> LENGTH: 33
<212> TYPE: DNA
<213> ORGANISM: Homo sapiens

<400> SEQUENCE: 28
tcgagaaaaa gtctacgggg gcctaggttt tta                             33

<210> SEQ ID NO 29
<211> LENGTH: 33
<212> TYPE: DNA
<213> ORGANISM: Homo sapiens

<400> SEQUENCE: 29
agcttaaaaa cctaggcccc cgtagacttt ttc                             33
```

<210> SEQ ID NO 30
<211> LENGTH: 30
<212> TYPE: DNA
<213> ORGANISM: Homo sapiens

<400> SEQUENCE: 30
tcggccatgg ccgcaggcgg catcctacac                                  30

<210> SEQ ID NO 31
<211> LENGTH: 28
<212> TYPE: DNA
<213> ORGANISM: Homo sapiens

<400> SEQUENCE: 31
ggcaagctta tcagcggggc gcggcgcc                                    28

<210> SEQ ID NO 32
<211> LENGTH: 564
<212> TYPE: DNA
<213> ORGANISM: Homo sapiens

<400> SEQUENCE: 32
ccatggccgc aggcggcatc ctacacctgg agctgctggt ggccgtgggc cccgatgtct    60
tccaggctca ccaggaggac acagagcgct atgtgctcac caacctcaac atcggggcag   120
aactgcttcg ggacccgtcc ctggggctca gtttcgggt gcacctggtg aagatggtca   180
ttctgacaga gcctgagggt gctccaaata tcacagccaa cctcacctcg tccctgctga   240
gcgtctgtgg gtggagccag accatcaacc ctgaggacga cacggatcct ggccatgctg   300
acctggtcct ctatatcact aggttgacc tggagttgcc tgatggtaac cggcaggtgc   360
ggggcgtcac ccagctgggc ggtgcctgct ccccaacctg gagctgcctc attaccgagg   420
acactggctt cgacctggga gtcaccattg cccatgagat tgggcacagc ttcggcctgg   480
agcacgacgg cgcgccccgc agcggctgcg gccccagcgg acacgtgatg gcttcggacg   540
gcgccgcgcc ccgctgataa gctt                                          564

<210> SEQ ID NO 33
<211> LENGTH: 184
<212> TYPE: PRT
<213> ORGANISM: Homo sapiens

<400> SEQUENCE: 33

Met Ala Ala Gly Gly Ile Leu His Leu Glu Leu Leu Val Ala Val
1               5                   10                  15

Gly Pro Asp Val Phe Gln Ala His Gln Glu Asp Thr Glu Arg Tyr
                20                  25                  30

Val Leu Thr Asn Leu Asn Ile Gly Ala Glu Leu Leu Arg Asp Pro
                35                  40                  45

Ser Leu Gly Ala Gln Phe Arg Val His Leu Val Lys Met Val Ile
                50                  55                  60

Leu Thr Glu Pro Glu Gly Ala Pro Asn Ile Thr Ala Asn Leu Thr
                65                  70                  75

Ser Ser Leu Leu Ser Val Cys Gly Trp Ser Gln Thr Ile Asn Pro
                80                  85                  90

Glu Asp Asp Thr Asp Pro Gly His Ala Asp Leu Val Leu Tyr Ile
                95                  100                 105

Thr Arg Phe Asp Leu Glu Leu Pro Asp Gly Asn Arg Gln Val Arg
                110                 115                 120

```
Gly Val Thr Gln Leu Gly Gly Ala Cys Ser Pro Thr Trp Ser Cys
            125                 130                 135

Leu Ile Thr Glu Asp Thr Gly Phe Asp Leu Gly Val Thr Ile Ala
            140                 145                 150

His Glu Ile Gly His Ser Phe Gly Leu Glu His Asp Gly Ala Pro
            155                 160                 165

Gly Ser Gly Cys Gly Pro Ser Gly His Val Met Ala Ser Asp Gly
            170                 175                 180

Ala Ala Pro Arg

<210> SEQ ID NO 34
<211> LENGTH: 2529
<212> TYPE: DNA
<213> ORGANISM: Mus musculus

<400> SEQUENCE: 34
atgagccagc tttgcctgtg gttgacgtgc cagccttgtt atgctgtcag        50
tgtcagagga atcctcactg gtgccatctt cattctgggc tgctgggggc       100
tctctgactt ccagaagagt cttcttcaag atctggagcc caaggatgtg       150
tcttcttact ttggccacca tgctgctcca ttcacaggcc atcctccctc       200
tcacctccag agactgagac ggagaaggac tttggaggac attctgcacc       250
tggaactcct ggtagctgtg gccccgatg tttcccgggc tcatcaggag        300
gacacagaac gctacgtgct cactaatctc aatatcgggt cagaactgtt       350
gagaaaccca tccctgggag tccagttcca ggtgcacctg gtgaagctaa       400
tcaccctctc tgactcagag agtactccga atatcacggc caacatcacc       450
tcatccttga tgagcgtctg cgagtggagc cagacgatca accccacga        500
tgacagggat ccaagtcacg ctgacctgat tctctatatc accagcaacg       550
tggctggtgc cactgtcctt gtgattcatt ttctcttatc aaggttttgac      600
ctggagttgc ctgatggcaa ccagcaggtt cggggtgtca cccagctggg       650
aggtgcctgc tccctttcct ggagttgcct tatcactgag gatactggct       700
ttgacctggg ggtcaccatc gcccatgaga ttgggcacag cttcgggctg       750
gaccatgatg gtgctccagg tagtggcagc acctgcaagg ccagtggcca       800
cgtgatggcg gctgatggcg caacacctac tggagggacc ctggagtggt       850
ctgcctgcag ccaaaggcag ttgcagcacc tactcagcac agggcaaatg       900
cactgcttcc aggacccacc tgggctgcag tcaggactta cacggcacca       950
gctgatggca cagcctggcc tctactacag tgcagatgat cagtgccgtg      1000
tggcttttcgg ttctggggct gtcgcctgca ccttctccag ggagggtctg     1050
aacacagcac tcagtggtcc ttccaccttg atcctgtccg cagaccctg       1100
ccagaagtcc tggatggctc ctgaagctct caaattctcc ttctccacca      1150
aatccgacat ctggtctctg ggctgcatca ttctagacat ggccacttgc      1200
tccttcctga acgacacaga agccatgcaa ctgcggaagg ccatccgcca      1250
tcatccaggc agcctgaagc ccatcctgaa aaccatggag agaagcaaa       1300
tccctggtac agatgtctac tatttgcttc tgcccttcat gttgcatatc      1350
aaccccctccg atcgactggc aatcaaggat gtgatgcaag tcaccttcat    1400
gagcaactcc ttcaaaagct cctctgttgc gctgaatatg cagcggcaga     1450
```

-continued

| | |
|---|---|
| aggtccccat cttcatcact gacgtgctgc ttgaaggcaa catggccaac | 1500 |
| atcttaggtg atggcagctg gctgtgtgct tcctttgtga acgacagcag | 1550 |
| gcactgtgac tcagggattg gctcgcagag acttgggttt gattttcagt | 1600 |
| cagtctcttg gacagagcac cctctgaaag atgtcatgca gaatttctcc | 1650 |
| agtcgaccag aggtccagct cagagccatt aacaagttgt tgacaatgcc | 1700 |
| agaggaccag ctagcactgg caaaggaccc agaagctgag atcccaagga | 1750 |
| gcagtttgat catctccttc ctgatggata ccttgcggag ccatcctaac | 1800 |
| tctgaaaggc ttgttaatgt ggtctacaac gtgcttgcca ttatttccag | 1850 |
| ccaaggacag atctcagaag agctggaaga ggaggggttg tttcagcttg | 1900 |
| cccaagagaa cctggagcac ttccaagagg acagggacat ctgcctctct | 1950 |
| atcctgagcc tgctctggtc cctcctggta gatgttgtca ctgtggacaa | 2000 |
| agagcccttg gagcagctct ctggcatggt cacctgggtg ctggctactc | 2050 |
| atccggagga cgtggaaata gcagaggctg gctgtgcggt gctctggctg | 2100 |
| ctgtccttgt tgggctgcat aaaggagagt cagtttgagc aggtggtagt | 2150 |
| gctgctcctg agaagcatcc agctgtgccc tggcagagta ctgctggtga | 2200 |
| acaatgcatt ccgtggcttg gccagcctcg caaaggtgtc cggcccaccc | 2250 |
| tcacagttag agccaaatga ctgggtatcc agccccagcc cccttttgtg | 2300 |
| gaatcagaga cttcactatg tgaacaagca aaagctgttc atgcctctgt | 2350 |
| gggtgctgag gcaagagcac cctcattact gctgtgctaa tgaccctaca | 2400 |
| tcagagcaca tccaggcagt actaagtgga ctaaatgggt tgaaaagaa | 2450 |
| gcacagttgt gtggaatctt gtgtggaatg tggctgcagg cagcaggaga | 2500 |
| agaatagagg aggagcccca gggatttga | 2529 |

<210> SEQ ID NO 35
<211> LENGTH: 2514
<212> TYPE: DNA
<213> ORGANISM: Mus musculus

<400> SEQUENCE: 35

| | |
|---|---|
| aggaagctcc caagagtaaa cactgcctga tgtcccgccc agccagcaag | 50 |
| tgaacattgc acactaacca gaatcccagt cactagggct cctgtccggc | 100 |
| catcaactgc cttttctaaa gatgagccag ctttgcctgt ggttgacgtg | 150 |
| ccagccttgt tatgctgtca gtgtcagagg aatcctcact ggtgccatct | 200 |
| tcattctggg ctgctggggg ctctctgact tccagaagag tcttcttcaa | 250 |
| gatctggagc caaggatgt gtcttcttac tttggccacc atgctgctcc | 300 |
| attcacaggc catcctccct ctcacctcca gagactgaga cggagaagga | 350 |
| ctttggagga cattctgcac ctggaactcc tggtagctgt gggccccgat | 400 |
| gtttcccggg ctcatcagga ggacacagaa cgctacgtgc tcactaatct | 450 |
| caatatcggg tcagaactgt tgagaaaccc atccctggga gtccagttcc | 500 |
| aggtgcacct ggtgaagcta atcaccctct ctgactcaga gagtactccg | 550 |
| aatatcacgg ccaacatcac ctcatccttg atgagcgtct gcgagtggag | 600 |
| ccagacgatc aaccccacg atgacaggga tccaagtcac gctgacctga | 650 |

```
ttctctatat caccaggttt gacctggagt tgcctgatgg caaccagcag         700
gttcggggtg tcacccagct gggaggtgcc tgctcccttt cctggagttg         750
ccttatcact gaggatactg gctttgacct ggggtcacc atcgcccatg          800
agattgggca cagcttcggg ctggaccatg atggtgctcc aggtagtggc         850
agcacctgca aggccagtgg ccacgtgatg gcggctgatg gcgcaacacc         900
tactggaggg accctggagt ggtctgcctg cagccaaagg cagttgcagc         950
acctactcag cacagggcag atgcactgct tccaggaccc acctgggctg        1000
cagtcaggac ttacacggca ccagctgatg gcacagcctg gcctctacta        1050
cagtgcagat gatcagtgcc gtgtggcttt cggttctggg gctgtcgcct        1100
gcaccttctc cagggagggt ctggatgtat gccaggccct gtcctgccac        1150
acagaccccc tggaccaaag cagctgcagc cgcctccttg ttcctctcct        1200
ggatgggaca ggatgtggtg tggagaagtg gtgctccaag gctcgctgtc        1250
gctccctagc tgagctggct cctgtggctg cagtacatgg acactggtct        1300
agctggggcc cccatagtcc ctgctcccga tcctgtggag gaggtgtgat        1350
taccaggagg cggtggtgca caaccccag gcctgcattt gggggacgtg         1400
catgtgtggg tgaagacctc caggctaaga tgtgcaacac gcaggcttgt        1450
gagaagactc agctggagtt catgtccgag cagtgtgccc agacagacag        1500
acaaccactg caactttccc aaggcactgc ctccttctac cactgggatg        1550
ctgctgtgca gtatagtcaa ggagataccc tgtgcagaca catgtgctgg        1600
gctgttggag aaagcttcat tgtcagccgt ggggacaggt tcctagatgg        1650
gacccgttgt gtgccaagtg gtccccagga tgatgggacc ctaagcctct        1700
gtttgttggg cagctgcagg accttTggct gtgatggcag gatggactcc        1750
cagaaggttt gggatgcgtg ccaggtgtgt ggaggagaca acagcacctg        1800
cagctcacgg aatggttctt tcacagctgg gagagccaga gaatatgtca        1850
cgttcctgat tgttactccc aacatgacca acgcacacat tgtcaaccgc        1900
aggcctctct tcacacactt ggcggtgagg atccagggcc actacattgt        1950
ggcagggaag actagcatct cacccaacac cacctaccct tcccttctgg        2000
aggactaccg tgtggaatac agagtgactc tcactgagga ccagctgccc        2050
cacttagagg agattcacat ccggggaccc gtccggatg acattgagat         2100
tcaggtgtac agacgatatg gaggagaata tgggatctt acacacccag         2150
acatcacctt ttcctacttt caactgaagc agcaggcagc ctgggtatgg        2200
accgctaagc gtggaccctg ctcagtgagc tgtggggcag gctgcgctg         2250
ggtgacctac agctgccagg atcaagctca agacaagtgg gtaaagaacg        2300
cccagtgcca agggagccca cagccacctg catggcaaga gccttgtgtc        2350
tctgccccct gctccccata ttgggtagct ggggacttca gcccatgtag        2400
cgtgtcttgt ggcgggggcc ttcgggagcg tcactgcgc tgtgtagaga         2450
cccaagatgg cttcttaaag acactgccac ctgcccggtg cagagcagta        2500
gcccagcagc cagc                                               2514
```

<210> SEQ ID NO 36
<211> LENGTH: 3512

```
<212> TYPE: DNA
<213> ORGANISM: Mus musculus

<400> SEQUENCE: 36
aggaagctcc caagagtaaa cactgcctga tgtcccgccc agccagcaag        50
tgaacattgc acactaacca gaatcccagt cactagggct cctgtccggc       100
catcaactgc cttttctaaa gatgagccag ctttgcctgt ggttgacgtg       150
ccagccttgt tatgctgtca gtgtcagagg aatcctcact ggtgccatct       200
tcattctggg ctgctggggg ctctctgact tccagaagag tcttcttcaa       250
gatctggagc ccaaggatgt gtcttcttac tttggccacc atgctgctcc       300
attcacaggc catcctccct ctcacctcca gagactgaga cggagaagga       350 cttttggagga cattctgcac ctggaactcc tggtagctgt gggccccgat      400
gtttcccggg ctcatcagga ggacacagaa cgctacgtgc tcactaatct       450
caatatcggg tcagaactgt tgagaaaccc atccctggga gtccagttcc       500
aggtgcacct ggtgaagcta atcaccctct ctgactcaga gagtactccg       550
aatatcacgg ccaacatcac ctcatccttg atgagcgtct gcgagtggag       600
ccagacgatc aaccccacg atgacaggga tccaagtcac gctgacctga       650
ttctctatat caccaggttt gacctggagt tgcctgatgg caaccagcag       700
gttcggggtg tcacccagct gggaggtgcc tgctcccttt cctggagttg       750
ccttatcact gaggatactg gctttgacct gggggtcacc atcgcccatg       800
agattgggca cagcttcggg ctggaccatg atggtgctcc aggtagtggc       850
agcacctgca aggccagtgg ccacgtgatg gcggctgacg gcgcaacacc       900
cactggaggg accctggagt ggtctgcctg cagccaaagg cagttgcagc       950
acctactcag cacagggcaa atgcactgct tccaggaccc acctgggctg      1000
cagtcaggac ttacacggca ccagctgatg gcacagcctg gcctctacta     1050
cagtgcagat gatcagtgcc gtgtggcttt cggttctggg gctgtcgcct     1100
gcaccttctc cagggagggt ctggatgtat gccaggccct gtcctgccac     1150 acagaccct tggaccaaag cagctgcagc cgcctccttg ttcctctcct     1200
ggatgggaca gaatgtggtg tggagaagtg gtgctccaag gctcgctgtc     1250
gctccctagc tgagctggct cctgtggctg cagtacatgg acactggtct     1300
agctggggcc cccatagtcc ctgctcccga tcctgtggag gaggtgtgat     1350
taccaggagg cggtggtgca acaacccag gcctgcattt gggggacgtg     1400
catgtgtggg tgaagacctc caggctaaga tgtgcaacac gcaggcttgt     1450
gagaagactc agctggagtt catgtccgag cagtgtgccc agacagacag     1500
acaaccactg caactttccc aaggcactgc ctccttctac cactgggatg     1550
ctgctgtgca gtatagtcaa ggagatacc tgtgcagaca catgtgctgg     1600
gctgttggag aaagcttcat tgtcagccgt ggggacaggt tcctagatgg     1650
gacccgttgt gtgccaagtg gtcctcagga tgatgggacc ctaagcctct     1700
gtttgttggg cagctgcagg accttttggct gtgatggcag gatggactcc     1750
cagaaggttt gggatgcgtg ccaggtgtgt ggaggagaca acagcacctg     1800
```

| | |
|---|---|
| cagctcacgg aatggttctt tcacagctgg gagagccaga gaatatgtca | 1850 |
| cgttcctgat tgttactccc aacatgacca acgcacacat tgtcaaccgc | 1900 |
| aggcctctct tcacacactt ggcggtgagg atccagggcc actacattgt | 1950 |
| ggcagggaag actagcatct cacccaacac cacctaccct tcccttctgg | 2000 |
| aggactaccg tgtggaatac agagtgactc tcactgagga ccagctgccc | 2050 |
| cacttagagg agattcacat ccggggaccc gtccggatg acattgagat | 2100 |
| tcaggtgtac agacgatatg gaggagaata tggggatctt acacacccag | 2150 |
| acatcacctt ttcctacttt caactgaagc agcaggcagc ctgggtatgg | 2200 |
| accgctaagc gtggaccctg ctcagtgagc tgtggggcag ggctgcgctg | 2250 |
| ggtgacctac agctgccagg atcaagctca agacaagtgg gtaaagaacg | 2300 |
| cccagtgcca agggagccca cagccacctg catggcaaga gccttgtgtc | 2350 |
| tctgcccct gctccccata ttgggtagct ggggacttca gcccatgtag | 2400 |
| cgtgtcttgt ggcggggcc ttcgggacg gtcactgcgc tgtgtagaga | 2450 |
| cccaagatgg cttcttaaag acactgccac ctgcccggtg cagagcagta | 2500 |
| gcccagcagc cagcagcaga agtggaaaac tgcaactccc agccctgtcc | 2550 |
| caccaggtgg gaggtgtcag accctggccc ttgcatgcca tctgcctgtg | 2600 |
| aggcaggtct ggactcaagg aatgtgacat gtgtgtccag ggcgggtgac | 2650 |
| ccggagaagc cagaaactgc aggccctgc cgcaccgacg agatgtcagc | 2700 |
| tatgctggag ccctgctcca ggagcctgtg ttctccaggc ttgggtcagg | 2750 |
| tggacaacac catgtctctg ggcgaggagg ctccatcccc ggtgggcagt | 2800 |
| gacaagccag gggctcaggc tgagcatgtg tggaccctc tggtggggct | 2850 |
| gtgctccatc tcttgtggga gaggtctgaa ggaactgtat tcctgtgca | 2900 |
| tggattctgt cctcaaaatg cctgtccagg aagagctatg cggcttggct | 2950 |
| agtaagcccc caagccggtg ggaggtctgc agggctcgcc cctgtcctgc | 3000 |
| tcggtgggag actcaagtct tggcaccgtg cccggtgacc tgtggtgggg | 3050 |
| ggcgagtgcc actgtctgtt cgttgtgtgc agctagaccg tggccacccg | 3100 |
| atatctgtac ctcactccaa gtgctcgcca gtgcctaagc caggctcctt | 3150 |
| cgaggactgc agccctgagc cttgtcctgc tagggcacta gtgtgggaag | 3200 |
| ccgcccccac attcgccgtc acaagatggc gctgacatcc tgtgttctaa | 3250 |
| gttggtaaac aaataatctg cgcatgagcc aagggtattt acgactactt | 3300 |
| gtactctgtt tttcccgtga acgtcagctc ggccatgggc tgcagccaat | 3350 |
| cagggagtga tgcgtcctag gcaattgttg ttctctttta aatagaaggg | 3400 |
| gtttcgtttt tctctttttc ttgcttctta cactctggcc ccaaaagat | 3450 |
| gtaagcaata aagctttgcc gtaggaaaaa aaaaaaaaa ggatccggta | 3500 |
| cctctagatc ag | 3512 |

<210> SEQ ID NO 37
<211> LENGTH: 22
<212> TYPE: PRT
<213> ORGANISM: Homo sapiens

```
<400> SEQUENCE: 37

Phe Ser Pro Ala Pro Gln Pro Arg Arg Leu Leu Pro Gly Pro Gln
1               5                   10                  15

Glu Asn Ser Val Gln Ser Ser
            20

<210> SEQ ID NO 38
<211> LENGTH: 30
<212> TYPE: DNA
<213> ORGANISM: Homo sapiens

<400> SEQUENCE: 38
atgtgcaaca ctcaggcctg cgagaagacc                                    30

<210> SEQ ID NO 39
<211> LENGTH: 30
<212> TYPE: DNA
<213> ORGANISM: Homo sapiens

<400> SEQUENCE: 39
ccaacctgac cagtgtctac attgccaacc                                    30

<210> SEQ ID NO 40
<211> LENGTH: 21
<212> TYPE: DNA
<213> ORGANISM: Homo sapiens

<400> SEQUENCE: 40
ctggagccct gcccacctag g                                             21

<210> SEQ ID NO 41
<211> LENGTH: 62
<212> TYPE: DNA
<213> ORGANISM: Homo sapiens

<400> SEQUENCE: 41
gccgtcgact cttatcactt atcgtcatcg tccttgtagt cttgcgacat gaactccagc   60
tg                                                                  62

<210> SEQ ID NO 42
<211> LENGTH: 62
<212> TYPE: DNA
<213> ORGANISM: Homo sapiens

<400> SEQUENCE: 42
gccgtcgact cttatcactt atcgtcatcg tccttgtagt ccaggttggg ggtaactgtc   60
ag                                                                  62

<210> SEQ ID NO 43
<211> LENGTH: 62
<212> TYPE: DNA
<213> ORGANISM: Homo sapiens

<400> SEQUENCE: 43
gccgtcgact cttatcactt atcgtcatcg tccttgtagt ccacgtgtgc agcttgagcc   60
cc                                                                  62

<210> SEQ ID NO 44
<211> LENGTH: 62
<212> TYPE: DNA
<213> ORGANISM: Homo sapiens
```

```
-continued

<400> SEQUENCE: 44
gccgtcgact cttatcactt atcgtcatcg tccttgtagt ccctaggtgg gcagggctcc      60
ag                                                                     62

<210> SEQ ID NO 45
<211> LENGTH: 62
<212> TYPE: DNA
<213> ORGANISM: Homo sapiens

<400> SEQUENCE: 45
gccgtcgact cttatcactt atcgtcatcg tccttgtagt caccctgtcc cacacagggc      60
cc                                                                     62

<210> SEQ ID NO 46
<211> LENGTH: 60
<212> TYPE: DNA
<213> ORGANISM: Homo sapiens

<400> SEQUENCE: 46
tccaagcttg tcgactctta tcacttatcg tcatcgtcct tgtagtcggt tccttccttt      60

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 47
gactacaagg acgatgacga taagtga                                          27

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence:Synthetic

<400> SEQUENCE: 48

Asp Tyr Lys Asp Asp Asp Asp Lys
  1               5
```

VON WILLEBRAND FACTOR (VWF)—CLEAVING PROTEASE

This application is a Divisional of U.S. Ser. No. 10/475,538, filed Oct. 22, 2003, now U.S. Pat. No. 7,112,666, which is a 371 application of PCT/JP02/04141, filed Apr. 25, 2002, which claims priority from Japanese patent applications JP 2001-128342, filed Apr. 25, 2001, JP 2001-227510, filed Jul. 27, 2001, JP 2001-302977, filed Sep. 28, 2001 and JP 2002-017596, filed Jan. 25, 2002. The respective contents of the aforementioned applications are incorporated herein by reference.

TECHNICAL FIELD

The present invention relates to a plasma protein related to the field of medical drugs. More particularly, the present invention relates to a protease that specifically cleaves von Willebrand factor (it may be hereafter referred to as "vWF"), which is associated with blood coagulation. The vWF-cleaving protease of the present invention enables replacement therapy for patients with diseases resulting from defects or decreases in this protease, such as thrombotic thrombocytopenic purpura (it may be hereafter referred to as "TTP"). In addition, the use thereof as a novel antiplatelet thrombotic agent is expected.

BACKGROUND ART vWF is produced in vascular endothelial cells or megakaryocytes, and is a blood coagulation factor in which a single subunit comprising 2,050 amino acid residues (monomers of about 250 kDa) are bound by an S—S bond to form a multimer structure (with a molecular weight of 500 to 20,000 kDa). The level thereof in the blood is about 10 µg/ml, and a high-molecular-weight factor generally has higher specific activity.

vWF has two major functions as a hemostatic factor. One of the functions is as a carrier protein wherein vWF binds to the blood coagulation factor VIII to stabilize it. Another function is to form platelet plug by adhering and agglomerating platelets on the vascular endothelial subcellular tissue of a damaged vascular wall.

Thrombotic thrombocytopenic purpura is a disease that causes platelet plug formation in somatic arterioles and blood capillaries throughout the whole body. In spite of recent advances in medical technology, the morbidity associated with this disease approximately tripled from 1971 to 1991. Pathologically, TTP is considered to result from vascular endothelial cytotoxicity or vascular platelet aggregation. Immunohistologically, a large amount of vWFs are recognized in the resulting platelet plugs, and vWF is considered to play a major role in causing them. A normal or high-molecular-weight vWF multimer structure is dominant in a TTP patient, and an unusually large vWF multimer (ULvWFM) or large vWF multimer (LvWFM) is deduced to play a major role in accelerating platelet aggregation or microthrombus formation under high shearing stress. In contrast, vWF was known to degrade at a position between residues Tyr 842 and Met 843 by the action of vWF-cleaving protease in the circulating blood of a healthy person under high shearing stress. Accordingly, TTP is considered to occur in the following manner. The protease activity in the plasma is lowered for some reason, and ULvWFM to LvWFM are increased to accelerate platelet aggregation. This forms platelet plugs in blood vessels.

Recently, Furlan et al. (Blood, vol. 87, 4223-4234: 1996, JP Patent Publication (Kohyo) No. 2000-508918) and Tsai et al. (Blood, vol. 87, 4235-4244: 1996) developed a method for assaying vWF-specific cleaving protease. In their report, this protease activity was actually lowered in TTP. The aforementioned authors reported that this enzyme was metalloprotease in the plasma and partially purified. However, they have not yet succeeded in the amino acid sequencing which would specify the protease. There have been no further developments since then.

DISCLOSURE OF THE INVENTION

Up to the present, plasmapheresis therapy has been performed for treating patients who congenitally lack vWF-specific cleaving protease and patients who had acquired positive antibodies against this protease. Establishment of replacement therapy using purified products or a pure substance such as a recombinant gene product of the aforementioned protease is desired. Familial TTP patients congenitally lack vWF-specific cleaving protease, and non-familial TTP is caused by posteriori production of autoantibodies against the aforementioned protease. Accordingly, replacement therapy for this protease is preferable for familial TTP patients (plasma administration is actually performed), and removal of autoantibodies by plasmapheresis and substitution of this protease are necessary for non-familial TTP. Further, the use of this protease as a novel antiplatelet thrombotic agent can also be expected.

As mentioned above, however, Furlan et al. (Blood, vol. 87, 4223-4234: 1996, JP Patent Publication (Kohyo) No. 2000-508918) and Tsai et al. (Blood, vol. 87, 4235-4244: 1996) have suggested that the vWF-cleaving protease was metalloprotease in the plasma. It was reported to be partially purified, and concentrated 1,000- to 10,000-fold from the plasma in terms of its specific activity. Even under these conditions, there has been no advancement in the analysis of the properties of this protease, such as the amino acid sequence of its protein, over the period of roughly 5 years that has passed since then. No specific biological information has yet been obtained regarding this protease. As reported by Furlan et al., the protein of interest is supposed to be gigantic, and there may be various problems associated therewith. For example, diversified forms of this protease, such as various interacting molecules or cofactors, are expected. Based on the complexity of purification processes, deteriorated capacity of separation by nonspecific interaction during the purification step, and other factors, it is deduced to be very difficult to isolate and identify the protease from a plasma fraction by the purification process according to Furlan et al.

Under the above circumstances, the present inventors have conducted concentrated studies in order to isolate and identify the vWF-cleaving protease. As a result, they have succeeded in isolating and purifying the vWF-cleaving protease of interest, which had not yet been reported. Thus, they have succeeded in identifying an amino acid sequence of the mature protein and a gene encoding this amino acid sequence.

The vWF-cleaving protease of the present invention can cleave a bond between residues Tyr 842 and Met 843 of vWF. According to one embodiment, this protease has a molecular weight of 105 to 160 kDa or 160 to 250 kDa in SDS-PAGE under reducing or non-reducing conditions. It is comprised of a polypeptide chain having Leu-Leu-Val-Ala-Val (SEQ ID NO: 1) as a partial sequence. More preferably, it is comprised of a polypeptide chain having the partial N-terminal amino acid sequence of a mature protein, i.e., Ala-Ala-Gly-Qly-Ile-Leu-His-Leu-Glu-Leu-Leu-Val-Ala-Val (SEQ ID NO: 2). It is a novel substance characterized by the following properties.

1) vWF-Cleaving Activity

According to the N-terminal sequence analysis of the cleavage fragment, the protease of the present invention cleaves a peptide bond between residues Tyr 842 and Met 843.

2) Fractionation by Gel Filtration

When fractionation is performed by gel filtration chromatography using FI paste as a starting material, most activities are collected in a fraction with a molecular weight of 150 to 300 kDa. According to one embodiment of the present invention, an actually obtained active substance is found to have a molecular weight of about 105 to 160 kDa in electrophoresis. Accordingly, the protease of the present invention is a substance that is likely to form a dimer or the like or to bind to another molecule or a substance that can be easily degraded or can have a heterogeneous sugar chain added.

3) Ammonium Sulfate Precipitation

For example, when FI paste is used as a starting material, a large portion of this protease is recovered as a precipitation fraction from a roughly purified fraction with the use of 33% saturated ammonium sulfate.

4) SDS-PAGE

For example, the protease of the present invention derived from FI paste prepared from pooled human plasma or cryoprecipitate mainly has a molecular size of about 105 to 160 kDa determined by a molecular weight marker in SDS-PAGE. Based on the nucleic acid sequence as shown in SEQ ID NO: 15, when an amino acid sequence represented by a frame between an atg initiation codon at position 445 and a tga termination codon at position 4726 is expressed by gene recombination, there are some variations in molecular sizes depending on a host. However, a molecular size of about 160 to 250 kDa determined by a molecular weight marker is exhibited. This size is observed in the plasma of healthy humans and in that of some TTP patients. Several molecular species of this protease are present in human plasma, caused by the presence of alternative splicing products (SEQ ID NOs: 16 to 21) recognized at the time of gene cloning, differences in post-translational modification such as sugar chain addition, or degradation during purification. Further, this protease could be partially recovered in an active state after SDS-PAGE under non-reducing conditions.

5) Analysis of Amino Acid Sequence

The amino acid sequence of the isolated polypeptide fragment was analyzed. This presented an example of a polypeptide chain having a sequence Leu-Leu-Val-Ala-Val (SEQ ID NO: 1) as a partial amino acid sequence and a sequence Ala-Ala-Gly-Gly-Ile-Leu-His-Leu-Glu-Leu-Leu-Val-Ala-Val (SEQ ID NO: 2) as a N-terminal amino acid sequence of a mature protein. Further, with current bioinformatics (BIOINFORMATICS: A Practical Guide to the Analysis of Genes and Proteins, edited by Andreas D. Baxevanis and B. F. Francis Ouellette), a nucleic acid sequence encoding the amino acid sequence was highly accurately identified by searching a database based on the aforementioned partial sequence. More specifically, the genome database was searched by the tblastn program. This identified a chromosome clone (AL158826) that is deduced to encode the protease of the present invention. Further, clones (AI346761 and AJ011374) that are deduced to be a part of the protease of interest and a part of the polypeptide to be encoded by the aforementioned genome were identified through collation with the Expressed Sequence Tag (EST) database. Based thereon, the amino acid sequence as shown in SEQ ID NO: 3 or 7 was identified as an active vWF-cleaving protease site.

GCT GCA GGC GGC ATC CTA CAC CTG GAG CTG CTG GTG GCC GTG (SEQ ID NO: 5), a sequence deduced from the genome, and more preferably CTG CTG GTG GCC GTG (SEQ ID NO: 4), a portion thereof, the transcriptome of which was confirmed by EST, was obtained. The obtained nucleotide sequence was analyzed, and motif analysis was carried out based on the deduced sequence. As a result, it was found to have a metalloprotease domain as a candidate for the protease of the present invention. Based on the above findings, it became possible to disclose a sequence of a polypeptide chain as a more specific example of the protease. Also, activities of proteases are generally known to vary depending on, for example, substitution, deletion, insertion, or introduction of point mutation into a portion of the amino acid sequence (Blood coagulation factor VII mutants, Soejima et al., JP Patent Publication (Kokai) No. 2001-61479 A). Similarly, the protease of the present invention can be modified by, for example, deletion, substitution, or addition of one or several amino acids, to prepare optimized proteases.

The protease proteins were further mass-produced, and 29 amino acid sequences from the N-terminus were determined. These amino acid sequences are shown in SEQ ID NO: 8. This result is substantially the same as the sequence as shown in SEQ ID NO: 3 or 7 deduced by bioinformatics. Only one difference is that the amino acid 27th in SEQ ID NO: 3 or 7 was Glu while it was Arg according to the present analysis of the N-terminal sequence. This was considered to be a gene polymorphism. Thus, this protease was confirmed to be comprised of a polypeptide chain having the amino acid sequence as shown in SEQ ID NO: 3 or 7 at its N-terminus as a mature unit. A gene fragment encoding this protease was then cloned in the following manner.

Based on the nucleic acid sequence as shown in SEQ ID NO: 6, a sense primer (SEQ ID NO: 9) and an antisense primer (SEQ ID NO: 10) were prepared based on the nucleic acid sequence underlined in FIG. 9, and a gene sandwiched between these primers was amplified. This hgment was cloned, and the nucleotide sequence was then confirmed. This hgrnent was used as a probe for Northern blotting to analyze the site at which the protease gene was expressed. As a result, this protease gene was found to be expressed mainly in the liver. Accordingly, the human liver cDNA library was purchased, and a gene encoding this protease was identified using a rapid amplification of cDNA ends (RACE) technique. Based on these results, in the case of the largest sequence of approximately 5 kb of mRNA (cDNA) reaching the poly(A) addition site as shown in SEQ ID NO: 15 was identified.

Based on the amino acid sequence deduced from this gene sequence, this protease was deduced to have a preprosequence, and to belong to the disintegrin and metalloprotease (ADAM) family having a disintegrin-like domain, a metalloprotease domain, and the like, and particularly to the ADAM-TS family having a thrombospondin Type-1 (TSP-1) domain. Finally, including those having insertion or deletion in a part of the nucleic acid sequence (SEQ ID NOS 15 and 55-59), isoforms as shown in SEQ ID NOS: 16 to 21 having sequences as shown in SEQ ID NOS: 3 and 7 at the N-terminuses after the mature preprosequence has been cleaved were identified. Thus, the protease of the present invention should cleave vWF between residues Tyr 842 and Met 843 and should have the Leu-Leu-Val-Ala-Val (SEQ ID NO: 1) sequence as a partial amino acid sequence.

The vWF-cleaving protease of the present invention can be generally prepared by the following process.

According to the present invention, a process for assaying the protease activity is characterized by the possibility of evaluating activity within a short period of time. According to the report by Furlan et al. (Blood, vol. 87, 4223-4234: 1996, JP Patent Publication (Kohyo) No. 2000-508918 A), activity is assayed by analyzing vWF-cleaving patterns by Western blotting using the anti-vWF antibody, and thus, it takes time to transfer the protease to a filter. More specifically, this process requires approximately at least 45 hours in total, i.e., 24 hours for the enzymatic reaction with a substrate vWF, 17 hours for electrophoresis, and 3 hours to transfer the protease to a filter, followed by detection using the anti-vWF antibody. In contrast, the present inventors completed activity assay in 18 hours in total, i.e., 16 hours for the enzymatic reaction with a substrate vWF, and 2 hours for electrophoresis and detection. This indicates that the time required for the assay can be reduced to one third or less of that required for the conventional assay. This can also shorten the time required for the purification process, and in turn can lower the degree of the protease to be inactivated. Accordingly, purification efficiency is improved compared with that attained by the method of Furlan et al., and as a result, the degree of purification is also enhanced.

Further, the starting material was examined using the aforementioned assay system. As a result, it was found that the protease activity was more concentrated in FI paste than in the cryoprecipitate that had been reported by Furlan et al. in the past. FI paste was used as a starting material, and the aforementioned rapid activity assay systems were combined. This enabled isolation and identification of the protease of interest. In a specific embodiment, a purification process combining gel filtration chromatography with ion exchange chromatography is employed, and the aforementioned activity assay system is also combined.

More specifically, FI paste is solubilized with a buffer, and the resultant is fractionated by gel filtration chromatography. The protease activity is fractionated at the elution region with a molecular weight of 150 to 300 kDa deduced from the size marker of gel filtration. Thereafter, the resultant is precipitated and concentrated using 33% saturated ammonium sulfate. This procedure is repeated three times in total. The active fraction obtained in the third gel filtration is pooled, and the resultant is subjected to dialysis at 4° C. overnight with a buffer comprising 50 mM NaCl added to 50 mM Tris-HCl (pH 7.1). Thereafter, the dialysis product is subjected to anion exchange chromatography (DEAE) and eluted stepwise with 0.25 M NaCl. The present inventors have conducted concentrated studies in order to find a process for isolating and identifying the protease of the present invention. As a result, they found that, surprisingly, the protease was recoverable as an active band after non-reducing SDS-PAGE. In order to achieve further mass production, the purified and concentrated fraction was applied to the Biophoresis utilizing the principle of SDS-PAGE. Thus, a fraction having vWF-cleaving activity was isolated from the electrophoresed fraction. According to the approximate calculation of the specific activity up to this phase, purification of about 30,000- to 100,000-fold was achieved. This procedure was efficiently and rapidly repeated several times, and thus, about 0.5 pmole of sample that is the current limit of the analysis of amino acid sequence was obtained. Thus, analysis of amino acid sequence became feasible. More specifically, a final step of separation and purification (Biophoresis) based on the principle of SDS-PAGE is important, and it is based on the findings as a result of concentrated studies, which had led to the completion of the present invention.

According to the report by Furlan et al., specific activity was improved by as much as about 10,000 times, although the protease was not substantially isolated or identified. This could be because of deactivation during purification or the difficulty of isolating and identifying molecules, which were gigantic proteins capable of interacting with various other proteins such as the protease of the present invention by a separation method utilizing various types of liquid chromatography. Further, the protease content in the plasma was deduced to be very small, and thus, it was necessary to await the establishment of the process according to the present invention. Furthermore, the use of this process enables the purification of recombinant genes.

Based on the findings of the present invention, peptides or proteins prepared from the obtained sequences are determined to be antigens. With the use thereof, a monoclonal antibody, a polyclonal antibody, or a humanized antibody thereof can be prepared by general immunization techniques (Current Protocols in Molecular Biology, Antibody Engineering: A PRACTICAL APPROACH, edited by J. McCAFFERTY et al. or ANTIBODY ENGINEERING second edition, edited by Carl A. K. BORREBAECK). Alternatively, an antibody that binds to the aforementioned protein can be prepared by antibody-producing techniques utilizing phage display (Phage Display of Peptides and Proteins: A Laboratory Manual, edited by Brian K. Kay et al., Antibody Engineering: A PRACTICAL APPROACH, edited by J. McCAFFERTY et al. or ANTIBODY ENGINEERING second edition, edited by Carl A. K. BORREBAECK). Alternatively, based on these techniques, a neutralizing antibody acting against the protease activity or a simple binding antibody can be isolated from a specimen from a TTP patient who has an autoantibody positive against this protease. These antibodies can be applied to diagnosis and therapy of diseases such as TTP.

Based on the obtained genome or EST sequence, cDNA or a genomic gene encoding the protease of the present invention can be cloned by a common technique (Molecular Cloning, 2nd edition). Further, bioinformatics techniques (BIOINFORMATICS: A Practical Guide to the Analysis of Genes and Proteins, edited by Andreas D. Baxevanis and B. E Francis Ouellette) enable cloning of the proteins of other animal species that are homologous thereto, and the resultant gene is fractured by a common technique (for example, Gene Targeting: A Practical Approach, First Edition, edited by A. L. Joyner, Teratocarcinomas and embryonic stem cell a practical approach) to produce TTP-like animal models. In particular, the identification of the gene sequence encoding the protein derived from a mouse enables the production of a knockout mouse having this gene. Thus, a disease mouse model of congenital TTP or the like can be prepared.

In accordance with a common technique (for example, J. Sambrook et al., Molecular Cloning, 2nd edition, or CURRENT PROTOCOLS IN MOLECULAR BIOLOGY), these genes are incorporated into a suitable expression vector, the resultant is transformed into a suitable host cell, and the gene recombinant product of the protease can be thus prepared. In this case, the gene to be incorporated is not necessarily the one that encoded the entire region of the protein. It also includes a partial expression of the protein as defined by a domain depending on its usage.

For example, the polynucleotide according to the present invention is introduced into a host cell using a conventional technique such as transduction, transfection, or transformation. The polynucleotide is introduced solely or together with another polynucleotide. Another polynucleotide is introduced independently, simultaneously, or in combination with the polynucleotide of the present invention.

For example, the polynucleotide of the present invention is transfected in a host cell, such as a mammalian animal cell, by a standard technique for simultaneous transfection and selection using another polynucleotide encoding a selection marker. In this case, the polynucleotide would be generally stably incorporated in the genome of the host cell.

Alternatively, the polynucleotide may be bound to a vector comprising a selection marker for multiplication in a host. A vector construct is introduced to a host cell by the aforementioned technique. In general, a plasmid vector is introduced as DNA of a precipitate, such as a calcium phosphate precipitate, or a complex with a charged lipid. Electroporation is also employed for introducing the polynucleotide into a host. When the vector is a virus, this virus is packaged in vitro or introduced into a packaging cell, thereby introducing the packaged virus into a cell.

Extensive techniques that are suitable for producing a polynucleotide and introducing the resulting polynucleotide to a cell in accordance with this embodiment of the present invention are known and common in the art. Such techniques are described in Sambrook et al. (aforementioned), and this document explains a variety of standard experimental manuals describing the aforementioned techniques in detail. In respect of this embodiment of the present invention, the vector is, for example, a plasmid vector, a single- or double-stranded phage vector, or a single- or double-stranded RNA or DNA viral vector. Such a vector is introduced into a cell as a polynucleotide, and preferably as DNA by a common technique for the introduction of DNA or RNA into a cell. When the vector is a phage or virus, the vector is preferably introduced to the cell as a packaged or sealed virus by a known technique for infection and transduction. A viral vector may be of a replication-competent or defective type.

A preferable vector is a vector which expresses the polynucleotide or polypeptide of the present invention in points. In general, such a vector comprises a cis-action control region that is effective for the expression in a host operably bound to the polynucleotide to be expressed. When a suitable trans-action factor (for example, a group of proteases involved with the post-translational processing such as signal peptidase or Furin) is introduced in a host cell, it is supplied by a host, a complementary vector, or the vector itself.

In a preferable embodiment, a vector provides specific expression. Such specific expression is an inducible one or realized only in a certain type of cell. Alternatively, it is an inducible and cell-specific expression. A particularly preferable inducible vector can induce expression by an easily operable environmental factor such as temperature or a nutritional additive. Various vectors suitable for this embodiment including a construction for the use in prokaryotic and eukaryotic cell hosts and an inducible expression vector are known, and persons skilled in the art can commonly use them.

A genetically engineered host cell can be cultured in general nutrient medium, and it is modified to be particularly suitable for activation of promoter, selection of transformant, or amplification of a gene. In general, it would be obvious to persons skilled in the art that conventional culture conditions such as temperature or pH level for host cells selected for the expression are suitable for the expression of the polypeptide of the invention.

A wide variety of expression vectors can be used for expressing the polypeptide of the present invention. Examples of these vectors include chromosome, episome, and virus-derived vectors. These vectors are derived from bacterial plasmid, bacteriophage, yeast episome, yeast chromosome element, or viruses such as baculovirus, papovavirus such as simian virus 40 (SV40), vaccinia virus, adenovirus, fowlpox virus, pseudorabies virus, or retrovirus. A vector derived from a combination of the aforementioned, for example, a vector derived from plasmid and bacteriophage gene element, more specifically, a cosmid or phagemid, may also be used. They are used for the expression in accordance with this embodiment of the present invention. In general, since polypeptides were expressed in hosts, any vector that is suitable for maintaining, multiplying, or expressing a polynucleotide can be used for the expression according to the aforementioned embodiment. A suitable DNA sequence is inserted into a vector by various conventional techniques. In general, a DNA sequence for expression is bound to an expression vector by cleavage of a DNA sequence and an expression vector having 1 or more restriction endonucleases, and a restriction fragment is then bound together using T4 DNA ligase. Restriction and ligation techniques that can be used for the above purpose are known and common to persons skilled in the art. With regard thereto, Sambrook et al. (aforementioned) very precisely describe another suitable method for constructing an expression vector utilizing another technique known and common to persons skilled in the art.

A DNA sequence in the expression vector is operably bound to, for example, a suitable expression-regulating sequence including a promoter to orient the mRNA transcription. A few examples of known representative promoters are the phage lambda PL promoter, *E. Coli* lac, trp, trc, and tac promoters, SV40 early and late promoters, and the retrovirus LTR promoter. Many promoters that are not described are suitable for the use according to the embodiment of the present invention, known, and more easily used as described in the examples of the present invention. In general, an expression construct comprises a ribosome binding site for translation in a transcription initiation or termination site or a transcribed domain. The coding region of the mature transcript that was expressed by the construct comprises the initiation AUG at the initiation and termination codons located substantially at the terminus of polypeptide to be translated. In addition, the construct comprises a regulator region that regulates and induces the expression. In general, such a region is activated through the regulation of the repressor binding site, transcription of an enhancer, or the like in accordance with various conventional methods.

Vectors for multiplication and expression include selection markers. Such markers are suitable for multiplication, or they comprise additional markers for the above-stated purpose. The expression vector preferably comprises one or more selection marker genes to provide phenotypic traits for the purpose of selecting the transformed host cell. A preferable marker includes dihydrofolate reductase- or neomycin-resistance with regard to eukaryotic cell culture. It has tetracycline- or ampicillin-resistance with regard to *E. coli* and other bacterial cultures. A suitable vector comprising a DNA sequence and a suitable promoter or regulatory sequence as described herein are introduced to a suitable host by various suitable known techniques for the expression of the polypeptide of interest.

Representative examples of suitable hosts include: bacterial cells such as *E. coli, Streptomyces*, and *Salmonella typhimurium*; fungal cells such as a yeast cell; insect cells such as *drosophila* S2 and *Spodoptera* Sf9 cells; and adhesive or floating animal or plant cells such as CHO, COS, Bowes melanoma cells, and SP2/0. Various hosts for expression constructs are known, and persons skilled in the art can easily select a host for expressing polypeptides in accordance with this embodiment based on the disclosure of the present invention.

More specifically, the present invention includes a recombinant construct, such as an expression construct comprising one or more sequences as mentioned above. The construct is a vector, such as a plasmid or viral vector comprising the sequence of the present invention inserted therein. The sequence is inserted in a positive or negative direction. In a preferable specific example thereof, the construct further has a regulatory sequence comprising a promoter or the like that is operably bound to the sequence. Various suitable vectors and promoters are known to persons skilled in the art, and there are many commercially available vectors that are suitably used in the present invention.

Commercially available vectors are exemplified below. Vectors that are preferably used for bacteria are pQE70, pQE60, and pQE-9 (Qiagen); pBS vector, PhageScript vector, Bluescript vector, pNH8A, pNH16a, pNH18A, and pNH46A (Stratagene); and ptrc99a, pKK223-3, pKK233-3, pDR540, and pRIT5 (Pharmacia). Examples of preferable eukaryotic vectors are pWLNEO, pSV2CAT, pOG44, pXT1, and pSG (Stratagene) and pSVK3, pBPV, pMSG, and pSVL (Pharmacia). These vectors are commercially available for persons skilled in the art to be used in accordance with the embodiment of the present invention, and they are merely a list of known vectors. For example, other plasmids or vectors suitable for introducing, maintaining, multiplying, or expressing the polynucleotide or polypeptide of the present invention can also be used in hosts in accordance with this embodiment of the present invention.

A promoter region can be selected from a gene of interest using a vector comprising, for example, a candidate promoter fragment, i.e., a reporter transcription unit lacking a promoter region such as a chloramphenicol acetyl transferase (CAT) transcription unit located downstream of restriction sites for introducing promoter-containing fragments. As known to the public, the introduction of the promoter-containing fragment into the vector at the restriction site located upstream of the cat gene generates CAT activity that can be detected by standard CAT assay. A vector that is suitable for this purpose is known and readily available. Examples of such vectors are pKK232-8 and pCM7. Accordingly, the promoter for expressing the polynucleotide of the present invention includes not only a readily available known promoter but also a promoter that can be readily obtained using a reporter gene in accordance with the aforementioned technique.

Among them, according to the present invention, examples of known bacterial promoters that are suitably used to express polynucleotides and polypeptides are *E. coli* lacI and lacZ promoters, T3 and T7 promoters, gpt promoter, lambda PR and PL promoters, and trp and trc promoters. Examples of suitable known eukaryotic promoters include the Cytomegalovirus (CMV) immediate promoter, the HSV thymidine kinase promoter, early and late SV40 promoters, a retrovirus LTR promoter such as the Rous sarcoma virus (RoSV) promoter, and a metallothionein promoter such as the metallothionein-I promoter.

Selection of a vector and a promoter suitable for expression in a host cell is a known technique. Techniques necessary for the construction of expression vectors, introduction of a vector in a host cell, and expression in a host are common in the art. The present invention also relates to a host cell having the aforementioned construct. A host cell can be a higher eukaryotic cell such as a mammalian animal cell, a lower eukaryotic cell such as a yeast cell, or a prokaryotic cell such as a bacterial cell.

The construct can be introduced in a host cell by calcium phosphate transfection, DEAE-dextran-mediated transfection, cationic lipid-mediated transfection, electroporation, transduction, infection, or other methods. These methods are described in a variety of standard laboratory manuals, such as a book by Sambrook et al.

The construct in a host cell can be used by a conventional method, and it produces a gene product encoded by a recombinant sequence. Alternatively, a partial polypeptide of the present invention can be synthesized using a general peptide synthesizer. A mature protein can be expressed under the control of a suitable promoter in a mammalian animal, yeast, bacterial, or other cell. Also, such a protein can be produced in a cell-free translation system with the use of RNA derived from the DNA construct of the present invention. Suitable cloning and expression vectors for prokaryotic and eukaryotic hosts are described in Sambrook et al (aforementioned).

In general, a recombinant expression vector comprises: a replication origin; a promoter derived from a highly expressed gene to orient the transcription of a downstream structural sequence; and a selection marker for bringing the cell into contact with a vector and isolating the vector-containing cell. A suitable promoter can be induced from a gene encoding glycolytic enzymes such as 3-phosphoglycerate kinase (PGK), α-factor, acid phosphatase, and heat shock protein. A selection marker includes *E. coli* ampicillin-resistant gene and *S. cerevisiae* trp1 gene.

Transcription of DNA encoding the polypeptide of the present invention using a higher eukaryotic cell may be enhanced by inserting an enhancer sequence in a vector. The enhancer is generally a cis-acting element for DNA for enhancing the promoter transcription activity in the predetermined host cell. Examples of an enhancer include the SV40 enhancer, the Cytomegalovirus early promoter/enhancer, the polyoma enhancer behind the replication origin, the β-actin enhancer, and the adenovirus enhancer.

The polynucleotide of the present invention encoding a heterologous structural sequence of the polypeptide of the present invention is generally inserted in a vector by standard techniques in such a manner that it is operably bound to the expression promoter. The transcription initiation site of the polypeptide is suitably located at the 5' site of the ribosome binding site. The ribosome binding site is 5' relative to AUG that initiates the translation of a polypeptide to be expressed. In general, an initiation codon starts from AUG and another open reading frame located between the ribosome binding site and initiation AUG is not present. The termination codon is generally present at the terminus of the polypeptide, and the adenylation signal and the terminator are suitably located at the 3' end of the transcription region.

Regarding the secretion of the translated protein in the ER lumen, in the cytoplasm, or to the extracellular environment, a suitable secretion signal is incorporated in the expressed polypeptide. The signal may be endogenous or heterologous to the polypeptide.

Further, a prosequence subsequent to the signal sequence may be endogenous or heterologous (e.g., a preprosequence of another metalloprotease).

The polypeptide is expressed in a modified form such as a fusion protein, and it includes not only a secretion signal but also an additional heterologous functional region. Accordingly, an additional amino acid, especially a charged amino acid region, or the like, is added to the polypeptide to improve stability and storage stability in the host cell during purification or subsequent operation and storage. Alternatively, a given region may be added to the polypeptide to accelerate the purification. This type of region may be removed before the final preparation of polypeptides. Induction of secretion or excretion, stability improvement, or facilitation of purification with the addition of a peptide portion to the polypeptide is a technique common and known in the art.

Examples of prokaryotic hosts that are suitable for multiplying, maintaining, or expressing the polynucleotide or polypeptide of the present invention include *E. coli, Bacillus subtilis*, and *Salmonella typhimurium*. Various types of *Pseudomonas, Streptomyces*, and *Staphylococcus* are suitable hosts in this respect. Furthermore, various other types of hosts known to persons skilled in the art can be also used. Representative examples of expression vectors that are useful for bacterial applications include, but are not limited to, the replication origin of bacteria derived from commercially available plasmid including a selectable marker and a gene element of a known cloning vector pBR322 (ATCC 37017). Examples of such commercially available vectors include pKK223-3 (Pharmacia Fine Chemicals, Uppsala, Sweden) and GEM1 (Promega Biotec, Madison, Wis., USA). These pBR322 (main chain) sections are combined with a suitable promoter and structural sequences to be expressed.

Host cells are suitably transformed and multiplied to the optimal cell concentration. Thereafter, the selected promoter is induced by a suitable means (e.g., temperature shifting or chemical inducer), and cells are further cultured. Typically, cells are collected by centrifugation and fractured by a physical or chemical means. The resulting crude extract is further purified. Microbial cells used for the protein expression can be fractured by any convenient means selected from a freezing-thawing cycle, ultrasonication, mechanical fracture, and the use of a cytolytic agent. These methods are known to persons skilled in the art.

Various cell lines for mammalian animal cell culture can be also used for the expression. An example of a cell line for mammalian animal expression includes a monkey kidney fibroblast COS-6 cell described in Gluzman et al., Cell 23:175 (1981). Examples of other cells that are capable of expressing compatible vectors include C127, 3T3, CHO, HeLa, human kidney 293, and BHK cells. Further, a floating myeloma cell line such as SP2/0 can be also used.

A mammalian animal expression vector comprises a replication origin, a suitable promoter and enhancer, a necessary ribosome binding site, a polyadenylation site, splice donor and acceptor sites, a transcription termination sequence, and a 5' franking untranscribed sequence necessary for expression. DNA sequences derived from the SV40 splice site and the SV40 polyadenylation site are used for the non-transformed or transcribed gene element of interest. An example thereof is a CAG expression vector (H. Niwa et al., Gene, 108, 193-199 (1991)).

Based on the gene sequence of the above protease, a probe, primer, or antisense is designed by a common technique. The antisense technique can be used for controlling gene expression by the use of antisense DNA or RNA or the formation of a triple helix. This technique is described in, for example, Okano, J., Neurochem., 56: 560 (1991); OLIGODEOXYNUCLEOTIDES AS ANTISENSE INHIBITORS OF GENE EXPRESSION, CRC Press, Boca Raton, Fla. (1988). The triple helix formation is examined in, for example, Lee et al., Nucleic Acids Research 6: 3073 (1979); Cooney et al., Science 241:456(1988); and Dervan et al., Science 251:1360(1991). The method is based on the polynucleotide bond with complementary DNA or RNA. This enables the gene diagnosis or gene therapy.

For example, cells obtained from a patient are subjected to ex vivo genetic engineering using a polynucleotide such as polypeptide-encoding DNA or RNA. The resulting cells are then supplied to patients who should be treated with polypeptides. For example, cells can be subjected to ex vivo genetic engineering using a retrovirus plasmid vector comprising RNA encoding the polypeptide of the present invention. Such a technique is known in the art, and the use thereof in the present invention is obvious according to the description given herein. Similarly, cells are subjected to in vitro genetic engineering in accordance with a conventional process in respect of in vivo polypeptide expression. For example, the polynucleotide of the present invention is genetically engineered for expression in the replication-deficient retrovirus vector as mentioned above. Subsequently, the retrovirus expression construct is isolated, introduced to a packaging cell, and transduced using a retrovirus plasmid vector comprising RNA encoding the polypeptide of the present invention. Thus, the packaging cell produces infectious viral particles having a control gene. These producer cells are subjected to in vitro genetic engineering and then administered to patients to allow polypeptides to be expressed in vivo. This administration method and other methods for administering polypeptides according to the present invention would be clearly understood by persons skilled in the art based on the teaching of the present invention.

Examples of the aforementioned retrovirus, from which the retrovirus plasmid vector is derived, include, but are not limited to, Moloney murine leukemia virus, spleen necrosis virus, Rous sarcoma virus, Harvey sarcoma virus, avian leukosis virus, gibbon leukemia virus, human immunodeficiency virus, myeloproliferative sarcoma virus, and mammary tumor virus. This type of vector comprises one or more promoters to express polypeptides. Examples of suitable promoters that can be used include, but are not limited to, retrovirus LTR, SV40 promoter, CMV promoter described in Miller et al., Biotechniques 7: 980-990 (1989), and other promoters (e.g., cell promoters such as a eukaryotic cell promoter including, but not limited to, histone, RNA polymerase III, and β-actin promoter). Examples of other viral promoters that can be used include, but are not limited to, adenovirus promoter, thymidine kinase (TK) promoter, and B19 Parvovirus promoter. Persons skilled in the art can readily select a suitable promoter based on the teaching of the present invention.

A nucleic acid sequence that encodes the polypeptide of the present invention is under the control of a suitable promoter. Examples of suitable promoters that can be used include, but are not limited to, adenovirus promoter such as adenovirus major late promoter, heterologous promoter such as CMV promoter, respiratory syncytial virus (RSV) promoter, inducible promoter such as MMT promoter or metallothionein promoter, heat shock promoter, albumin promoter, ApoAI promoter, human globin promoter, viral thymidine kinase promoter such as herpes simplex thymidine kinase promoter, retrovirus LTR including the aforementioned modified retrovirus LTR, β-actin promoter, and human growth hormone promoter. A promoter may be of a native type that controls the gene encoding polypeptides. A retrovirus plasmid vector is used to transduce the packaging cell line to form a producer cell line.

Examples of packaging cells to be transfected include, but are not limited to, PE501, PA317, Y-2, Y-AM, PA12, T19-14×, VT-19-17-H2, YCRE, YCRIP, GP+E-86, GP+en-vAm12, and the DAN cell line described in Miller, Human Gene Therapy 1: pp. 5-14 (1990).

A vector is transduced in a packaging cell by a means known in the art. Examples of such means include, but are not limited to, electroporation, the use of a liposome, and $CaPO_4$ precipitation. Alternatively, a retrovirus plasmid vector is sealed in a liposome or bound to a lipid to be administered to a host. A producer cell line produces infectious retrovirus vector particles comprising nucleic acid sequences encoding polypeptides. Such retrovirus vector particles are used to transduce eukaryotic cells in vitro or in vivo.

The transduced eukaryotic cells express nucleic acid sequences encoding polypeptides. Examples of eukaryotic cells that may be transduced include, but are not limited to, germinal stem cells, embryonal carcinoma cells, hematopoietic stem cells, hepatic cells, fibroblasts, sarcoblasts, keratinocytes, endothelial cells, and bronchial epithelial cells.

The protease of the present invention, an antibody against this protease, an antagonist of this protease, an inhibitor, an agonist, an activity modifier, or the like can be diluted with physiological saline, buffer, or the like to prepare a formulation. Thus, a pharmaceutical composition can be obtained. The pH value of the formulation is preferably between acidulous and neutral: close to the pH level of body fluid. The lower limit thereof is preferably between 5.0 and 6.4, and the upper limit is preferably between 6.4 and 7.4. Alternatively, the formulation can be provided in a state that allows storage for a long period of time, e.g., in a lyophilized state. In such a case, the formulation can be used by being dissolved in water, physiological saline, buffer, or the like at a desired concentration level at the time of use.

The formulation of the present invention may comprise a pharmacologically acceptable additive, such as a carrier, excipient, or diluent that is commonly used for pharmaceuticals, a stabilizer, or pharmaceutically necessary ingredients. Examples of a stabilizer include monosaccharides such as glucose, disaccharides such as saccharose and maltose, sugar alcohols such as mannitol and sorbitol, neutral salts such as sodium chloride, amino acids such as glycine, nonionic surfactants such as polyethylene glycol, polyoxyethylene and polyoxypropylene copolymers (Pluronic), polyoxyethylene sorbitan fatty acid ester (Tween), and human albumin. Addition thereof in amounts of about 1 to 10 w/v % is preferable.

An effective amount of the pharmaceutical composition of the present invention can be administered by, for example, intravenous injection, intramascular injection, or hypodermic injection in one or several separate dosages. The dosage varies depending on symptom, age, body weight, or other factors, and it is preferably 0.001 mg to 100 mg per dose.

Also, sense or antisense DNA encoding the protease of the present invention can be similarly prepared in a formulation to obtain a pharmaceutical composition.

Further, the present invention includes methods for inhibiting platelet plug formation involved with heart infarction or brain infarction, methods for inhibiting arteriosclerosis, methods for preventing restenosis, reembolization, or infarction involved with PTCA, methods for preventing reembolization involved with PTCR, and methods for preventing platelet plug formation caused by HUS or O-157 through the administration of the peptide, protein, and DNA of the present invention. Furthermore, the present invention includes the use of the peptide, protein, and DNA of the present invention in the production of pharmaceuticals for inhibiting platelet plug formation involved with heart infarction or brain infarction, pharmaceuticals for inhibiting arteriosclerosis, pharmaceuticals for preventing restenosis, reembolization, or infarction involved with PTCA, pharmaceuticals for preventing reembolization involved with PTCR, and pharmaceuticals for preventing platelet plug formation caused by HUS or O-157.

The peptide or protein of the present invention is used as a leading substance for amino acid modification. This enables the preparation of a molecule having activity that is different from that of the protease of the present invention. An example thereof is a variant molecule that can be obtained by preparing an antagonist, which is obtained by preparing a variant deactivated through amino acid substitution between an amino acid residue located around the active center in the metalloprotease domain and another amino acid, separating a molecule recognition site from a catalytic site, or varying one or both of these sites.

The use of an evaluation system for the vWF-cleaving activity described herein enables the production of an antagonist/agonist. For example, an effective antagonist can be a small organic molecule, a peptide, or a polypeptide. An example thereof is an antibody that is bound to the polypeptide of the present invention, thereby inhibiting or eliminating its activity.

Similarly, the use of the aforementioned evaluation system for vWF-cleaving activity enables the screening for a compound that is capable of cleaving vWF. In such a case, the cleaving activity of the test compound may be evaluated using the aforementioned evaluation system.

BRIEF DESCRIPTION OF THE DRAWINGS

FIG. 2 is a photograph showing the result of vWF multimer analysis (agarose electrophoresis).

FIG. 5 is a photograph showing the result of analyzing vWF-cleaving protease fractions after being subjected to gel filtration chromatography three times using the solubilized sample of F1 paste as a starting material.

FIG. 6 is a photograph showing the results of analyzing vWF-cleaving protease fractions in which the fraction collected by gel filtration chromatography is purified by DEAE anion exchange chromatography. In FIG. 6C, three bands indicate an intact vWF molecule (remaining uncleaved), a vWF cleavage fragment, and a vWF cleavage fragment, respectively, as in FIG. 5C.

FIG. 8 is a photograph showing the result of electrophoresis on a fraction obtained by further purifying a vWF-cleaving protease fraction by Biophoresis-based SDS-PAGE for analyzing vWF-cleaving protease activity and SDS-PAGE on active fractions under reducing conditions.

FIG. 9 relates to the identification of the vWF-cleaving protease gene (SEQ ID NO: 6), which is a diagram showing primers used for amplifying the gene fragment for a Northern blot probe. Amino acid sequence disclosed as SEQ ID NO: 7.

FIG. 10A shows the results obtained when the protease-encoding gene is used as a probe, and FIG. 10B shows the results obtained when a β-actin probe (RNA control) is used.

FIG. 11 relates to the identification of the vWF-cleaving protease gene (SEQ ID NO: 6), and is a diagram showing the locations and the sequences of the primers (SEQ ID NOS 9, 49, 14, 10, 51, 12, 53, and 13, respectively, in order of appearance) used in the RACE experiments.

FIG. 12 is a diagram showing the locations of primers designed for cloning full-length cDNA.

FIG. 13 is a diagram showing a process for constructing a vector containing full-length cDNA.

In FIG. 14, each lane shows the results using the indicated sample.
Lane 1: Mock (host: 293 cell)
Lane 2: vWF-cleaving protease, cDNA+FLAG (host: 293 cell)
Lane 3: Mock (host: HepG2 cell)
Lane 4: vWF-cleaving protease, cDNA+FLAG (host: HepG2 cell)
Lane 5: Mock (host: Hela cell)
Lane 6: vWF-cleaving protease, cDNA+FLAG (host: Hela cell)

In FIG. 15, each lane shows the results using the indicated sample.
Lane 1: Mock (host: Hela cell)
Lane 2: Supernatant in which vWF-cleaving protease was expressed (host: Hela cell)
Lane 3: Mock (host: HepG2 cell)
Lane 4: Supernatant in which vWF-cleaving protease was expressed (host: HepG2 cell)
Lane 5: Mock (host: 293 cell)
Lane 6: Supernatant in which vWF-cleaving protease was expressed (host: 293 cell)
Lane 7: Mock (host: BHK cell)
Lane 8: Supernatant in which vWF-cleaving protease was expressed (host: BHK cell)
Lane 9: Mock (host: COS cell)
Lane 10: Supernatant in which vWF-cleaving protease was expressed (host: COS cell)
Lane 11: Mock (host: CHO cell)
Lane 12: Supernatant in which vWF-cleaving protease was expressed (host: CHO cell)

In FIG. 16, each lane shows the results obtained with the use of the indicated sample.
Lane 1: Mouse antiserum (prepared by administering purified protein)
Lane 2: Rabbit antiserum (prepared by hypodermically administering an expression vector to a rabbit)
Lane 3: Untreated rabbit antiserum
Lane 4: Rabbit antiserum (prepared by administering KLH-conjugated partial synthetic peptide)

In FIG. 17, each lane shows the results obtained with the use of the indicated sample.
Lane 1: Partially purified sample derived from human plasma cryoprecipitate
Lane 2: Purified vWF-cleaving protease derived from human plasma
Lane 3: Gel-filtrated FI paste sample obtained from pooled human plasma
Lane 4: Recombinant vWF-cleaving protease (host: 293 cell)
Lane 5: Recombinant vWF-cleaving protease (host: Hela cell)

In FIG. 18, each lane shows the results obtained with the use of the indicated sample.
Lane 1: Gel-filtrated FI paste sample obtained from pooled human plasma
Lane 2: Normal human plasma 1
Lane 3: Normal human plasma 2
Lane 4: Normal human plasma 3
Lane 5: TTP patient's plasma 1
Lane 6: TTP patient's plasma 2
Lane 7: Recombinant vWF-cleaving protease (host: 293 cell)
Lane 8: Recombinant vWF-cleaving protease (host: Hela cell)

In FIG. 20, each lane shows the results obtained with the use of the indicated sample.

Lane 1: Applied culture supernatant (diluted 10-fold)
Lane 2: Passed-through fraction
Lane 3: Washed fraction
Lane 4: Elution fraction
In FIG. 21, each lane shows the results obtained with the use of the indicated sample.
Lane 1: vWF-cleaving protease solution: normal rabbit serum=1:1
Lane 2: vWF-cleaving protease solution: normal rabbit serum (diluted 5-fold)=1:1
Lane 3: vWF-cleaving protease solution: peptide-immunized rabbit serum=1:1
Lane 4: vWF-cleaving protease solution: peptide-immunized rabbit serum (diluted 5-fold)=1:1
Lane 5: vWF-cleaving protease solution: recombinant protein-immunized rabbit serum=1:1
Lane 6: vWF-cleaving protease solution: recombinant protein-immunized rabbit serum (diluted 5-fold)=1:1
Lane 7: vWF-cleaving protease solution: 10 mM EDTA=1:1
Lane 8: vWF-cleaving protease solution: buffer only=1:1
Lane 9: buffer (without vWF-cleaving protease): buffer=1:1

BEST MODES FOR CARRYING OUT THE INVENTION

The present invention is hereafter described in detail with reference to the following examples, although it is not limited to these examples.

EXAMPLE 1

(Preparation of vWF)

A plasma cryoprecipitation (2 g) was dissolved in 20 ml of buffer (0.01% Tween-80/50 mM Tris-HCl/100 mM NaCl, pH 7.4), and the resultant was subjected to gel filtration using a Sephacryl S-500 HR Column (2.6×90 cm, Amersham Pharmacia) to prepare vWF. Fractions were recovered at a flow rate of 2 ml/min in amounts of 6 ml each. vWF was analyzed by Western blotting using a peroxidase-labeled rabbit anti-human vWF antibody (DAKO), and high-molecular-weight vWF fractions were pooled. The pooled fractions were subjected to multimer analysis using agarose electrophoresis as described below.

Figure 1:
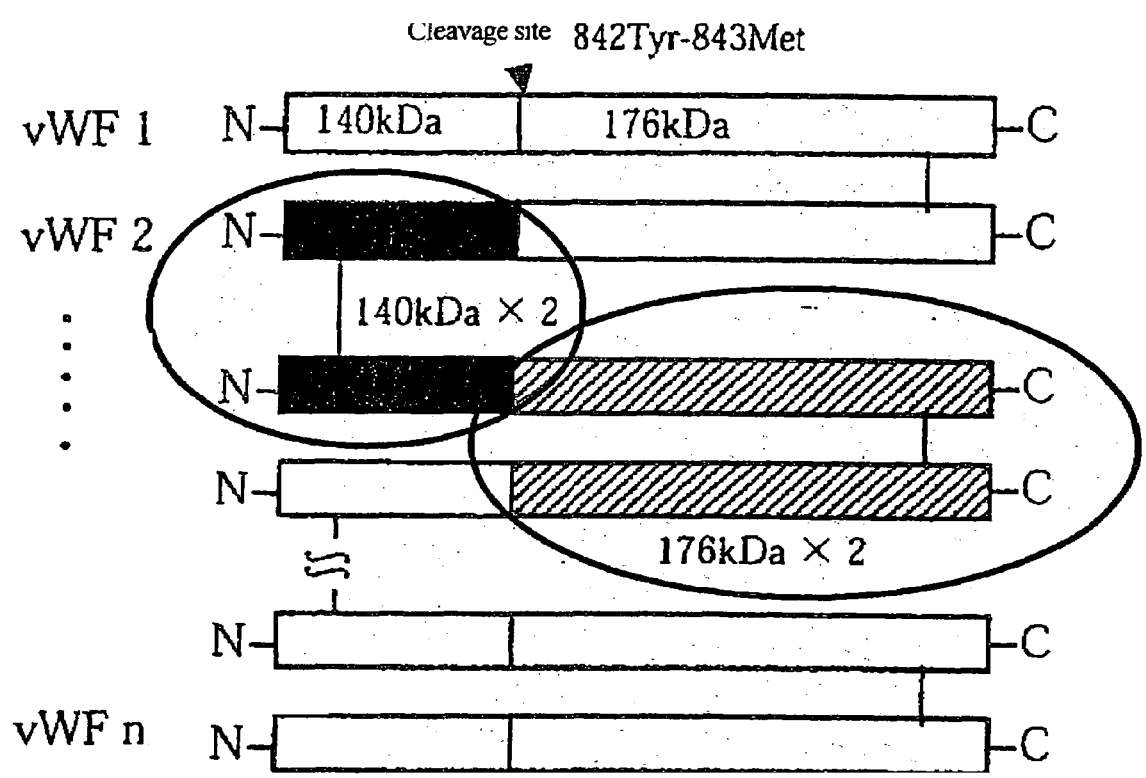
FIG. 1 is a diagram showing the vWF multimer structure and the point cleaved by the vWF-cleaving protease.

As shown in FIG. 1, vWF originally has a multimer structure in which vWF monomer molecules are polymerized with each other at their N-terminuses or at their C-terminuses, and vWF is subjected to partial hydrolysis by the vWF-specific cleaving protease. As a result of the analysis, as shown in FIG. 2, the purified vWF exhibited a multimer pattern based on agarose electrophoresis approximately equivalent to that in the plasma of a healthy person (the ladder in the drawing shows the electrophoresis pattern of vWF having a multimer structure, and the upper portion indicates vWF with advanced polymerization). This can prepare vWF comprising substantially no impurities that degrade it, and this fraction was used as a substrate when assaying the vWF-cleaving activity as described below.

EXAMPLE 2

(vWF-Cleaving Reaction)

vWF-cleaving activity was assayed as follows. A sample comprising 10 mM barium chloride (final concentration) was pre-incubated at 37° C. for 5 minutes to activate protease. A buffer (15 to 20 ml, 1.5 M urea/5 mM Tris-HCl, pH 8.0) was placed in a 50 ml Falcon Tube. Subsequently, a membrane filter (0.025 µm, Millipore) was floated therein, and 100 µl of activated sample prepared by mixing with 50 µl of vWF substrate solution was added. The resultant was allowed to stand in an incubator (37° C.) overnight and recovered from the filter on the next day. The recovered sample was evaluated based on the vWF cleavage pattern as described below in the "SDS-PAGE" section.

SDS-PAGE

SDS-5% polyacrylamide gel was autologously prepared and used. An SDS electrophoresis buffer (2 µl, in the presence or absence of a reducing agent, i.e., 2-mercaptoethanol) was added to 10 µl of the sample described in the "vWF-cleaving activity assay" section, and the resultant was boiled for 3 minutes to prepare an electrophoresis sample. The gel was subjected to electrophoresis at 30 mA for 1 hour and then stained with the Gel Code Blue Stain Reagent (PIERCE) utilizing CBB staining. As shown in FIG. 1, activity is evaluated based on the development of a cleavage fragment and the presence or absence of fragments remaining uncleaved under reducing or non-reducing conditions. This is more specifically described in Example 3 and FIG. 3 below.

Multimer Analysis Utilizing Agarose Electrophoresis

Preparation of Gel, Electrophoresis

Low gelling temperature agarose (Type VII, Sigma) was added to 375 mM Tris-HCl (pH 6.8) until a concentration of 1.4% was reached, followed by heating in a microwave oven to completely dissolve the gel. Thereafter, 0.1% SDS was added, and the resultant was maintained at 56° C. The resultant was made to flow into a gel mold and solidified by cooling at 4° C. overnight (running gel). The next day, high gelling temperate agarose (SeaKem) was mixed with 375 mM Tris-HCl (pH 6.8) until a concentration of 0.8% was reached, and dissolved by boiling in a microwave oven. Thereafter, the resultant was maintained at 56° C. (stacking gel). The gel prepared on the previous day was cleaved, leaving a 10-cm fraction from the end uncleaved. The aforementioned gel was made to flow into the cleaved portion, and the gel was made to keep flowing at 4° C. for at least 3 hours, followed by solidification. Pyronin Y was added to the sample described in the "vWF cleaving activity assay" section above, and the gel was prepared under non-reducing conditions without boiling. The gel was subjected to electrophoresis at 10 mA for at least 24 hours using an SDS-PAGE buffer.

Western Blotting

After the electrophoresis, the gel was immersed in a transcription buffer (0.005% SDS, 50 mM phosphate buffer, pH 7.4) for 10 minutes, and the resultant was transferred to a nitrocellulose membrane using a transcription apparatus at 4° C. at 0.5 A overnight. Blocking was performed using a blotting solution (5% skim milk, PBS) for 30 minutes, and the gel was then allowed to react for at least 6 hours with the peroxidase-labeled rabbit anti-human vWF antibody (DAKO), which was diluted 1,000-fold with the blotting solution. Thereafter, the gel was washed three times with the blotting solution and once with PBS, and color was developed using Konica Immunostain HRP-1000 (Konica), which was a substrate reaction solution for peroxidase. The purified vWF analyzed in this assay was found to have been undegraded, but was sufficiently usable as a substrate in the present invention (FIG. 2).

EXAMPLE 3

(Preparation of vWF-Cleaving Protease)

Figure 3:
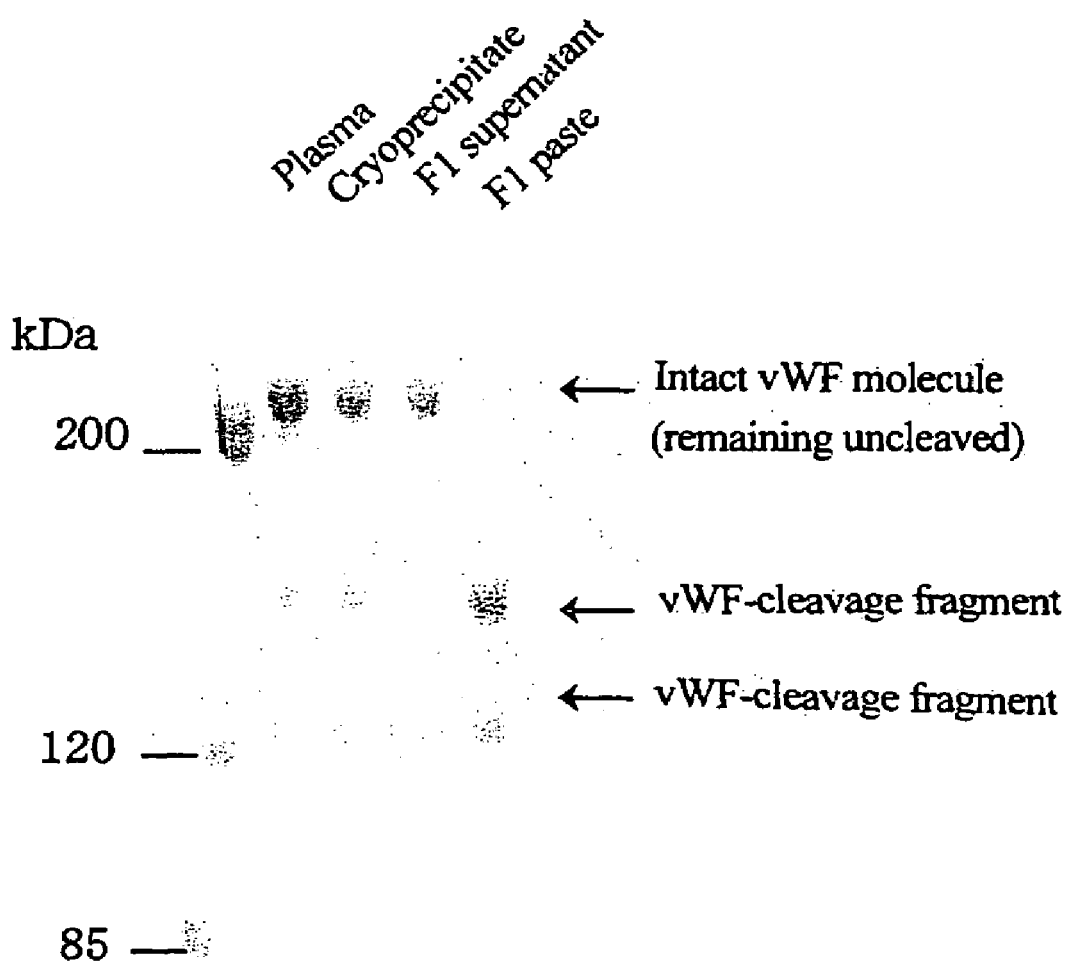
FIG. 3 is a photograph showing the result of SDS-PAGE (5% gel) for analyzing the vWF-cleaving activity of each plasma fraction under reducing conditions.

Plasma was subjected to ethanol fractionation developed by Cohn. A protease having high vWF-cleaving activity (one with high specific activity) when protein levels in four fractions (i.e., starting plasma, cryoprecipitate, fraction I (FI) supernatant, and a paste) are made equivalent to each other was selected. As shown in FIG. 3, the protease activity was highest in the FI paste. The N-terminal sequence of this cleavage fragment was analyzed, and as a result, activity derived from the cryoprecipitate and the FI paste were found to cleave the peptide bond between residues Tyr 842 and Met 843. Thus, the FI paste was determined to be a main starting material for purification thereafter.

Solubilization of FI Paste

Figure 4:
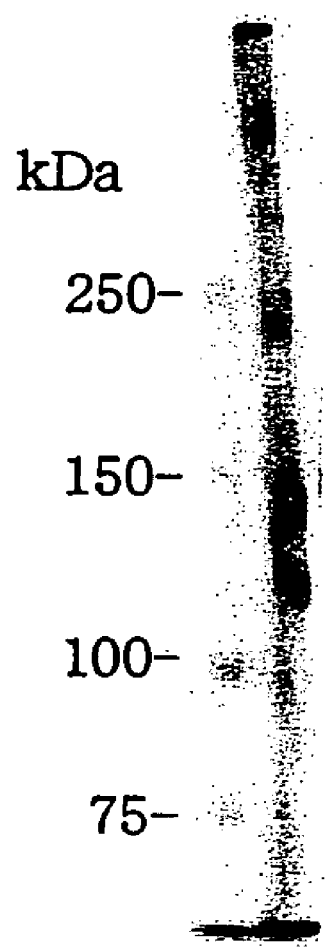
FIG. 4 is a photograph showing the result of SDS-PAGE (5% gel) for analyzing the solubilized sample of fraction 1 (F1) paste under non-reducing conditions.

The FI paste was fractionated in fractions of 12 g each and then cryopreserved. The paste was allowed to melt at 4° C. the day before its use. The next day, 120 ml of solubilizing buffer (0.05% azide, 50 mM Tris-HCl (pH 7.4), 100 mM NaCl) was added at 10 mg/ml, and the mixture was stirred at 37° C. for 2 hours. The product was centrifuged at 10,000 rpm for 10 minutes, and the supernatant was then recovered, followed by filtration with a prefilter, a 5.0 μm filter, and a 0.8 μm filter in that order. The resultant was determined to be a solubilized sample. FIG. 4 shows the result of SDS-PAGE of the solubilized sample.

Gel Filtration Chromatography of vWF-Cleaving Protease

The solubilized F1 paste was applied to a Sephacryl S-300 HR Column (5×90 cm, Amersham Pharmacia) to conduct the first gel filtration. A buffer comprising 0.05% azide, 50 mM Tris-HCl (pH 7.4), and 100 mM NaCl (hereinafter referred to as an "elution buffer"), which was the same as the solubilizing buffer, was used. The flow rate was 5 ml/min, fractionation was initiated at 600 ml after the sample application, and fractions were recovered in amounts of 10 ml each. Fractions were subjected to the vWF-cleaving reaction, and their activities were then analyzed by SDS-PAGE. Fractions that exhibited protease activity were pooled, and a small amount of saturated ammonium sulfate was gradually added dropwide thereto until a final concentration of 33% saturation was reached. The mixture was further allowed to stand at 4° C. overnight. The next day, the product was centrifuged at 10,000 rpm for 10 minutes, and an active fraction of interest was recovered as a precipitate. The procedures comprising solubilization, gel filtration, and ammonium sulfate precipitation were performed for 5 batches and the resultant was cryopreserved at −20° C.

The ammonium sulfate precipitates (2 to 3 batches) obtained by the first gel filtration were dissolved in 50 ml of elution buffer, and passed through the Sephacryl S-300 HR Column (5×90 cm) in the same manner as in the first gel filtration to perform the second gel filtration. The elution buffer, conditions, operations, and the like were the same as those in the first gel filtration. Fractions were subjected to the vWF-cleaving reaction, and their activities were then analyzed by SDS-PAGE. Fractions with activity were pooled, and ammonium sulfate precipitation was similarly performed. These procedures were repeated two times.

Figure 5A:
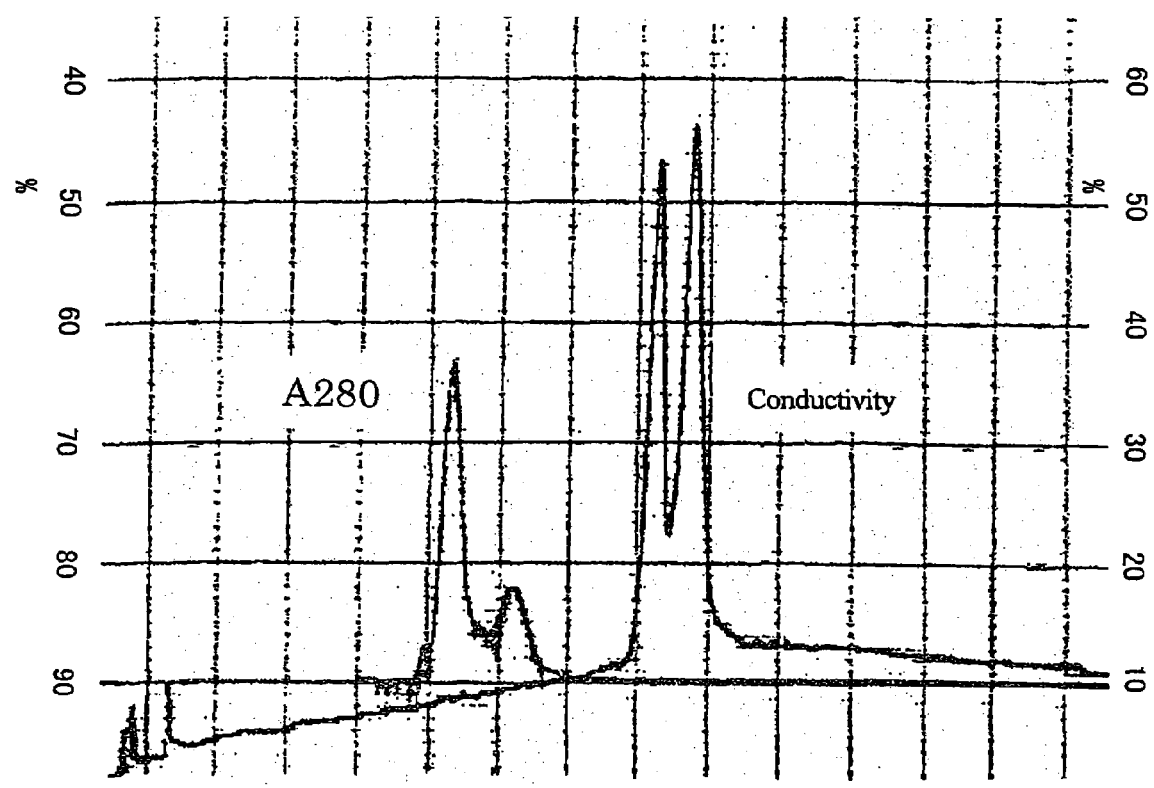
FIG. 5A is a chart showing gel filtration chromatography.
Figure 5B:
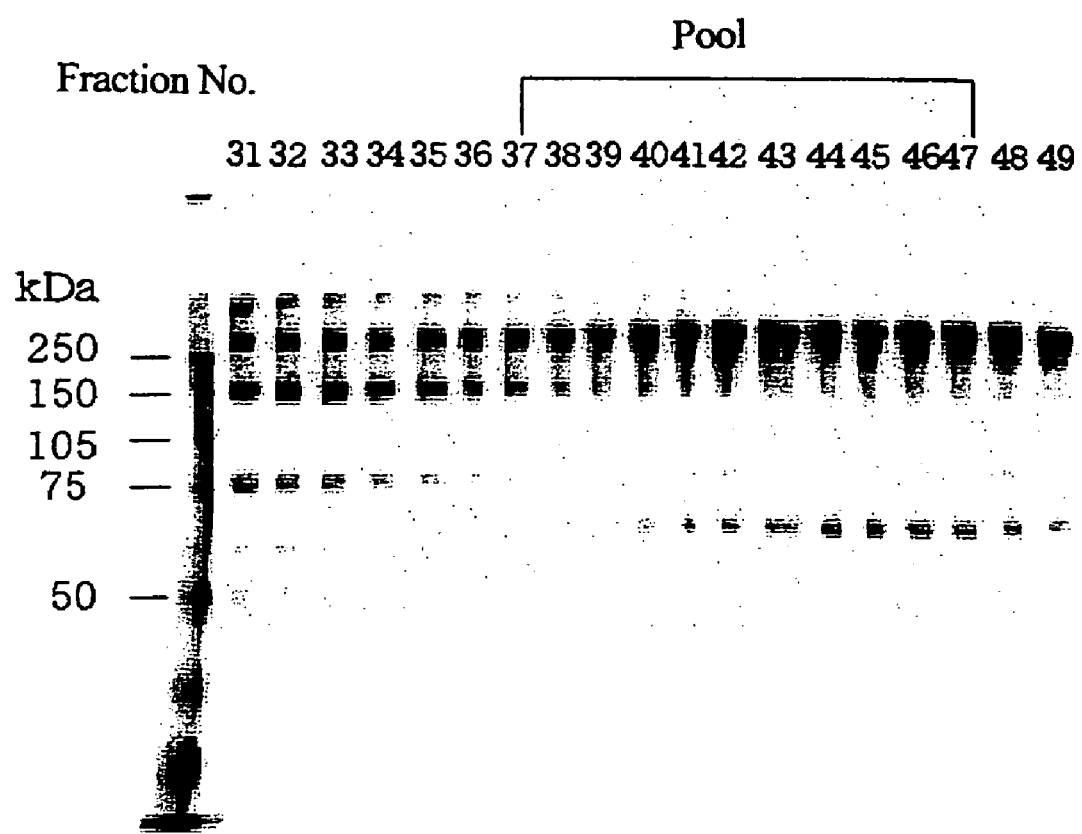
FIG. 5B shows the result of SDS-PAGE on fractions under non-reducing conditions.
Figure 5C:
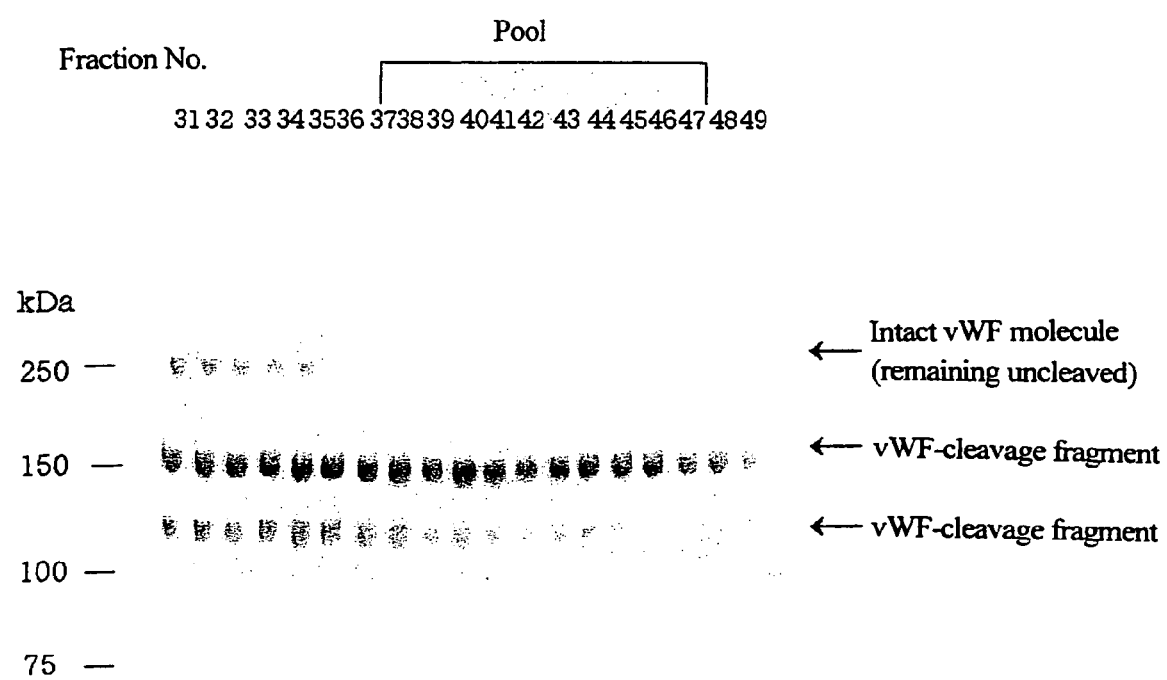
FIG. 5C shows the results of SDS-PAGE on vWF-cleaving activity under reducing conditions.

The ammonium sulfate precipitates (2 batches) obtained by the second gel filtration were dissolved in 50 ml of elution buffer, and applied to the Sephacryl S-300 HR Column (5×90 cm) in the same manner as in the first and the second gel filtration to perform the third gel filtration. The elution buffer, conditions, operations, and the like were the same as those in the first and the second gel filtration. Fractions were subjected to the vWF-cleaving reaction, and their activities were then analyzed by SDS-PAGE, followed by pooling. FIG. 5 shows SDS-PAGE for analyzing these fractions and that for analyzing vWF-cleaving activity. Based on the patterns of gel filtration and the data showing activity, the protease of the present invention was found to be eluted in the region between fraction 37 and fraction 47. Based on a separately conducted elution experiment for high-molecular-weight gel filtration marker (Amersham Pharmacia), this site of elution was deduced to have a molecular weight equivalent to 150 to 300 kDa. In this phase, considerable amounts of impurities were still present.

DEAE Anion Exchange Chromatography

Figure 6A:
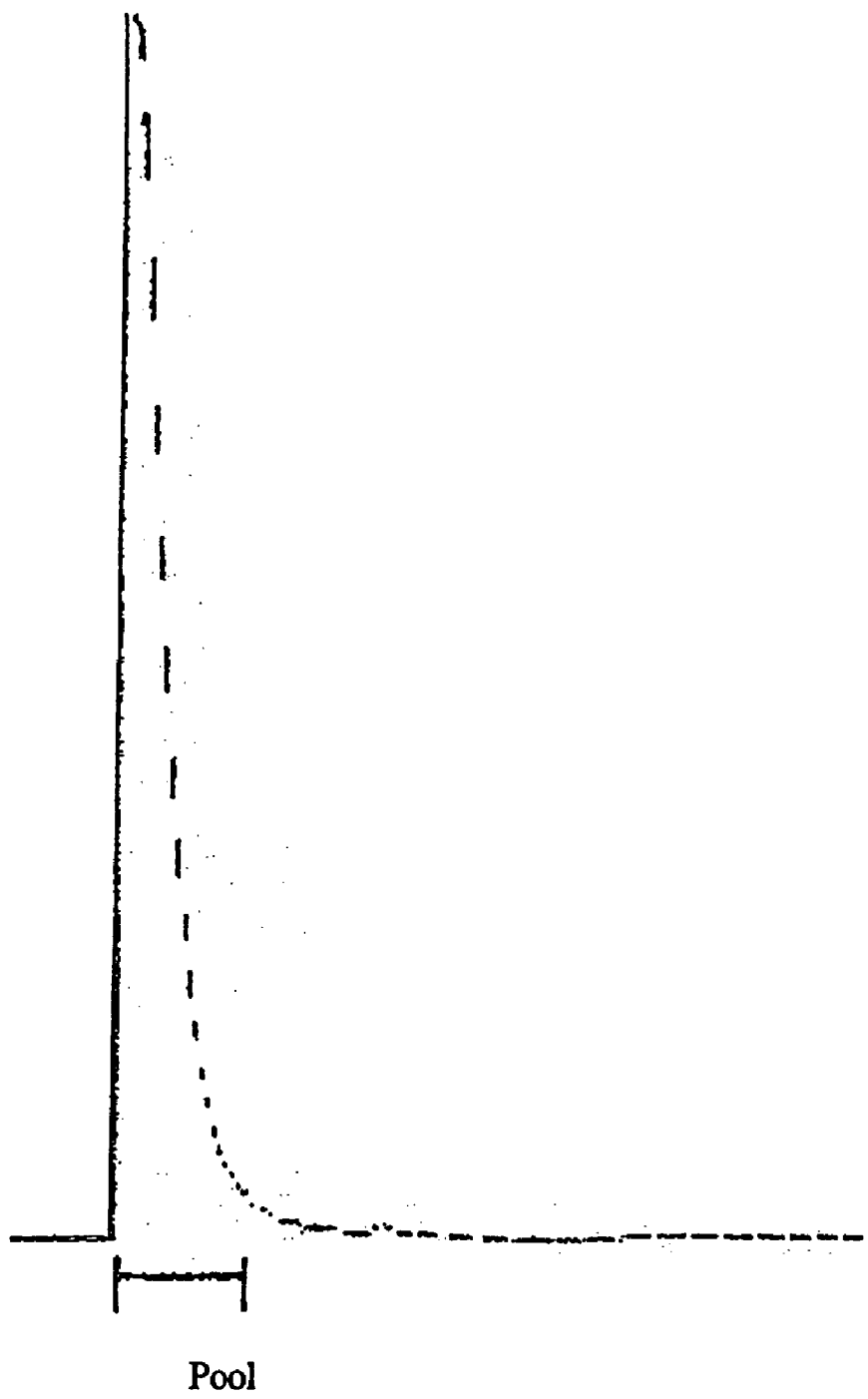
FIG. 6A is a chart showing gel filtration chromatography.
Figure 6B:
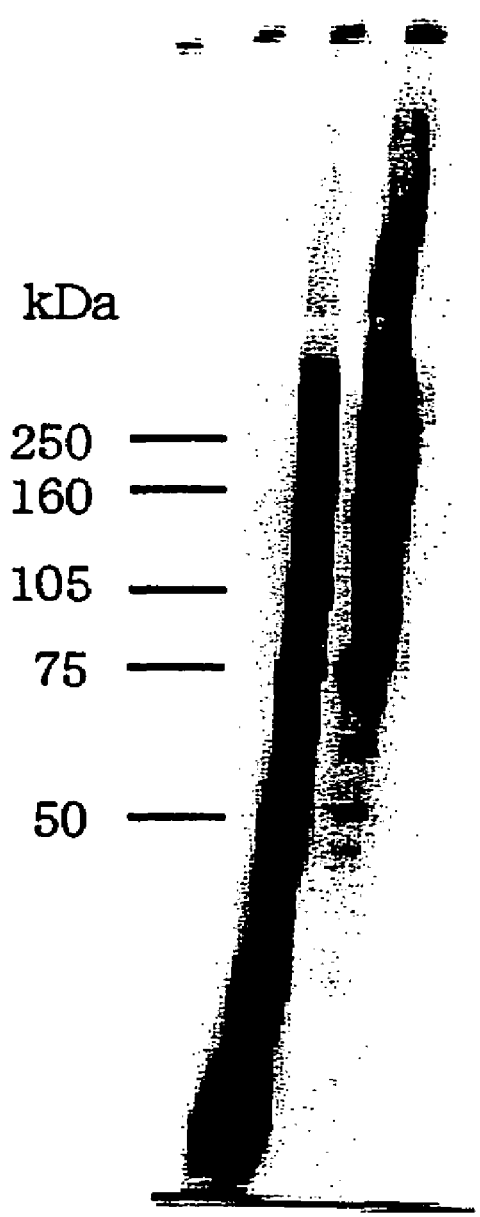
FIG. 6B shows the result of SDS-PAGE (8% gel) on elution fractions under non-reducing conditions.
Figure 6C:
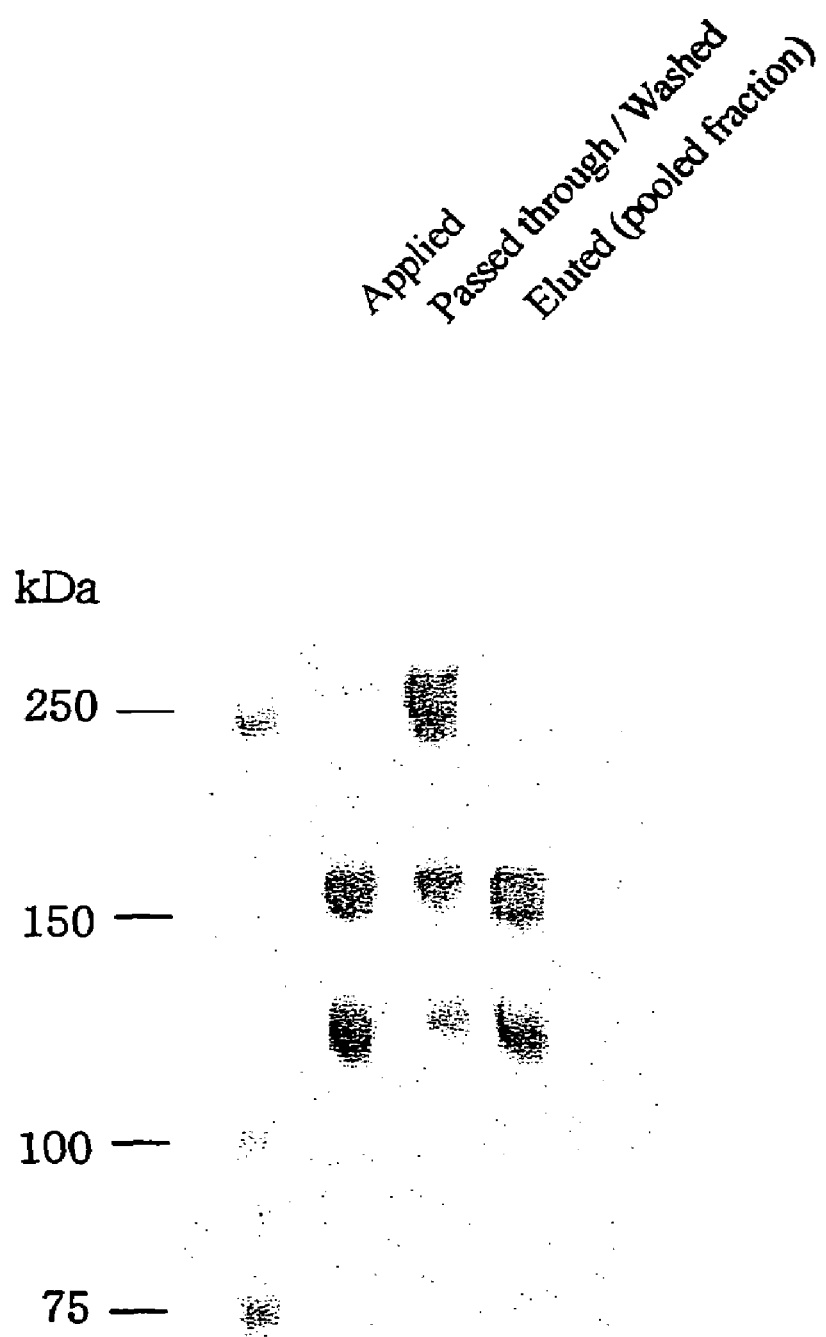
FIG. 6C shows the results of SDS-PAGE on vWF-cleaving activity under reducing conditions.

The pooled fraction obtained by three gel filtration operations was subjected to dialysis overnight with a buffer comprising 50 mM Tris-HCl and 50 mM NaCl (pH 7.1). After the dialysis, anion exchange chromatography was performed using a 5 ml HiTrap DEAE-Sepharose Fast Flow Column (Pharmacia) to conduct further purification and concentration. Equilibrating and washing were performed using a buffer comprising 50 mM Tris-HCl (pH 7.1), and elution was performed using 0.25 M NaCl. The flow rate was 5 ml/min, and 5 fractions of 5 ml each were recovered and pooled. FIG. 6 shows the results of SDS-PAGE for analyzing elution fractions and those for analyzing vWF-cleaving activity. Based on SDS-PAGE for activity assay, the protease of the present invention having vWF-cleaving activity was considerably effectively concentrated in the elution fraction.

Fractionation Utilizing SDS-PAGE

Figure 7:
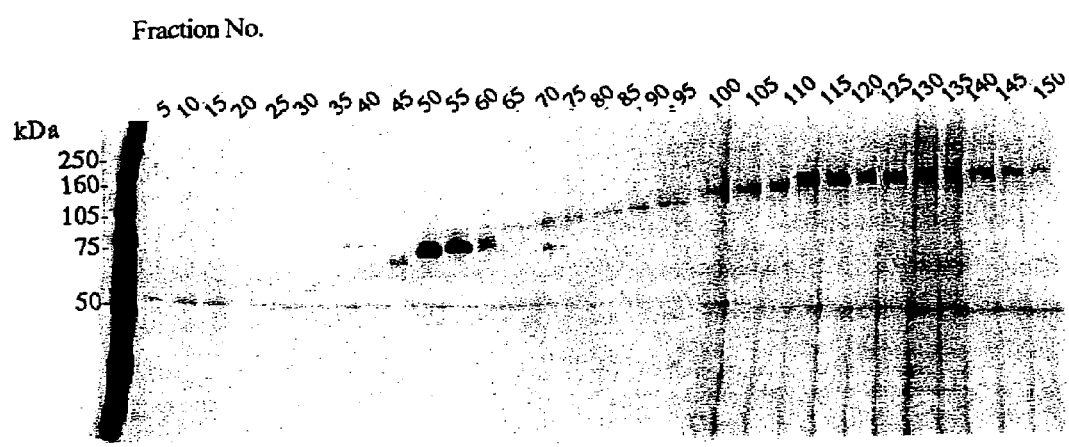
FIG. 7 is a photograph showing an electrophoresed fragment obtained when the vWF-cleaving protease fraction purified and concentrated by DEAE anion exchange chromatography is further purified by Biophoresis-based SDS-PAGE (non-reducing conditions).
Figure 8A:
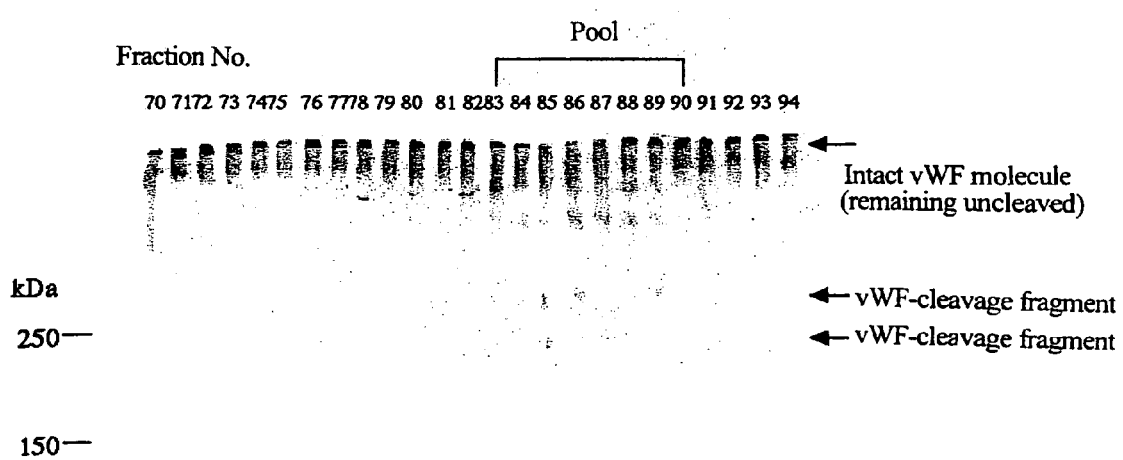
FIG. 8A shows the results of SDS-PAGE for analyzing vWF-cleaving protease activity under non-reducing conditions.
Figure 8B:
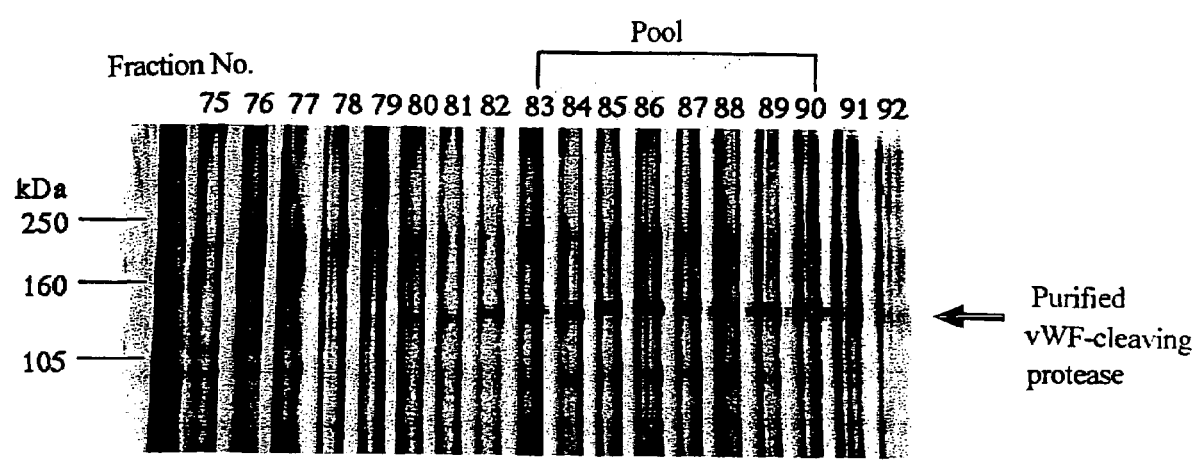
FIG. 8B shows the results of SDS-PAGE for analyzing active fractions under reducing conditions.

The sample (5 ml) purified and concentrated by DEAE anion exchange chromatography was further concentrated to 0.5 ml using Centricon (molecular weight cut off: 10,000 Da, Amicon). The protease of the present invention was isolated by Biophoresis III (Atto Corporation) utilizing SDS-PAGE. In accordance with the Laemmli method (Nature, vol. 227, 680-685, 1970), a buffer for electrophoresis tanks was prepared, and developed with 8% polyacrylamide gel to recover the electrophoresis fraction. FIG. 7 shows the result of SDS-PAGE for analyzing the recovered fractions. The buffer used for recovery was comprised of 50 mM Tris-HCl and 10% glycerol (pH 8.8). As is apparent from FIG. 7, this process according to the present invention has a high ability to produce separation. FIG. 8 shows the results of analyzing activity of a fraction further purified by electrophoresis and the results of SDS-PAGE for analyzing active fractions. The protease of the present invention can be recovered as an active molecule even after SDS-PAGE. When the activity of this protease in the plasma is determined to be 1 in terms of specific activity, a degree of purification of 30,000- to 100,000-fold was deduced to be achieved based on the average protein content in the plasma (60 mg/ml).

EXAMPLE 4

(Partial Amino Acid Sequencing)

The partial amino acid sequence of the isolated protease was determined. This protease, which was isolated using Biophoresis, was transferred to a PVDF membrane after SDS-PAGE by a conventional technique, air-dried, and then subjected to analysis using the automated protein sequencer (model 492; PE Applied Biosystems). As a result, the vWF-cleaving protease of the present invention isolated under the above conditions was found to comprise a polypeptide chain having a molecular weight of 105 to 160 kDa in SDS-PAGE under reducing conditions. This protease was also found to have, as a partial sequence, Leu-Leu-Val-Ala-Val (SEQ ID NO: 1), and preferably Ala-Ala-Gly-Gly-Ile-Leu-His-Leu-Glu-Leu-Leu-Val-Ala-Val (SEQ ID NO: 2).

Deduction of Isolated Protease Utilizing Bioinformatics

At present, bioinformatics enables the deduction of full nucleotide sequences encoding a polypeptide without substantial gene cloning through collation with information in the database accumulated in the past (BIOINFORMATICS: A Practical Guide to the Analysis of Genes and Proteins, edited by Andreas D. Baxevanis and B. F. Francis Ouellette). Based on the partial amino acid sequencing by the aforementioned process (Ala-Ala-Gly-Gly-Ile-Leu-His-Leu-Glu-Leu-Leu-Val-Ala-Val (SEQ ID NO: 2)), the database was searched by the tblastn program. As a result, a chromosome clone (AL158826) that was deduced to encode the protease of the present invention was identified by genomic database search. Further, a part of the protease of interest as the expressed sequence tag (EST) and a clone that was deduced to be a part of the polypeptide encoded by the aforementioned genome (AI346761 and AJ011374) were identified. The amino acid sequence as shown in SEQ ID NO: 3 or 7 was deduced based thereon to be an active vWF-cleaving protease site.

EXAMPLE 5

(Gene Identification)

Synthesis of all the following synthetic primers was performed by Greiner Japan Co. Ltd. by request. Further, reagents used for gene recombination were those manufactured by TAKARA, TOYOBO, and New England Biolabs unless otherwise specified.

Preparation of a Gene Fragment as a Northern Blotting Probe

A sense primer (SEQ ID NO: 9) and an antisense primer (SEQ ID NO: 10) were prepared. PCR was carried out using Universal QUICK-Clone™ cDNA (Clontech), which was a mixture of cDNA derived from normal human tissue, as a template and TaKaRa LA Taq with GC rich buffer. A gene sandwiched between these primers was amplified, and the amplified fragment was cloned using a TOPO TA cloning™ kit (Invitrogen). DNAs having the nucleotide sequence as shown in SEQ ID NO: 6 were isolated from several clones.

A vector portion was removed from this cloned DNA by EcoRI digestion, separated and purified by agarose electrophoresis, and the resultant was determined to be a template for preparing probes for Northern blotting.

Northern Blotting

Figure 10:
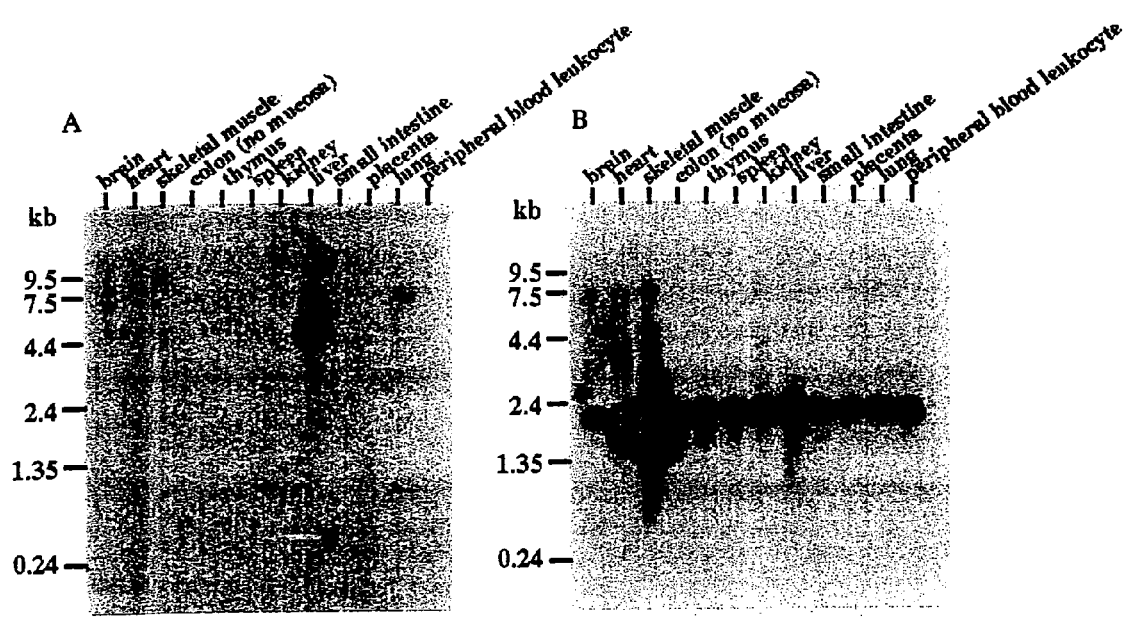
FIG. 10 relates to the identification of the vWF-cleaving protease gene, which is a photograph showing Northern blot autoradiography.

The gene fragment prepared above was employed as a template to prepare a radioactive probe using [$\alpha$-$^{32}$P]dCTP (Amersham Pharmacia) and a BcaBEST™ labeling kit (TAKARA). Hybridization was carried out using the Human 12-lane Multiple Tissue Northern Blots™ (Clontech) filter in accordance with the method described in Molecular Cloning 2$^{nd}$ Edition, pp. 9.52-9.55. Detection was carried out by autoradiography. As shown in FIG. 10, mRNA encoding the protease was expressed mainly in the liver. The size of this mRNA was found to be more than 4.4 kb.

Isolation and Identification of Gene Encoding the Protease

As a result of Northern blotting, mRNA was found to be expressed mainly in the liver. Thus, the protease gene of the present invention was isolated and identified in accordance with the RACE technique using normal human liver-derived poly A$^+$ RNA and MARATHON-READY™ cDNA (Clontech), which is a premade full length cDNA library of adaptor-ligated ds cDNA ready for use.

More specifically, the first PCR was carried out as 5' RACE using normal human liver-derived MARATHON-READY™ cDNA, which is a premade full length cDNA library of adaptor-ligated ds cDNA ready for use, in accordance with the product's manual and using the AP-1 primer attached to the kit and antisense primers (SEQ ID NOs: 11 to 13) arbitrarily selected from the group of Gene Specific Primers (GSP) excluding the primer 1 located in the uppermost stream as shown in FIG. 11. Nested PCR (the second PCR) was then carried out using the AP-2 primer located in the inside thereof and the antisense primer located in the inside of the primer used for the first PCR as shown in FIG. 11. Thereafter, TA cloning was carried out. Genes were prepared from the developed colonies in accordance with a conventional technique (Molecular Cloning 2$^{nd}$ Edition, pp. 1.25-1.28), and nucleic acid sequences were decoded using an automatic DNA sequencer. The primer used for sequencing was the primer used for PCR or a primer located in the inside thereof. Further, the primer was designed based on the sequence determined after serial decoding.

3' RACE was started from normal human liver-derived poly A$^+$ RNA using the 3'-Full RACE Core Set (TAKARA), and reverse transcription was carried out in accordance with the attached manual using the attached oligo dT primer. The band amplified by PCR using the sense primer (SEQ ID NO: 14) located at "primer 2" in FIG. 11 and the attached oligo dT primer was separated by agarose electrophoresis and extracted, followed by TA cloning. Genes were prepared from the developed colonies, and nucleic acid sequences were decoded using an automatic DNA sequencer. A primer used for sequencing was designed based on the sequence determined after serial decoding.

EXAMPLE 6

(Preparation of a Vector Comprising Full-Length cDNA 1)

cDNA encoding the protein was subjected to one-stage PCR by, for example, using a sense primer 1 (SEQ ID NO: 22) comprising an XhoI restriction site and an initiation codon and an antisense primer 2 (SEQ ID NO: 23) comprising an SalI restriction site and a termination codon (see FIG. 12), using the aforementioned normal human liver-derived MARATHON-READY™ cDNA, which is a premade full length cDNA library of adaptor-ligated ds cDNA ready for use, as a template and the TaKaRa LA Taq with GC rich buffer, followed by the aforementioned TA cloning. Thereafter, the full length of the product was confirmed using an automatic DNA sequencer.

EXAMPLE 7

(Preparation of a Vector Comprising Full-Length cDNA 2)

Restriction sites AccI and AvrII that cleaved cDNA only at one point on the inner sequence of the cDNA (SEQ ID NO: 15) encoding the protein were found. With the use thereof, full-length cDNA was divided into three fragments as shown in FIG. 12. A fragment 1 sandwiched between the sense primer 1 (SEQ ID NO: 22) and the antisense primer 3 (SEQ ID NO: 24), a fragment 2 sandwiched between the sense primer 4 (SEQ ID NO: 25) and the antisense primer 5 (SEQ ID NO: 26), and a fragment 3 sandwiched between the sense primer 6 (SEQ ID NO: 27) and the antisense primer 2 (SEQ ID NO: 23) were provided, respectively, in each of the above three fragments. Each fragment was subjected to PCR using the aforementioned normal human liver-derived Marathon-Ready™ cDNA as a template and TaKaRa LA Taq with GC rich buffer, followed by the aforementioned TA cloning. The full length of the product was confirmed using an automatic DNA sequencer. Further, the pCR 2.1 vector included in the aforementioned TA cloning kit was subjected to self ligation, the ligation product was cleaved with XhoI/HindIII, ligated to a linker comprising XhoI/AccI/AvrII/HindIII (prepared by annealing the synthetic DNA as shown in SEQ ID NO: 28 or 29), and the three aforementioned fragments were sequentially ligated in a conventional manner to bind them. Thus, cDNA comprising the entire region was prepared (see FIG. 13).

EXAMPLE 8

(Preparation of an Expression Vector Comprising Full-Length cDNA: an Animal Cell Host)

DNA obtained in Example 6 or 7 was digested with restriction enzymes XhoI/SalI, ligated to, for example the SalI site in the pCAG vector (Niwa, H. et al., Gene, vol. 108, 193-199), and the direction of the insertion and the full-length sequence were confirmed using an automatic DNA sequencer.

EXAMPLE 9

(Transfection of an Expression Vector Comprising Full-Length cDNA into an Animal Cell)

Figure 14:
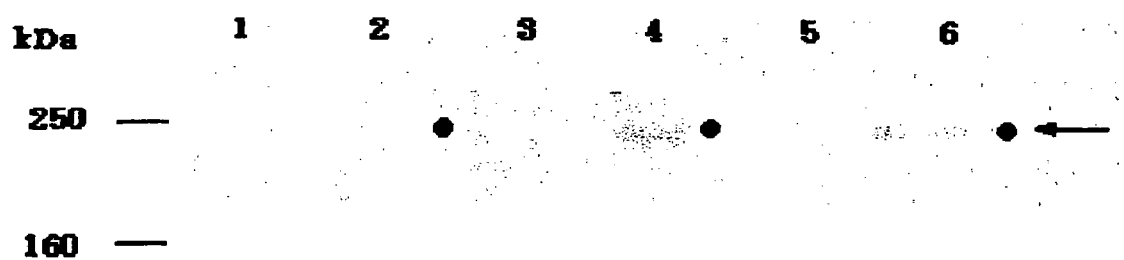
FIG. 14 is a photograph showing the expression in various cell lines (Western blotting under reducing conditions using anti-FLAG antibody, where the mock is prepared by inversely inserting a gene in an expression vector).
Figure 17:
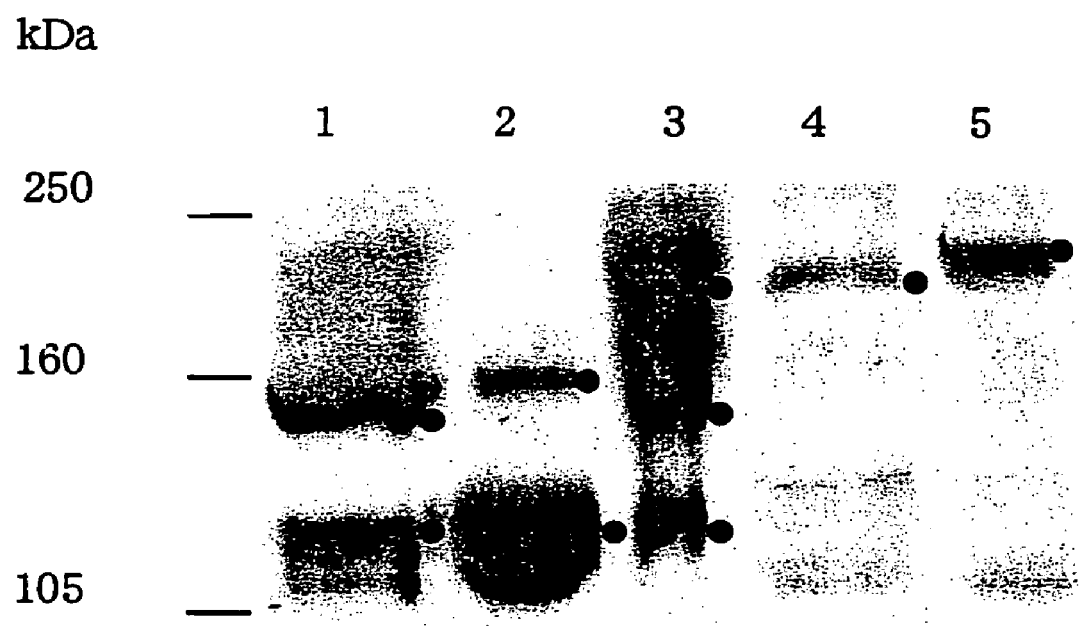
FIG. 17 is a photograph showing the result of Western blotting using an antibody established against the protease of the present invention, wherein various samples derived from human plasma and recombinant expression units are detected using rabbit antiserum obtained by administering full-length cDNA of vWF-cleaving protease.
Figure 18:
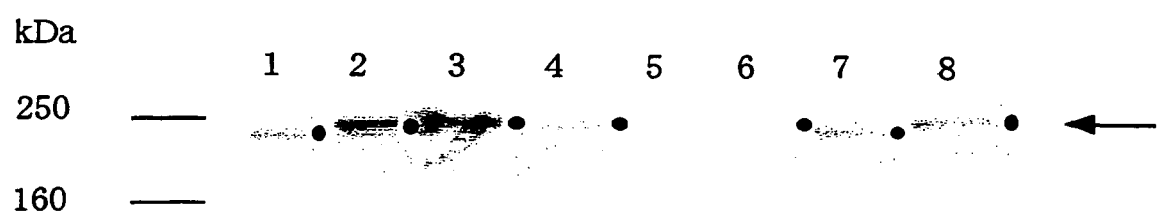
FIG. 18 is a photograph showing the result of Western blotting using an antibody established against the protease of the present invention, wherein rabbit antiserum obtained by immunizing a rabbit with a partially synthesized peptide of the vWF-cleaving protease is used to confirm the vWF-cleaving protease in healthy human plasma and that in the plasma and gene recombinant vWF-cleaving protease of a TTP patient.

The animal cell expression vector prepared in Example 8 was transfected in the following manner using the 293 cell (human embryonic kidney cell line), the Hela cell, and the HepG2 cell. At the outset, cells were disseminated at 1 to $3 \times 10^5$ cells per 35 mm dish 24 hours before the transfection. The next day, 2 µl of polyamine transfection reagent, TransIT (TAKARA), per µg of the expression vector, were added to 100 µl of a serum-free medium such as Opti-MEM to prepare a complex with DNA in accordance with the instructions included with the reagent. Thereafter, the complex was added dropwise to the various types of previously prepared cells, and the resultants were incubated for 2 to 8 hours, followed by medium exchange. The medium was further exchanged three days later with the selective medium to which G418 had been added. Thereafter, medium was exchanged every three days to produce a stably expressed strain. An example thereof is shown in FIG. 14 as a temporarily expressed strain comprising an FLAG epitope tag at its C-terminus. Detection was carried out by Western blotting using the anti-FLAG-M2 antibody (Kodack) and staining with anti-mouse Ig-alkaline phosphatase-labeled antibody system. The recombinant strain expressed using cDNA as shown in this example exhibited a molecular size of about 250 kDa under reducing conditions. This molecular size was also found in the plasma of a healthy human (FIG. 18, Example 14 below). Several different molecular species of this protease are found to be present in the human plasma, which could be caused by the presence of the alternative splicing products (SEQ ID NOs: 6 to 21) observed at the time of gene cloning, difference in post-translational modification such as sugar chain addition, or degradation during purification (described in Example 14 and in FIG. 17 of the present invention and Gerritsen et al., Blood, vol. 98, 1654-1661 (2001)).

Figure 15:
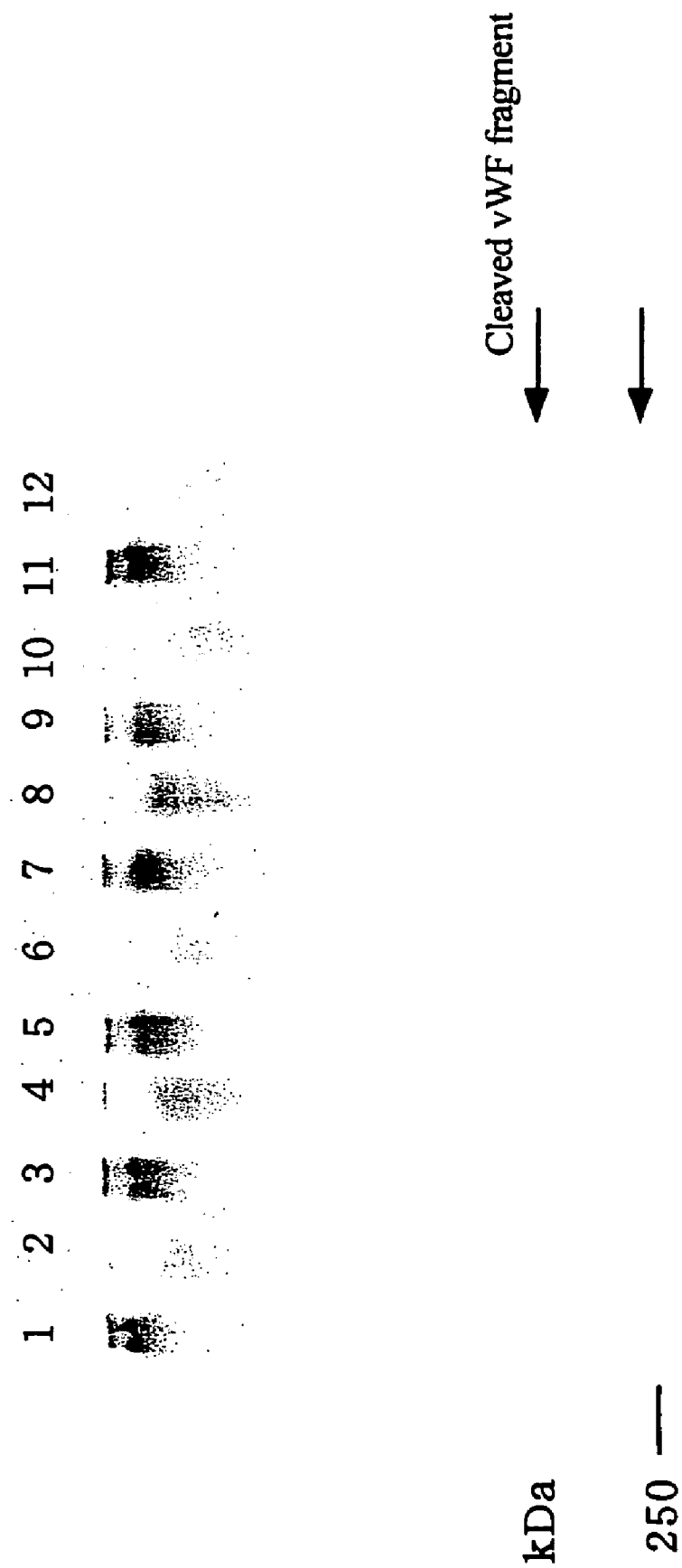
FIG. 15 is a photograph showing the activity assay of recombinant expression protease (analysis of vWF-cleavage by SDS-PAGE under non-reducing conditions, where the mock is prepared by inversely inserting a gene in an expression vector).

Subsequently, the vWF-cleaving activity of the recombinant strain was confirmed by the method described in Example 2 (FIG. 15). As a result, the human plasma-derived protease and the gene recombinant product of the present invention were found to exhibit the same vWF-cleaving activities.

EXAMPLE 10

(Preparation of an Expression Vector Comprising Partial cDNA: an *E. coli* Host)

Partial cDNA encoding the metalloprotease domain of the protein was subjected to PCR using a sense primer comprising an NcoI restriction site and an initiation codon (SEQ ID NO: 30) and an antisense primer comprising an HindIII restriction site and a termination codon (SEQ ID NO: 31), the aforementioned normal human liver-derived MARATHON-READY™ cDNA, which is a premade full length cDNA library of adaptor-ligated ds cDNA ready for use, or the cDNA obtained in Example 6 or 7 as a template, and the TaKaRa LA Taq with GC rich buffer. The PCR product was then digested with NcoI/HindIII, ligated to the NcoI/HindIII digest of an *E. coli* expression vector such as pUT1 (Soejima et al., J. Biochem. Tokyo, vol. 130,269-277 (2001)), and transformed to the *E. coli* competent cell JM 109 by a conventional technique. Several clones were collected from the formed colony group, and genes were prepared therefrom. Thereafter, the resulting genes were confirmed to be the genes encoding the polypeptide, wherein the nucleic acid sequence of the insertion site of the plasmid vector was equivalent to SEQ ID NO: 32 or substantially represented by SEQ ID NO: 33, using an automatic DNA sequencer.

EXAMPLE 11

(Expression of Partial cDNA-Containing Expression Vector in *E. coli*)

An *E. coli* host with the expression vector constructed in Example 10 introduced therein was precultured in 200 ml of LB medium comprising 50 µg/ml ampicillin at 30° C. overnight. The resultant was sowed in a fermenter comprising 8 liters of LB medium, and culture was conducted at 30° C. until the turbidity at 600 nm became 0.2 to 0.5. Thereafter, isopropyl-1-thio-β-D-galactopyranoside was added to a final concentration of 1 mM, and the mixture was further cultured overnight to induce the metalloprotease domain of the protein to be expressed. The cultured *E. coli* were collected using a centrifuge (4° C. for 30 minutes).

Subsequently, the collected *E. coli* pellet was resuspended in distilled water, and lysozyme (final concentration: 0.6 mg/ml) was added thereto. The mixture was stirred at room temperature for 30 minutes, allowed to stand at 4° C. overnight, and cells were then destroyed. After the ultrasonication, centrifugation was carried out using a centrifuge (4° C. for 20 minutes), and the pellet was recovered. The recovered pellet was resuspended in a buffer comprising 50 mM Tris, 10 mM EDTA, and 1% Triton X-100 (pH 8.0). These procedures of centrifugation, ultrasonication, and resuspension were repeated several times, and the pellet was then resuspended in distilled water. Similarly, procedures of centrifugation, ultrasonication, and resuspension were repeated several times to recover an inclusion body. This inclusion body was used as an antigen when producing an antibody.

EXAMPLE 12

(Isolation of Homologous Gene of Other Animal Species)

The nucleic acid sequence as shown in SEQ ID NO: 15 was used as a probe, and a homology search was conducted using the BLASTN program at the GenomeNet WWW server (http://www.genome.adjp/). As a result, chromosome clones AC091762 and AC090008 that were mapped at mouse chromosome 10 were obtained. Based on these sequences, a mouse homolog of the protease of the present invention as shown in SEQ ID NO: 34 was deduced. A new primer was designed from this sequence, and Northern blot analysis was conducted by the technique used in isolating and identifying the gene encoding the human vWF-cleaving protease. Thus, the occurrence of the specific expression in the liver was observed as with the case of humans. Further, normal mouse liver-derived poly A+ RNA and MARATHON-READY™ cDNA (Clontech), which is a premade full length cDNA library of adaptor-ligated ds cDNA ready for use, were used to isolate and identify the protease gene of the present invention by the RACE technique as in the case of humans. As a result, the mouse homologous gene sequences of the protease as shown in SEQ ID NOs: 35 and 36 were determined.

Based on the thus determined mouse homologous partial sequence, the Exon/Intron structure on the 5' side of the aforementioned mouse chromosome 10 was determined. In accordance with a conventional technique (e.g., Gene Targeting: A Practial Approach First Edition, edited by A. L. Joyner, Teratocarcinomas and embryonic stem cell a practical approach), a targeting vector for knock-out (knock-in) mice can be prepared based thereon. This enabled the production of mutated mice. Further, this protein can be subjected to recombinant expression by a conventional technique.

EXAMPLE 13

(Production of an Antibody and Construction of a Detection System for the Present Protease Using the Antibody)

In accordance with a conventional technique (e.g., Current Protocols in Molecular Biology: Chapter 11 immunology, Antibody Engineering: A PRACTICAL APPROACH, edited by J. McCAFFERTY et al. or ANTIBODY ENGINEERING second edition, edited by Carl A. K. BORREBAECK), an expression vector was administered to a mouse or rat. This expression vector comprises a substance prepared by optionally binding an antigen protein partially purified from human plasma or a synthetic peptide having a partial amino acid sequence thereof (e.g., a C-terminal peptide sequence Phe-Ser-Pro-Ala-Pro-Gln-Pro-Arg-Arg-Leu-Leu-Pro-Gly-Pro-Gln-Glu-Asn-Ser-Val-Gln-Ser-Ser (SEQ ID NO: 37), which was one isoform of the protease of the present invention) to an optimal carrier substance such as KLH (Cys was added to, for example, the N- or C-terminus to facilitate KLH addition), the aforementioned gene recombinant protein, or a gene encoding this protein. Thus, a monoclonal antibody-expressing hybridoma was established, and a polyclonal antibody (antiserum) was produced.

Figure 16:
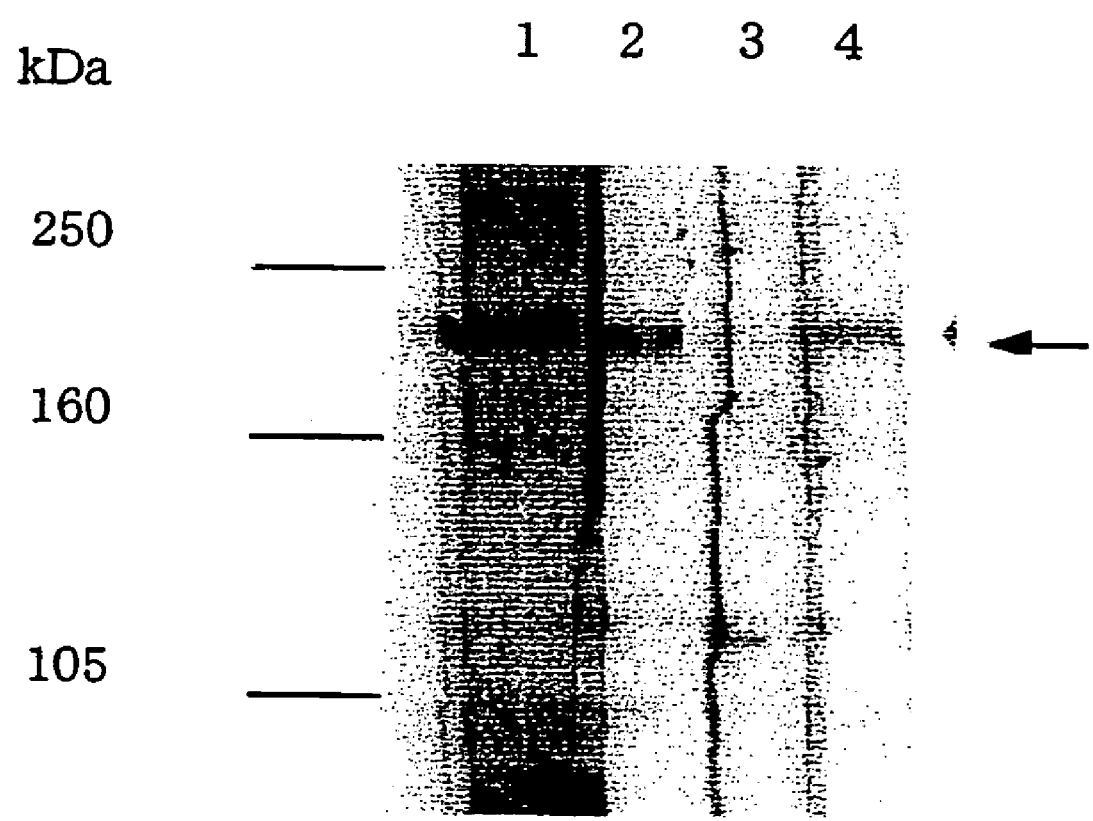
FIG. 16 is a photograph showing the result of Western blotting using an antibody established against the protease of the present invention, wherein Western blotting is carried out for various antiserums using the 293 cell as a host and a recombinant vWF-cleaving protease.

Subsequently, the antibodies prepared by the various aforementioned techniques were used to detect the protease of the present invention by Western blotting in accordance with a conventional technique (e.g., Current Protocols in Molecular Biology: Chapter 10 analysis of proteins, Chapter 11 immunology). More specifically, the culture supernatant of the recombinant unit-expressing 293 cell obtained in the procedure as described in Example 9 was subjected to SDS-PAGE under non-reducing conditions, transferred to a PVDF membrane, and confirmed using mouse or rabbit antiserum to confirm the expression of the genetically recombinant unit (FIG. 16). As a result, a band that was deduced to be derived from the protease of the present invention was found in a molecular size range of 160 to 250 kDa. Subsequently, the protease of the present invention was detected using starting plasma or the like and a recombinant unit under non-reducing conditions. As a result, a band was found in 105 to 160 kDa or 160 to 250 kDa (FIG. 17). Also, a band derived from a similar recombinant unit was detected in a monoclonal antibody established by immunizing a recombinant protein (clone No. CPHSWH-10).

Further, the C-terminal peptide sequence Phe-Ser-Pro-Ala-Pro-Gln-Pro-Arg-Arg-Leu-Leu-Pro-Gly-Pro-Gln-Glu-Asn-Ser-Val-Gln-Ser-Ser (SEQ ID NO: 37), which was one isoform of the protease of the present invention, was bound to KLH. The resultant was used as an immunogen to obtain a peptide antibody. With the use thereof, the protease of the present invention was detected from the plasma of healthy persons, plasma of TTP patients, or a culture supernatant of the recombinant unit under reducing conditions. As a result, a band of approximately 250 kDa that was deduced to be a signal derived from the protease of the present invention was found, although it was not clear based on plasma derived from some TTP patients (FIG. 18).

Figure 19:
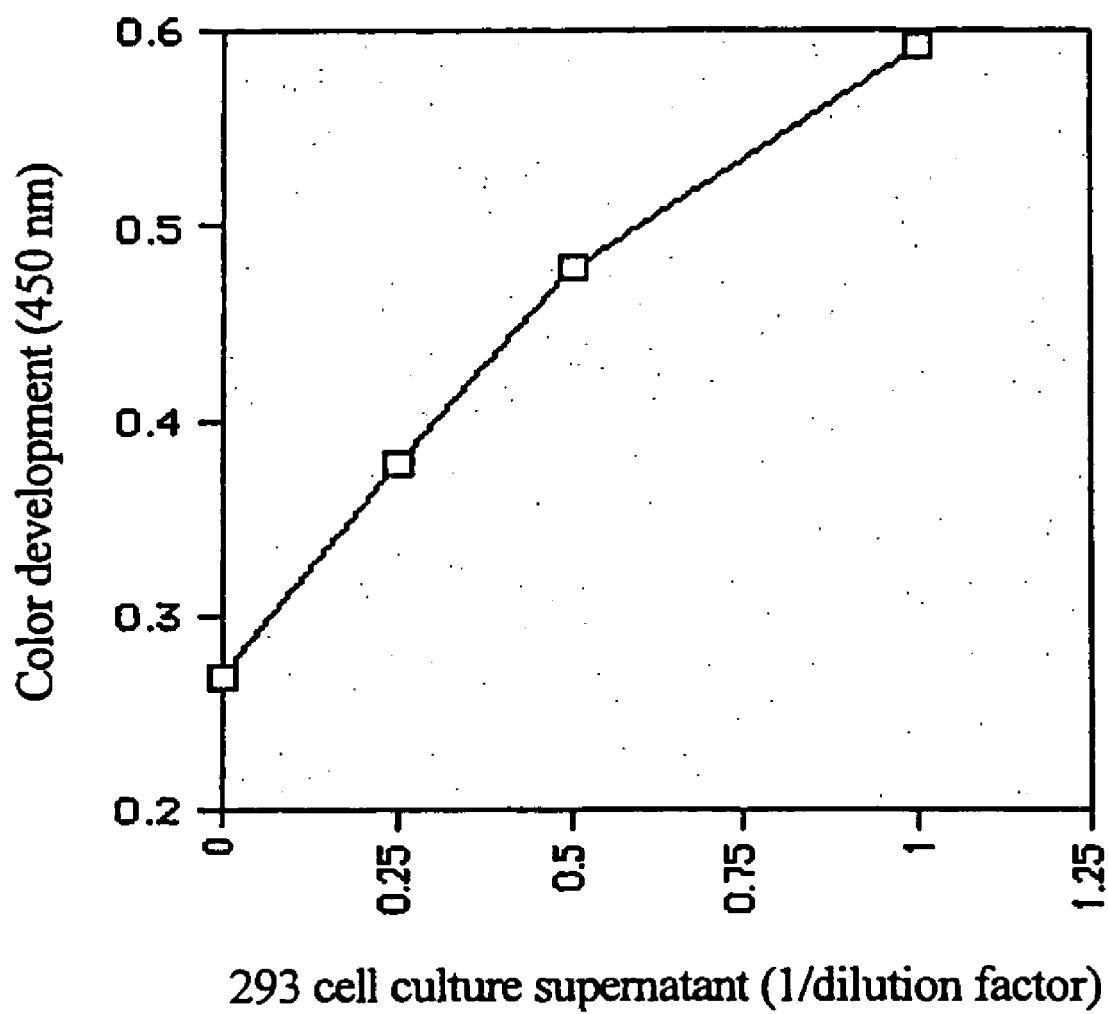
FIG. 19 is a diagram showing the result of ELISA using an antibody prepared against the vWF-cleaving protease.

Furthermore, enzyme immunoassay (ELISA) constructed by combining the obtained antibodies enabled the preparation of a calibration curve that is concentration-dependent at the culture supernatant level of the recombinant protein (FIG. 19). An example of ELISA is as follows. The obtained mouse anti-vWF-cleaving protease antibody was immobilized on the Maxisorp plate (Nunc), and 1/1, 1/2, and 1/4 diluents of the culture supernatant of the vWF-cleaving protease-temporarily expressing 293 cells were allowed to react in amounts of 100 µl/well (Mock supernatant as "0"). The plate was subjected to reaction, for example, at 37° C. for 1 hour, and then washed with 0.05% Tween 20/TBS. Thereafter, the 100-fold diluted rabbit anti-vWF-cleaving protease antibody was allowed to react in amounts of 100 µl/well, for example, at 37° C. for 1 hour, and the plate was washed with 0.05% Tween 20/TBS. The 1,000-fold diluted peroxidase-labeled anti-rabbit Ig antibody (BioRad) was then allowed to react in amounts of 100 µl/well, for example, at 37° C. for 1 hour, and the plate was washed with 0.05% Tween 20/TBS. Thereafter, color was developed for a given period of time using a coloring substrate TMBZ, the reaction was terminated using 1M sulfuric acid as a termination liquid, and the absorbance at 450 nm was assayed. The application thereof enabled the quantification of the protease of the present invention in a variety of specimens.

EXAMPLE 14

(Purification of the Protease Using an Antibody)

Figure 20:
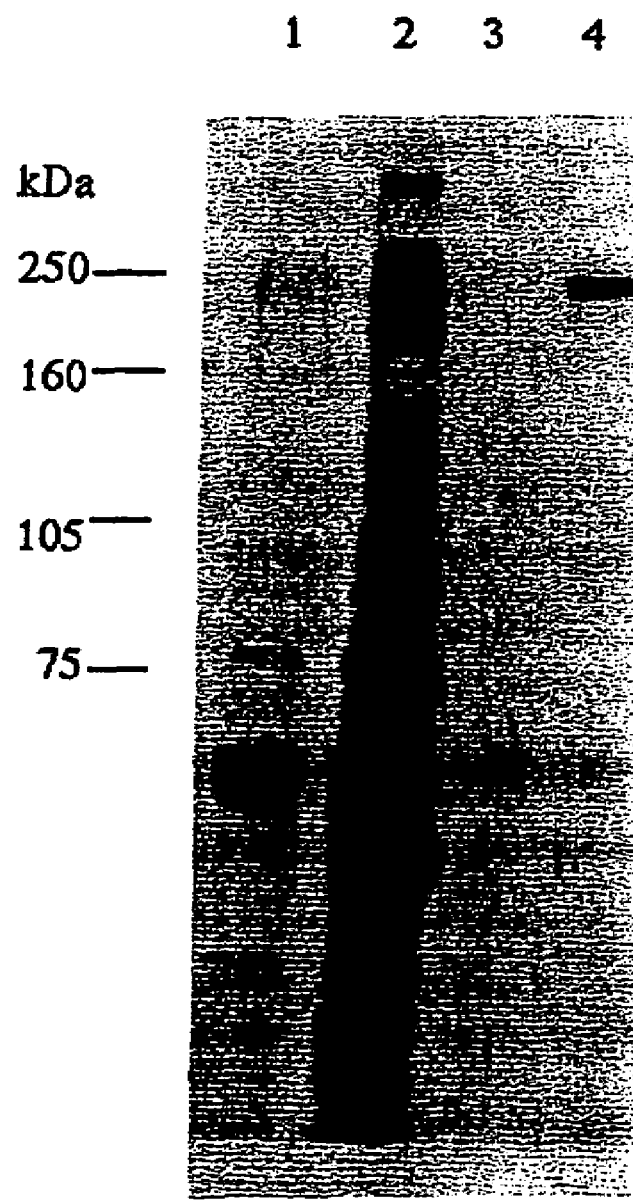
FIG. 20 is a photograph showing the result of SDS-PAGE (silver staining) analyzing each fraction of affinity purified vWF-cleaving protease using an antibody under reducing conditions.

The obtained antibody was bound to a suitable immobilization carrier to prepare an affinity column, and the resulting column was used to purify the protease of the present invention. The affinity column was prepared by immobilizing an antibody using Cellulofine for NHS activation (Chisso Corporation) in accordance with the included instructions. The thus prepared swollen carrier (about 1 ml) was used to apply the culture supernatant in which the recombinant gene had been expressed in the 293 cell of the protease as described in Example 9. Thereafter, the column was washed with 50 mM Tris-HCl and 0.1M NaCl (pH 7.5, hereafter referred to as "TBS"), and elution was carried out using a urea-containing 0.1M glycine buffer (pH 3). The eluted fraction was neutralized with 1M Tris-HCl (pH 8.5) and then dialyzed against TBS. FIG. 20 shows the results of SDS-PAGE analysis of the resulting purified protease. Also, the resulting purified fraction was found to have vWF-cleaving activity. The cleavage point of the vWF fragmented by this recombinant protease was found to be the position between residues Tyr 842 and Met 843 based on the analysis of the N-terminal amino acid sequence of the fragment. Also established were clones (e.g., Clone Nos. CPHSWH-7.2 and 10) that could be similarly subjected to purification with the use of the monoclonal antibody prepared by the method as described in Example 13.

Subsequently, the partial amino acid sequence of the purified protease was determined. In accordance with a conventional technique, the protease was subjected to SDS-PAGE, transferred to a PVDF membrane, air-dried, and then subjected to analysis using an automated protein sequencer (model 492; PE Applied Biosystems). As a result, the protease was found to comprise the first five amino acids of SEQ ID NO: 2 as a partial N-terminal sequence. This sequence was congruous with the N-terminal sequence of the mature unit of the protease of the present invention that was deduced from the genetic construction.

EXAMPLE 15

(Neutralization of the Protease Activity Using an Antibody)

Figure 21:
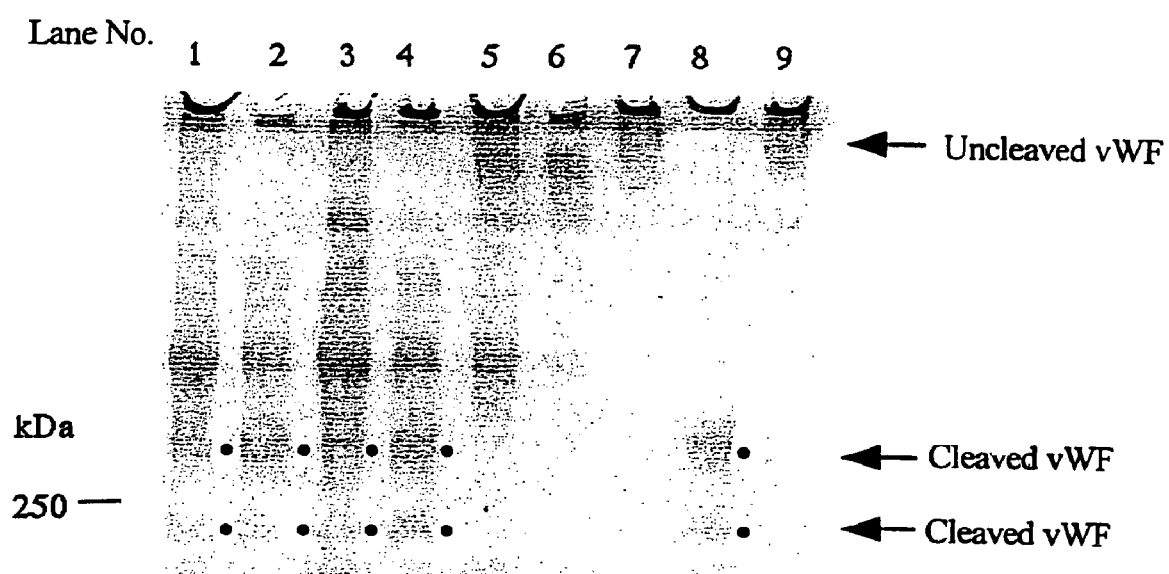
FIG. 21 is a photograph showing the results of evaluating neutralizing activity using an antibody (SDS-PAGE for analyzing vWF-cleaving activity under non-reducing conditions).

Activity of the aforementioned rabbit polyclonal antibody to neutralize the vWF-cleaving protease was evaluated. Normal rabbit serum, rabbit antiserum comprising the C-terminal peptide sequence, Phe-Ser-Pro-Ala-Pro-Gln-Pro-Arg-Arg-Leu-Leu-Pro-Gly-Pro-Gln-Glu-Asn-Ser-Val-Gln-Ser-Ser (SEQ ID NO:37) bound to KLH as an immunogen, and antiserum, the immunity of which had been induced by the protein expressed by the expression vector as shown in Example 7 or 8, were respectively allowed to pre-react at 37° C. for 1 hour with 1 to 10 µg/ml of gene recombinant vWF-cleaving protease (approximated by the Bradford technique) at a volume ratio of 1:1. Alternatively, a 5-fold diluted antiserum was allowed to pre-react under the above conditions with the protease at a volume ratio of 1:1. Thereafter, vWF-cleaving activity was evaluated by the method described above. As a result, it was found that antiserum, which had activity of inhibiting the protease of the present invention, were prepared by immunizing the protein (FIG. 21). (antagonist activity) (a metalloprotease inhibitor, i.e., EDTA, was determined to be a control). This indicates the possibility of constructing an acquired TTP patient-like model having a positive autoantibody against vWF-cleaving protease as well as the simple possibility of producing a neutralizing antibody.

EXAMPLE 16

(Construction of C-Terminus Deleted Modification Unit)

Figure 22:
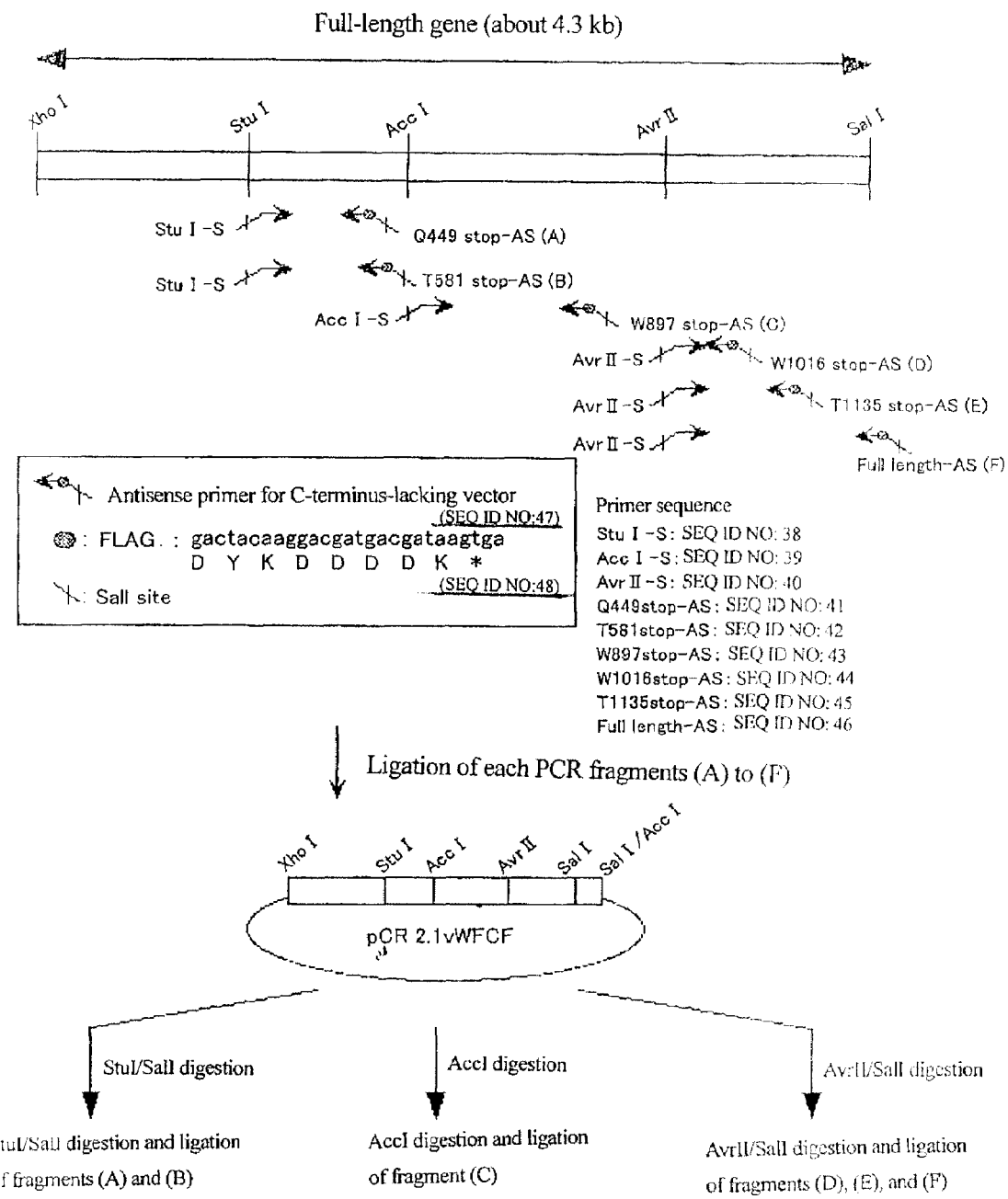
FIG. 22 is a diagram showing the construction of an expression vector for a molecular species lacking a C-terminal domain. Figure discloses SEQ ID NOS 47-48, respectively, in order of appearance.

Based on the strategy shown in FIG. 22, the full-length vWF-cleaving protease gene cloning vector (pCR 2.1 vWFCP) obtained in Example 6 or 7 was used to add a variant lacking domains located in a position following the C-terminus (T1135stop, W1016stop, W897stop, T581stop, and Q449stop: each numerical value indicates the number of amino acid residues between Met encoded by the initiation codon AGT and the termination codon, and indicates a site comprising the FLAG epitope (DNA sequence: gactacaag-gacgatgacgataagtga (SEQ ID NO: 47) and amino acid sequence: Asp Tyr Lys Asp Asp Asp Asp Lys (SEQ ID NO: 48)). Primers used herein are as follows. "S" indicates a sense primer, and "AS" indicates an antisense primer. Genes Stu I-S (SEQ ID NO: 38), Acc I-S (SEQ ID NO: 39), Avr II-S (SEQ ID NO: 40), Q449stop-AS (SEQ ID NO: 41), T581stop-AS (SEQ ID NO: 42), W897stop-AS (SEQ ID NO: 43), W1016stop-AS (SEQ ID NO: 44), T1135stop-AS (SEQ ID NO: 45), and full-length-AS (SEQ ID NO: 46) were prepared and incorporated in the pCAG expression vector in accordance with the method as used in Examples 8 and 9. This expression vector was introduced in the Hela cell. The primer pair shown at the bottom of the restriction map in the upper portion of FIG. 22 was used to obtain PCR fragments (A) to (F). Each PCR fragment was ligated to pCR 2.1 vWFCP. Further, the resultant was digested with StuI/SalI, and fragments (A) and (B) were digested with StuI/SalI and then ligated. These fragments were further digested with AccI, and fragment (C) was also digested with AccI, followed by ligation. The ligation product was digested with AvrII/SalI, and fragments (D), (E), and (F) were also digested with AvrII/SalI, followed by ligation. As a result, a variant lacking a region between the C-terminus and the position W897 was found to have activity, although it was the result of qualitative analysis. Such a way of approach enables the identification of various functional domains. The design of molecules comprising these domains and having no protease activity is considered to realize the design of antagonists or agonists.

INDUSTRIAL APPLICABILITY

The findings of the present invention have led to the possibility of replacement therapy for patients having diseases resulting from deficiency of a protease, such as thrombotic thrombocytopenic purpura. This also realizes the establishment of methods for gene cloning and efficient purification from serum or plasma. In particular, the information provided by the present invention enables gene recombination based on the obtained nucleotide sequence and stable production and provision of the protease according to the present invention, which have been heretofore difficult to achieve. Also, these can be applied to replacement therapy for TTP patients, inhibition of platelet plug formation involved with heart infarction or brain infarction, inhibition of arteriosclerosis, prevention of restenosis, reembolization, or infarction involved with PTCA, prevention of reembolization involved with PTCR, and prevention of platelet plug formation caused by HUS or O-157. Diagnosis and therapy utilizing the gene encoding the protease of the present invention or an antibody thereagainst can be realized.

All publications cited herein are incorporated herein in their entirety. A person skilled in the art would easily understand that various modifications and changes of the present invention are feasible within the technical idea and the scope of the invention as disclosed in the attached claims. The present invention is intended to include such modifications and changes.

What is claimed is:

1. An isolated DNA encoding a protease that is capable of cleaving a bond between residues Tyr-842 and Met-843 of von Willebrand factor and that comprises a polypeptide chain having the amino acid sequence as shown in SEQ ID NO: 3 as the N-terminal partial sequence of a mature protein.

2. A vector comprising the DNA encoding a protease according to claim 1, which comprises the nucleotide sequence as shown in SEQ ID NO: 6.

3. The vector according to claim 2 comprising a polypeptide encoding domain and specialized in the expression of said polypeptide.

4. An isolated cell transformed or transfected with the vector according to claim 2.

* * * * *